United States Patent
Elumalai et al.

(10) Patent No.: US 11,319,552 B2
(45) Date of Patent: May 3, 2022

(54) METHODS FOR IMPROVING TRANSFORMATION FREQUENCY

(71) Applicant: SYNGENTA PARTICIPATIONS AG, Basel (CH)

(72) Inventors: Sivamani Elumalai, Research Triangle Park, NC (US); Qiudeng Que, Research Triangle Park, NC (US); Michael Schweiner, Wake Forest, NC (US)

(73) Assignee: Syngenta Participations AG, Basel (CH)

( * ) Notice: Subject to any disclaimer, the term of this patent is extended or adjusted under 35 U.S.C. 154(b) by 251 days.

(21) Appl. No.: 16/466,845

(22) PCT Filed: Nov. 28, 2017

(86) PCT No.: PCT/US2017/063343
§ 371 (c)(1),
(2) Date: Jun. 5, 2019

(87) PCT Pub. No.: WO2018/106470
PCT Pub. Date: Jun. 14, 2018

(65) Prior Publication Data
US 2019/0345510 A1   Nov. 14, 2019

Related U.S. Application Data

(60) Provisional application No. 62/431,664, filed on Dec. 8, 2016.

(51) Int. Cl.
*C12N 15/82* (2006.01)
*A01N 57/20* (2006.01)
*C12N 9/10* (2006.01)
*G01N 33/50* (2006.01)

(52) U.S. Cl.
CPC ......... *C12N 15/8277* (2013.01); *A01N 57/20* (2013.01); *C12N 9/1029* (2013.01); *C12Y 203/01183* (2013.01); *G01N 33/5097* (2013.01)

(58) Field of Classification Search
CPC .................................................. C12N 15/8277
See application file for complete search history.

(56) References Cited

U.S. PATENT DOCUMENTS

| 5,919,675 A | 7/1999 | Adams et al. |
| 6,096,947 A * | 8/2000 | Jayne ................. C12N 15/8216 800/300 |
| 6,395,966 B1 | 5/2002 | Mumm et al. |

FOREIGN PATENT DOCUMENTS

| WO | 2015026887 A1 | 2/2015 |
| WO | 2016/100804 A1 | 6/2016 |
| WO | 2014/093485 A1 | 6/2019 |
| WO | 2009/152359 A2 | 12/2019 |

OTHER PUBLICATIONS

Partial Supplementary European Search Report for EP 17 87 8878 dated May 25, 2020.
Sivamani, Elumalai: "A study on optimization of pat gene expression cassette for maize transformation", in: Molecular Biology Reports. Mar. 11, 2019, pp. 3009-3017. XP055694946. https://link.springer.comjcontent/pdf/.
International Search Report for PCT/US2017/063343 dated Feb. 16, 2018.
Que et al., "Maize Transformation Technology Development for Commercial Even Generation", Frontiers in Plant Science, Aug. 5, 2014, vol. 5, No. 379, 1-19.
Kita et al., "Generation and Characterization of Herbicide-Resistant Soybean Plants Expressing Novel Phosphinothricin N-Acetyltransferase Genes", Breeding Science, Sep. 1, 2009, vol. 59, 245-251.

* cited by examiner

*Primary Examiner* — David H Kruse
(74) *Attorney, Agent, or Firm* — Dale Skalla

(57) ABSTRACT

The present invention is drawn to compositions and methods for improving transformation frequency. The compositions, synthetic selectable marker genes, are used in transformation methods and result in increased transformation frequency.

17 Claims, No Drawings
Specification includes a Sequence Listing.

SEQUENCE LISTING

```
<160> NUMBER OF SEQ ID NOS: 35

<210> SEQ ID NO 1
<211> LENGTH: 552
<212> TYPE: DNA
<213> ORGANISM: Artificial Sequence
<220> FEATURE:
<223> OTHER INFORMATION: derived from Streptomyces viridochromogenes

<400> SEQUENCE: 1 atgtcccgg agcgccgcc ggtggagatc cgcccggcca ccgccgccga catggccgcc      60
gtgtgcgaca tcgtgaacca ctacatcgag acctccaccg tgaacttccg caccgagccg     120 cagacccccgc aggagtggat cgacgacctc gagcgcctcc aggaccgcta cccgtggctc     180
gtggccgagg tggagggcgt ggtggccggc atcgcctacg ccggcccgtg gaaggcccgc     240
aacgcctacg actggaccgt ggagtccacc gtgtacgtgt cccaccgcca ccagcgcctc     300
ggcctcggct ccaccctcta cacccacctc ctcaagtcta tggaggccca gggcttcaag     360
tccgtggtgg ccgtgatcgg cctcccgaac gacccgtccg tgcgcctcca cgaggccctc     420
ggctacaccg cccgcggcac cctgcgcgcc gccggctaca agcacggcgg ctggcacgac     480
gtgggcttct ggcagcgcga cttcgagctg ccggccccgc cgcgcccggt gcgcccggtg     540
acccagattt ga                                                         552

<210> SEQ ID NO 2
<211> LENGTH: 5552
<212> TYPE: DNA
<213> ORGANISM: Artificial Sequence
<220> FEATURE:
<223> OTHER INFORMATION: derived from Streptomyces viridochromogenes and
      Zea mays

<400> SEQUENCE: 2
ggaaaaccaa acaacgaat aagcaaactg caggaaaagt atgcagtgga aaccaaccca       60
gattcggacg ataggaaagt atcaagtgaa tgatttgcca ggaaaaggag aggggtaaaa     120
```

```
agggcgaag atttagaaga tctaaagcac aagaaccaga gattagattg aacaataggg      180
aacttggagc atccttttt  tcttcaggga aaaactgaaa atccaaacca tgttgagcaa     240
aaccgagtgg gattggaaac caaaaaaccc gagataaaga aactcgagaa aaagcatgaa    300
atcgaaacca acttcagtaa aacaaaagga ggacagaaaa gaaagtcgga agctataaag    360
aatacattaa cattcagtga aacagcatgc tgtcttcttc ttttttatg  cacaacagag    420 catacatata taccttccca ggctgaggac ttggcggagg agagccgcgg ataggttggc    480
ggtgcagacg gtctggacgg gcccgaagac ggagacgaac agcgggccct tcctgcccag    540
gcaccacgct tggaacgcca agcacgcgcc aaccgcggcc ccgccgagga cgacgatccc    600
cgcgacaagc gtggcgtcga tcctgggcga ccccaagccg aggaacctcc cttccaggac    660
gagccgtagg acggcggtga gagaggcacc cgtcgcggag gtggcgcagc acaaggtgag    720
cagcgcgggg aaggcggcga gcgtggcggc ctgcaggacg tgacgagcg  cgaagacggt    780 gacgccggcg acgaggcagc agcagccgag gttccagtcg taggaggaag ccggaccaaa    840
ccgggcaatg caacctgcag atgcactaga cggaggtaac gaggaggagg agaaaacaga    900
gcaagagcag gcggagagaa gatagagcaa acacgagtg  aggcacagcg taagcactcg    960
gtagaagtct ccagaggcga ggtgcgcaca ggagaacaga tgagtaaagt cagccaagga   1020
tgcacgatcc aacggctacg aattttggga gtgacgtgga taggctcaaa ggcgccattt   1080
ccatccggct ttatagtatt ttaaaaaaat tcattttcct ccctctagtg tgtgcggagg   1140
cgtgagcccg tttaacggcg ttgagaagtc taacggacac caaccacaac caggaaccag   1200
cgccggccgc gccgccgagt gaagcagact gcatacggca cggcgcggca tctctctggc   1260
tgcctctcga gagttccgcc cccaccttcc cgcggtagcg tggtggtttc gctttccgct   1320
gtcggcatcc ggaagttgcg tggcagagtg gacggagacg aggccgggtc ctccagctcc   1380
tctcaaacgt cacggcaccg gcatccggca gccagcgcgg tccttcccaa ccactcgttc   1440
ccaacccatc ccccttcctc gcccgccgtc ataaatagcc agcccatcc  ccagcttctt   1500 tccccaacct catcttctct ccttttgctc tgaacgcaca caccgcccgg tctccgatct   1560
ccgatccccg atccctcgt  cgatcctagg tacggcgacc atcctacccc cccccccccc   1620
ccctctctct ctgccttctc tagatcggcg atccgatcca tgcttacttg gttagggcct   1680
gctaactatg ttcatgtttg cgttagatcc gtgcatggac gcgatctgta cacaccagac   1740
gcgttctgat tgctagctaa ctcgccagta cctgggaatc ctgggatggc tgtagccggc   1800
cccgcacgca gacgggaccg atttcatgat tctctatttt tttctttgtt tcgttgccta   1860
gggtttcgtt cgatcgatcc gcgttattct ttatttccat atattctggt acgatgttga   1920
tacggttcga ccgtgctgct tacgttctgt gcgcttgttt gccgggtcat ttttaccttg   1980 cctttttgt  atggtttggt tgtggcgatg tggtctggtc gggctgtcgt tctagatcgg   2040
agtagagtgc tgtttcaaac tgtctagcgg atctattaga tttggatctg catgtgtgac   2100
atatatcttc gtagttaaga tgatgcatct gtatgtgtga catgcggatc tattagattt   2160
ggatctgtat gtgtgacata tatcttcgta gttgagatga tgcatctgta tgtgtgacat   2220
atatcttcgt agttaagatt atgcatggaa atatcaatcc tttagataag gacgggtata   2280
cttgttgctg tgggttttac tggtacttcg atagatgcat atacatgatc taacatgctt   2340
agatacatga agtaacatgc tgctacggtt taataattct tgagttgatt tttactggta   2400
cttagataga tgtatataca tgcttagata catgaagtaa catgctccta cagttccttt   2460
aatcattatt gagtacctat atattctaat aaatcagtat gttttaaatt attttgattt   2520
```

```
tactggtact tagatagatg tatatataca tgctcaaaca tgcttagata catgaagtaa    2580
catgctgcta cggtttagtc attattgagt gcctatatat tctaataaat cagtatgttt    2640
taaattattt tgattttact ggtacttaga tagatgtata tatacatgct caaacatgct    2700
tagatacatg aagtaatatg ctactacggt taattgttc  ttgagtacct atatattcta    2760
ataaatcagt atgttttaaa ttatttcgat tttactggta cttagataga tgtatatata    2820
catgcttaga tacatgaagt aacatgctac tacggtttaa ttgttcttga atacctatat    2880
attctaataa atcagtatgt tttaaattat ttcgatttta ctggtactta gatagatgta    2940
tatatacatg ctcgaacatg cttagataca tgaagtaaca tgctacatat atattataat    3000
aaatcagtat gtcttaaatt attttgattt tactggtact tagatagatg tatatacatg    3060
ctcaaacatg cttagataca tgaagtaaca tgctactacg gttaatcat  tattgagtac    3120 ctatatattc taataaatca gtatgttttc aattgttttg attttactgg tacttagata    3180
tatgtatata tacatgctcg aacatgctta gatacgtgaa gtaacatgct actatggtta    3240
attgttcttg agtacctata tattctaata atcagtatg  ttttaaatta tttcgatttt    3300
actggtactt agatagatgt atatatacat gctcgaacat gcttagatac atgaagtaac    3360
atgctactac ggtttaatcg ttcttgagta cctatatatt ctaataaatc agtatgtctt    3420
aaattatctt gatttactg  gtacttagat agatgtatat acatgcttag atacatgaag    3480
taacatgcta ctatgattta atcgttcttg agtacctata tattctaata atcagtatg   3540 tttttaatta ttttgatttt actggtactt agatagatgt atatatacat gctcgaacat    3600
gcttagatac atgaagtaac atgctactac ggtttaatca ttcttgagta cctatatatt    3660
ctaataaatc agtatgtttt taattatttt gatattactg gtacttaaca tgtttagata    3720
catcatatag catgcacatg ctgctactgt taatcattc  gtgaatacct atatattcta    3780
atatatcagt atgtcttcta attattatga ttttgatgta cttgtatggt ggcatatgct    3840
gcagctatgt gtagattttg aatacccagt gtgatgagca tgcatggcgc cttcatagtt    3900
catatgctgt ttatttcctt tgagactgtt cttttttgtt gatagtcacc ctgttgtttg    3960
gtgattctta tccagatcca gatcttcgag atcctaaacc atgtccccgg agcgccgccc    4020
ggtggagatc cgcccggcca ccgccgccga catggccgcc gtgtgcgaca tcgtgaacca    4080
ctacatcgag acctccaccg tgaacttccg caccgagccg cagaccccgc aggagtggat    4140
cgacgacctc gagcgcctcc aggaccgcta cccgtggctc gtggccgagg tggagggcgt    4200
ggtggccggc atcgcctacg ccggcccgtg aaggcccgc  aacgcctacg actgaccgt    4260 ggagtccacc gtgtacgtgt cccaccgcca ccagcgcctc ggcctcggct ccaccctcta    4320
cacccacctc ctcaagtcta tggaggccca gggcttcaag tccgtggtgg ccgtgatcgg    4380
cctcccgaac gacccgtccg tgcgcctcca cgaggccctc ggctacaccg cccgcggcac    4440
cctgcgcgcc gccggctaca agcacggcgg ctggcacgac gtgggcttct ggcagcgcga    4500
cttcgagctg ccggccccgc cgcgcccggt gcgcccggtg acccagattt gagccaaggt    4560
tcaattaagc tgctgctgta cctgggtatc tgcgtcgtct ggtgccctct ggtgtacctc    4620
tatatggatc tcgtcgtcta ataaacatct gtggtttgtg tgtcatcaat cgtggttgtg    4680
gcttcgttgg tttaatggac ctgttgtgtc ctctgtgttg tacccaaaac tcttctgcag    4740
cagtatggct tgaatcctta tgaagtttga tatttgaact taaagtctg  ctcattatgt    4800 tttttctgg  ttatatctcc taattaactg cctgggatca aatttgattc gctggtgttt    4860
```

```
attggacccc tcccaggttc ttgctttcta ccgtttcttg ctgaatgtta acttgattct   4920
gtcaggctca gtttcccact atggcttaca gcttaacgtg tttggtttgt tgaatgttaa   4980
cttggttttg tcaagctcag ttttttactc tggcttacag cataacatgt ttgacttttg   5040
gttttgctgc tttgttattg ggttctgggt agttcttgat gaatccaaaa gatcatgtgc   5100
acagccatat tatctattta agcgatccag gttattacta tgaaaggatg ccttctagct   5160
aaggagtagt taggtttttt cttcaaggtt aaattttctc gatgctctag tgttcctgtg   5220
accataatca taataattcc tttgaaagct ctatggtccc tggaagcagg gcatacaatg   5280
caagacagca acttgatcac atcaactgaa gtatacaggg ttctcttaac tcttggtgac   5340
ttcggtttaa tggaccggtt gtactcgtgt tctatccgta accgttgtga tgtcttgtgt   5400
gtttggttgc gggatagctg ggaccacgac gtttccgtct aattctgatg gatagctata   5460
gacggcactg agatggttat attataacct ctgatcctga actctacgag atcgtctcat   5520
ccgtcattgc caccaaatac accattaaat ta                                 5552
```

```
<210> SEQ ID NO 3
<211> LENGTH: 5527
<212> TYPE: DNA
<213> ORGANISM: Artificial Sequence
<220> FEATURE:
<223> OTHER INFORMATION: derived from Streptomyces viridochromogenes and
      Zea mays

<400> SEQUENCE: 3
```

```
ggaaaaccaa acaacgaat aagcaaactg caggaaaagt atgcagtgga aaccaaccca     60
gattcggacg ataggaaagt atcaagtgaa tgatttgcca ggaaaaggag aggggtaaaa   120
aggggcgaag atttagaaga tctaaagcac aagaaccaga gattagattg aacaataggg   180
aacttggagc atccttttt tcttcaggga aaaactgaaa atccaaacca tgttgagcaa   240
aaccgagtgg gattggaaac caaaaaaccc gagataaaga aactcgagaa aaagcatgaa   300
atcgaaacca acttcagtaa aacaaaagga ggacagaaaa gaaagtcgga agctataaag   360
aatacattaa cattcagtga aacagcatgc tgtcttcttc tttttttatg cacaacagag   420
catacatata taccttccca ggctgaggac ttggcggagg agagccgcgg ataggttggc   480
ggtgcagacg gtctggacgg gcccgaagac ggagacgaac agcgggccct tcctgcccag   540
gcaccacgct tggaacgcca agcacgcgcc aaccgcggcc ccgccaggga cgacgatccc   600
cgcgacaagc gtggcgtcga tcctgggcga ccccaagccg aggaacctcc cttccaggac   660
gagccgtagg acggcggtga gagaggcacc cgtcgcggag gtggcgcagc acaaggtgag   720 cagccgcgggg aaggcggcga gcgtggcggc ctgcaggacg gtgacgagcg cgaagacggt   780
gacgccggcg acgaggcagc agcagccgag gttccagtcg taggaggaag ccggaccaaa   840
ccgggcaatg caacctgcag atgcactaga cggaggtaac gaggaggagg agaaaacaga   900
gcaagagcag gcggagagaa gatagagcaa acacgagtg aggcacagcg taagcactcg   960
gtagaagtct ccagaggcga ggtgcgcaca ggagaacaga tgagtaaagt cagccaagga   1020
tgcacgatcc aacggctacg aattttgga gtgacgtgga taggctcaaa ggcgccattt   1080
ccatccggct ttatagtatt ttaaaaaaat tcatttcct ccctctagtg tgtgcggagg   1140
cgtgagcccg tttaacggcg ttgagaagtc taacggacac caaccacaac caggaaccag   1200
cgccggccgc gccgccgagt gaagcagact gcatacggca cggcgcggca tctctctggc   1260
tgcctctcga gagttccgcc cccaccttcc cgcggtagcg tggtggtttc gctttccgct   1320
```

-continued

```
gtcggcatcc ggaagttgcg tggcagagtg gacggagacg aggccgggtc ctccagctcc      1380
tctcaaacgt cacggcaccg gcatccggca gccagcgcgg tccttcccaa ccactcgttc      1440
ccaacccatc ccccttcctc gcccgccgtc ataaatagcc agccccatcc ccagcttctt      1500
tccccaacct catcttctct ccttttgctc tgaacgcaca caccgcccgg tctccgatct      1560
ccgatccccg atccctcgt cgatcctagg tacggcgacc atcctacccc ccccccccc       1620
ccctctctct ctgccttctc tagatcggcg atccgatcca tgcttacttg gttagggcct      1680
gctaactatg ttcatgtttg cgttagatcc gtgcatggac gcgatctgta cacaccagac      1740
gcgttctgat tgctagctaa ctcgccagta cctgggaatc ctgggatggc tgtagccggc      1800
cccgcacgca gacgggaccg atttcatgat tctctatttt tttctttgtt tcgttgccta      1860
gggtttcgtt cgatcgatcc gcgttattct ttatttccat atattctggt acgatgttga      1920
tacggttcga ccgtgctgct tacgttctgt gcgcttgttt gccgggtcat ttttaccttg      1980
cctttttgt atggtttggt tgtggcgatg tggtctggtc gggctgtcgt tctagatcgg       2040
agtagagtgc tgtttcaaac tgtctagcgg atctattaga tttggatctg catgtgtgac      2100
atatatcttc gtagttaaga tgatgcatct gtatgtgtga catgcggatc tattagattt      2160
ggatctgtat gtgtgacata tatcttcgta gttgagatga tgcatctgta tgtgtgacat      2220
atatcttcgt agttaagatt atgcatggaa atatcaatcc tttagataag gacgggtata      2280
cttgttgctg tgggttttac tggtacttcg atagatgcat atacatgatc taacatgctt      2340
agatacatga agtaacatgc tgctacggtt taataattct tgagttgatt tttactggta      2400
cttagataga tgtatataca tgcttagata catgaagtaa catgctccta cagttccttt      2460
aatcattatt gagtacctat atattctaat aaatcagtat gttttaaatt attttgattt      2520
tactggtact tagatagatg tatatataca tgctcaaaca tgcttagata catgaagtaa      2580
catgctgcta cggtttagtc attattgagt gcctatatat tctaataaat cagtatgttt      2640
taaattattt tgattttact ggtacttaga tagatgtata tacatgct caaacatgct       2700
tagatacatg aagtaatatg ctactacggt ttaattgttc ttgagtacct atatattcta      2760
ataaatcagt atgttttaaa ttatttcgat tttactggta cttagataga tgtatatata      2820
catgcttaga tacatgaagt aacatgctac tacggtttaa ttgttcttga atacctatat      2880
attctaataa atcagtatgt tttaaattat ttcgatttta ctggtactta gatagatgta      2940
tatacatg ctcgaacatg cttagataca tgaagtaaca tgctacatat atattataat       3000
aaatcagtat gtcttaaatt attttgattt tactggtact tagatagatg tatatacatg      3060
ctcaaacatg cttagataca tgaagtaaca tgctactacg gtttaatcat tattgagtac      3120
ctatatattc taataaatca gtatgttttc aattgttttg attttactgg tacttagata      3180
tatgtatata tacatgctcg aacatgctta gatacgtgaa gtaacatgct actatggtta      3240
attgttcttg agtacctata tattctaata atcagtatg ttttaaatta tttcgatttt       3300
actggtactt agatagatgt atatatacat gctcgaacat gcttagatac atgaagtaac      3360
atgctactac ggtttaatcg ttcttgagta cctatatatt ctaataaatc agtatgtctt      3420
aaattatctt gatttactg gtacttagat agatgtatat acatgcttag atacatgaag       3480
taacatgcta ctatgattta atcgttcttg agtacctata tattctaata atcagtatg       3540
tttttaatta ttttgatttt actggtactt agatagatgt atatatacat gctcgaacat      3600
gcttagatac atgaagtaac atgctactac ggtttaatca ttcttgagta cctatatatt      3660
ctaataaatc agtatgtttt taattatttt gatattactg gtacttaaca tgtttagata      3720
```

```
catcatatag catgcacatg ctgctactgt ttaatcattc gtgaatacct atatattcta    3780
atatatcagt atgtcttcta attattatga ttttgatgta cttgtatggt ggcatatgct    3840
gcagctatgt gtagattttg aatacccagt gtgatgagca tgcatggcgc cttcatagtt    3900
catatgctgt ttatttcctt tgagactgtt cttttttgtt gatagtcacc ctgttgtttg    3960
gtgattctta tccagatgtc cccggagcgc cgcccggtgg agatccgccc ggccaccgcc    4020
gccgacatgg ccgccgtgtg cgacatcgtg aaccactaca tcgagacctc caccgtgaac    4080
ttccgcaccg agccgcagac cccgcaggag tggatcgacg acctcgagcg cctccaggac    4140
cgctacccgt ggctcgtggc cgaggtggag ggcgtggtgg ccggcatcgc ctacgccggc    4200
ccgtggaagg cccgcaacgc ctacgactgg accgtggagt ccaccgtgta cgtgtcccac    4260
cgccaccagc gcctcggcct cggctccacc ctctacaccc acctcctcaa gtctatggag    4320
gcccagggct tcaagtccgt ggtggccgtg atcggcctcc cgaacgaccc gtccgtgcgc    4380
ctccacgagg ccctcggcta caccgcccgc ggcaccctgc gcgccgccgg ctacaagcac    4440
ggcggctggc acgacgtggg cttctggcag cgcgacttcg agctgccggc ccgccgcgc    4500 ccggtgcgcc cggtgaccca gatttgagcc aaggttcaat taagctgctg ctgtacctgg    4560
gtatctgcgt cgtctggtgc cctctggtgt acctctatat ggatctcgtc gtctaataaa    4620
catctgtggt ttgtgtgtca tcaatcgtgg ttgtggcttc gttggtttaa tggacctgtt    4680
gtgtcctctg tgttgtaccc aaaactcttc tgcagcagta tggcttgaat ccttatgaag    4740
tttgatattt gaacttaaaa gtctgctcat tatgtttttt tctggttata tctcctaatt    4800
aactgcctgg gatcaaattt gattcgctgg tgtttattgg acccctccca ggttcttgct    4860
ttctaccgtt tcttgctgaa tgttaacttg attctgtcag gctcagtttc ccactatggc    4920
ttacagctta acgtgtttgg tttgttgaat gttaacttgg ttttgtcaag ctcagttttt    4980
tactctggct tacagcataa catgtttgac ttttggtttt gctgctttgt tattgggttc    5040
tgggtagttc ttgatgaatc caaaagatca tgtgcacagc catattatct atttaagcga    5100
tccaggttat tactatgaaa ggatgccttc tagctaagga gtagttaggt ttttcttca    5160 aggttaaatt ttctcgatgc tctagtgttc ctgtgaccat aatcataata attcctttga    5220
aagctctatg gtccctggaa gcagggcata caatgcaaga cagcaacttg atcacatcaa    5280
ctgaagtata cagggttctc ttaactcttg gtgacttcgg tttaatggac cggttgtact    5340
cgtgttctat ccgtaaccgt tgtgatgtct tgtgtgtttg gttgcgggat agctgggacc    5400
acgacgtttc cgtctaattc tgatggatag ctatagacgg cactgagatg gttatattat    5460
aacctctgat cctgaactct acgagatcgt ctcatccgtc attgccacca aatacaccat    5520
taaatta                                                              5527

<210> SEQ ID NO 4
<211> LENGTH: 6067
<212> TYPE: DNA
<213> ORGANISM: Artificial Sequence
<220> FEATURE:
<223> OTHER INFORMATION: derived from Streptomyces viridochromogenes and
      Zea mays

<400> SEQUENCE: 4
agctgcttgt ggggaccaga caaaaaagga atggtgcaga attgttaggc gcacctacca      60
aaagcaactt tgcctttatt gcaaagataa agcagattcc tctagtacaa gtggggaaca     120
aaataacgtg gaaaagagct gtcctgacag cccactcact attgcgtttg acgaacgcag     180
```

```
tgacgaccac aaaactcgag acttttcaac aaagggtatt atccggaaac ctcctcggat    240
tccattgccc agctatctgt cactttattg tgaagatagt ggaaaaggaa ggtggctcct    300
acaaatgcca tcattgcgat aaaggaaagg ctatcgttga agatgcctct gccgacagtg    360
gtcccaaaga tggacccca cccacgagga gcatcgtgga aaagaagac gttccaacca     420 cgtcttcaaa gcaagtggat tgatgtgata tctccactga cgtaagggtt gacgaacaat    480
cccactatcc ttctgcctaa ttagctaacg gacccggaaa accaaaacaa cgaataagca    540
aactgcagga aaagtatgca gtggaaacca acccagattc ggacgatagg aaagtatcaa    600
gtgaatgatt tgccaggaaa aggagagggg taaaagggg cgaagattta gaagatctaa     660
agcacaagaa ccagagatta gattgaacaa tagggaactt ggagcatcct tttttcttc     720 agggaaaaac tgaaaatcca aaccatgttg agcaaaaccg agtgggattg gaaaccaaaa    780
aacccgagat aagaaactc gagaaaaagc atgaaatcga aaccaacttc agtaaaacaa     840
aaggaggaca gaaaagaaag tcggaagcta taaagaatac attaacattc agtgaaacag    900
catgctgtct tcttcttttt ttatgcacaa cagagcatac atatatacct tcccaggctg    960
aggacttggc ggaggagagc cgcggatagg ttggcggtgc agacggtctg gacgggcccg   1020
aagacggaga cgaacagcgg gcccttcctg cccaggcacc acgcttggaa cgccaagcac   1080
gcgccaaccg cggccccgcc gaggacgacg atccccgcga caagcgtggc gtcgatcctg   1140 ggcgaccca agccgaggaa cctcccttcc aggacgagcc gtaggacggc ggtgagagag    1200
gcacccgtcg cggaggtggc gcagcacaag gtgagcagcg cggggaaggc ggcgagcgtg   1260
gcggcctgca ggacggtgac gagcgcgaag acggtgacgc cggcgacgag gcagcagcag   1320
ccgaggttcc agtcgtagga ggaagccgga ccaaaccggg caatgcaacc tgcagatgca   1380
ctagacggag gtaacgagga ggaggagaaa acagagcaag agcaggcgga gagaagatag   1440
agcaaaacac gagtgaggca cagcgtaagc actcggtaga agtctccaga ggcgaggtgc   1500
gcacaggaga acagatgagt aaagtcagcc aaggatgcac gatccaacgg ctacgaattt   1560
ttggagtgac gtggataggc tcaaaggcgc catttccatc cggctttata gtattttaaa   1620
aaaattcatt ttcctccctc tagtgtgtgc ggaggcgtga gcccgtttaa cggcgttgag   1680
aagtctaacg gacaccaacc acaaccagga accagcgccg gccgcgccgc cgagtgaagc   1740
agactgcata cggcacggcg cggcatctct ctggctgcct ctcgagagtt ccgccccac    1800 cttcccgcgg tagcgtggtg gtttcgcttt ccgctgtcgg catccggaag ttgcgtggca   1860
gagtggacgg agacgaggcc gggtcctcca gctcctctca aacgtcacgg caccggcatc   1920
cggcagccag cgcggtcctt cccaaccact cgttcccaac ccatcccct tcctcgcccg    1980 ccgtcataaa tagccagccc catccccagc ttctttcccc aacctcatct tctctccttt   2040
tgctctgaac gcacacaccg cccggtctcc gatctccgat ccccgatccc ctcgtcgatc   2100
ctaggtacgg cgaccatcct accccccccc cccccccctc tctctctgcc ttctctagat   2160
cggcgatccg atccatgctt acttggttag ggcctgctaa ctatgttcat gtttgcgtta   2220
gatccgtgca tggacgcgat ctgtacacac cagacgcgtt ctgattgcta gctaactcgc   2280
cagtacctgg gaatcctggg atggctgtag ccggccccgc acgcagacgg gaccgatttc   2340
atgattctct attttttttct ttgtttcgtt gcctagggtt tcgttcgatc gatccgcgtt   2400
attctttatt tccatatatt ctggtacgat gttgatacgg ttcgaccgtg ctgcttacgt   2460
tctgtgcgct tgtttgccgg gtcattttta ccttgccttt tttgtatggt ttggttgtgg   2520
```

```
cgatgtggtc tggtcgggct gtcgttctag atcggagtag agtgctgttt caaactgtct    2580
agcggatcta ttagatttgg atctgcatgt gtgacatata tcttcgtagt taagatgatg    2640
catctgtatg tgtgacatgc ggatctatta gatttggatc tgtatgtgtg acatatatct    2700
tcgtagttga gatgatgcat ctgtatgtgt gacatatatc ttcgtagtta agattatgca    2760
tggaaatatc aatcctttag ataaggacgg gtatacttgt tgctgtgggt tttactggta    2820
cttcgataga tgcatataca tgatctaaca tgcttagata catgaagtaa catgctgcta    2880
cggtttaata attcttgagt tgatttttac tggtacttag atagatgtat atacatgctt    2940
agatacatga agtaacatgc tcctacagtt cctttaatca ttattgagta cctatatatt    3000
ctaataaatc agtatgtttt aaattatttt gattttactg gtacttagat agatgtatat    3060
atacatgctc aaacatgctt agatacatga agtaacatgc tgctacggtt tagtcattat    3120
tgagtgccta tatattctaa taaatcagta tgttttaaat tattttgatt ttactggtac    3180
ttagatagat gtatatatac atgctcaaac atgcttagat acatgaagta atatgctact    3240
acggtttaat tgttcttgag tacctatata ttctaataaa tcagtatgtt ttaaattatt    3300
tcgattttac tggtacttag atagatgtat atacatgctt agatacat gaagtaacat     3360 gctactacgg tttaattgtt cttgaatacc tatatattct aataaatcag tatgttttaa    3420
attatttcga ttttactggt acttagatag atgtatatat acatgctcga acatgcttag    3480
atacatgaag taacatgcta catatatatt ataataaatc agtatgtctt aaattatttt    3540
gattttactg gtacttagat agatgtatat acatgctcaa acatgcttag atacatgaag    3600
taacatgcta ctacggttta atcattattg agtacctata tattctaata aatcagtatg    3660
ttttcaattg ttttgatttt actggtactt agatatatgt atatatacat gctcgaacat    3720
gcttagatac gtgaagtaac atgctactat ggttaattgt tcttgagtac ctatatattc    3780
taataaatca gtatgtttta aattatttcg attttactgg tacttagata gatgtatata    3840
tacatgctcg aacatgctta gatacatgaa gtaacatgct actacggttt aatcgttctt    3900
gagtacctat atattctaat aaatcagtat gtcttaaatt atcttgattt tactggtact    3960
tagatagatg tatatacatg cttagataca tgaagtaaca tgctactatg atttaatcgt    4020
tcttgagtac ctatatattc taataaatca gtatgttttt aattattttg attttactgg    4080
tacttagata gatgtatata tacatgctcg aacatgctta gatacatgaa gtaacatgct    4140
actacggttt aatcattctt gagtacctat atattctaat aaatcagtat gttttaatt    4200 attttgatat tactggtact taacatgttt agatacatca tatagcatgc acatgctgct    4260
actgtttaat cattcgtgaa tacctatata ttctaatata tcagtatgtc ttctaattat    4320
tatgattttg atgtacttgt atggtggcat atgctgcagc tatgtgtaga ttttgaatac    4380
ccagtgtgat gagcatgcat ggcgccttca tagttcatat gctgtttatt tcctttgaga    4440
ctgttctttt ttgttgatag tcaccctgtt gtttggtgat tcttatccag atccagatct    4500
tcgagatcct aaaccatgtc cccggagcgc cgccggtgg agatccgccc ggccaccgcc    4560
gccgacatgg ccgccgtgtg cgacatcgtg aaccactaca tcgagacctc caccgtgaac    4620
ttccgcaccg agccgcagac cccgcaggag tggatcgacg acctcgagcg cctccaggac    4680
cgctacccgt ggctcgtggc cgaggtggag ggcgtggtgg ccggcatcgc ctacgccggc    4740
ccgtggaagg cccgcaacgc ctacgactgg accgtggagt ccaccgtgta cgtgtcccac    4800
cgccaccagc gcctcggcct cggctccacc ctctacaccc acctcctcaa gtctatggag    4860
gcccagggct tcaagtccgt ggtggccgtg atcggcctcc cgaacgaccc gtccgtgcgc    4920
```

```
ctccacgagg ccctcggcta caccgcccgc ggcaccctgc gcgccgccgg ctacaagcac    4980
ggcggctggc acgacgtggg cttctggcag cgcgacttcg agctgccggc cccgccgcgc    5040
ccggtgcgcc cggtgaccca gatttgagcc aaggttcaat taagctgctg ctgtacctgg    5100
gtatctgcgt cgtctggtgc cctctggtgt acctctatat ggatctcgtc gtctaataaa    5160
catctgtggt ttgtgtgtca tcaatcgtgg ttgtggcttc gttggtttaa tggacctgtt    5220
gtgtcctctg tgttgtaccc aaaactcttc tgcagcagta tggcttgaat ccttatgaag    5280
tttgatattt gaacttaaaa gtctgctcat tatgtttttt tctggttata tctcctaatt    5340
aactgcctgg gatcaaattt gattcgctgg tgtttattgg accctcccca ggttcttgct    5400
ttctaccgtt tcttgctgaa tgttaacttg attctgtcag gctcagtttc ccactatggc    5460
ttacagctta acgtgtttgg tttgttgaat gttaacttgg ttttgtcaag ctcagttttt    5520
tactctggct tacagcataa catgtttgac ttttggtttt gctgctttgt tattgggttc    5580
tgggtagttc ttgatgaatc caaaagatca tgtgcacagc catattatct atttaagcga    5640
tccaggttat tactatgaaa ggatgccttc tagctaagga gtagttaggt ttttcttca    5700 aggttaaatt ttctcgatgc tctagtgttc ctgtgaccat aatcataata attcctttga    5760
aagctctatg gtccctggaa gcagggcata caatgcaaga cagcaacttg atcacatcaa    5820
ctgaagtata cagggttctc ttaactcttg gtgacttcgg tttaatggac cggttgtact    5880
cgtgttctat ccgtaaccgt tgtgatgtct tgtgtgtttg gttgcgggat agctgggacc    5940
acgacgtttc cgtctaattc tgatggatag ctatagacgg cactgagatg gttatattat    6000
aacctctgat cctgaactct acgagatcgt ctcatccgtc attgccacca aatacaccat    6060
taaatta                                                              6067

<210> SEQ ID NO 5
<211> LENGTH: 6042
<212> TYPE: DNA
<213> ORGANISM: Artificial Sequence
<220> FEATURE:
<223> OTHER INFORMATION: derived from Streptomyces viridochromogenes and
      Zea mays

<400> SEQUENCE: 5
agctgcttgt ggggaccaga caaaaaagga atggtgcaga attgttaggc gcacctacca      60
aaagcaactt tgcctttatt gcaaagataa agcagattcc tctagtacaa gtggggaaca     120
aaataacgtg gaaagagct gtcctgacag cccactcact attgcgtttg acgaacgcag      180
tgacgaccac aaaactcgag acttttcaac aaagggtatt atccggaaac ctcctcggat     240
tccattgccc agctatctgt cactttattg tgaagatagt ggaaaaggaa ggtggctcct     300
acaaatgcca tcattgcgat aaaggaaagg ctatcgttga agatgcctct gccgacagtg     360
gtcccaaaga tggaccccca cccacgagga gcatcgtgga aaaagaagac gttccaacca     420
cgtcttcaaa gcaagtggat tgatgtgata tctccactga cgtaagggtt gacgaacaat     480
cccactatcc ttctgcctaa ttagctaacg gacccggaaa accaaaacaa cgaataagca     540
aactgcagga aaagtatgca gtggaaacca acccagattc ggacgatagg aaagtatcaa     600
gtgaatgatt tgccaggaaa aggagagggg taaaaggggg cgaagattta gaagatctaa     660
agcacaagaa ccagagatta gattgaacaa tagggaactt ggagcatcct tttttcttc     720 agggaaaaac tgaaaatcca aaccatgttg agcaaaaccg agtgggattg gaaaccaaaa     780
aacccgagat aagaaactc gagaaaaagc atgaaatcga aaccaacttc agtaaaacaa     840
```

```
aaggaggaca gaaaagaaag tcggaagcta taaagaatac attaacattc agtgaaacag    900
catgctgtct tcttcttttt ttatgcacaa cagagcatac atatatacct tcccaggctg    960
aggacttggc ggaggagagc cgcggatagg ttggcggtgc agacggtctg gacgggcccg   1020
aagacggaga cgaacagcgg gcccttcctg cccaggcacc acgcttggaa cgccaagcac   1080
gcgccaaccg cggccccgcc gaggacgacg atccccgcga caagcgtggc gtcgatcctg   1140
ggcgacccca agccgaggaa cctcccttcc aggacgagcc gtaggacggc ggtgagagag   1200
gcacccgtcg cggaggtggc gcagcacaag gtgagcagcg cggggaaggc ggcgagcgtg   1260
gcggcctgca ggacggtgac gagcgcgaag acggtgacgc cggcgacgag gcagcagcag   1320
ccgaggttcc agtcgtagga ggaagccgga ccaaaccggg caatgcaacc tgcagatgca   1380
ctagacggag gtaacgagga ggaggagaaa acagagcaag agcaggcgga gagaagatag   1440
agcaaaacac gagtgaggca cagcgtaagc actcggtaga agtctccaga ggcgaggtgc   1500
gcacaggaga acagatgagt aaagtcagcc aaggatgcac gatccaacgg ctacgaattt   1560
ttggagtgac gtggataggc tcaaaggcgc catttccatc cggctttata gtattttaaa   1620
aaaattcatt ttcctccctc tagtgtgtgc ggaggcgtga gcccgtttaa cggcgttgag   1680
aagtctaacg gacaccaacc acaaccagga accagcgccg gccgcgccgc cgagtgaagc   1740
agactgcata cggcacggcg cggcatctct ctggctgcct ctcgagagtt ccgcccccac   1800
cttcccgcgg tagcgtggtg gtttcgcttt ccgctgtcgg catccggaag ttgcgtggca   1860
gagtggacgg agacgaggcc gggtcctcca gctcctctca aacgtcacgg caccggcatc   1920
cggcagccag cgcggtcctt cccaaccact cgttcccaac ccatcccct tcctcgcccg   1980 ccgtcataaa tagccagccc catccccagc ttctttcccc aacctcatct tctctccttt   2040
tgctctgaac gcacacaccg cccggtctcc gatctccgat ccccgatccc ctcgtcgatc   2100
ctaggtacgg cgaccatcct accccccccc cccccccctc tctctctgcc ttctctagat   2160
cggcgatccg atccatgctt acttggttag ggcctgctaa ctatgttcat gtttgcgtta   2220
gatccgtgca tggacgcgat ctgtacacac cagacgcgtt ctgattgcta gctaactcgc   2280
cagtacctgg gaatcctggg atggctgtag ccggccccgc acgcagacgg gaccgatttc   2340
atgattctct attttttct ttgtttcgtt gcctagggtt tcgttcgatc gatccgcgtt   2400
attctttatt tccatatatt ctggtacgat gttgatacgg ttcgaccgtg ctgcttacgt   2460
tctgtgcgct tgtttgccgg gtcattttta ccttgccttt tttgtatggt ttggttgtgg   2520
cgatgtggtc tggtcgggct gtcgttctag atcggagtag agtgctgttt caaactgtct   2580
agcggatcta ttagatttgg atctgcatgt gtgacatata tcttcgtagt taagatgatg   2640
catctgtatg tgtgacatgc ggatctatta gatttggatc tgtatgtgtg acatatatct   2700
tcgtagttga gatgatgcat ctgtatgtgt gacatatatc ttcgtagtta agattatgca   2760
tggaaatatc aatcctttag ataaggacgg gtatacttgt tgctgtgggt tttactggta   2820
cttcgataga tgcatataca tgatctaaca tgcttagata catgaagtaa catgctgcta   2880
cggtttaata attcttgagt tgattttttac tggtacttag atagatgtat atacatgctt   2940
agatacatga agtaacatgc tcctacagtt cctttaatca ttattgagta cctatatatt   3000
ctaataaatc agtatgtttt aaattatttt gatttactg gtacttagat agatgtatat   3060
atacatgctc aaacatgctt agatacatga agtaacatgc tgctacggtt tagtcattat   3120
tgagtgccta tatattctaa taaatcagta tgttttaaat tattttgatt ttactggtac   3180
```

```
ttagatagat gtatatatac atgctcaaac atgcttagat acatgaagta atatgctact    3240
acggtttaat tgttcttgag tacctatata ttctaataaa tcagtatgtt ttaaattatt    3300
tcgattttac tggtacttag atagatgtat atatacatgc ttagatacat gaagtaacat    3360
gctactacgg tttaattgtt cttgaatacc tatatattct aataaatcag tatgttttaa    3420
attatttcga ttttactggt acttagatag atgtatatat acatgctcga acatgcttag    3480
atacatgaag taacatgcta catatatatt ataataaatc agtatgtctt aaattatttt    3540
gattttactg gtacttagat agatgtatat acatgctcaa acatgcttag atacatgaag    3600
taacatgcta ctacggttta atcattattg agtacctata tattctaata aatcagtatg    3660
ttttcaattg ttttgatttt actggtactt agatatatgt atatatacat gctcgaacat    3720
gcttagatac gtgaagtaac atgctactat ggttaattgt tcttgagtac ctatatattc    3780
taataaatca gtatgtttta aattatttcg attttactgg tacttagata gatgtatata    3840
tacatgctcg aacatgctta gatacatgaa gtaacatgct actacggttt aatcgttctt    3900
gagtacctat atattctaat aaatcagtat gtcttaaatt atcttgattt tactggtact    3960
tagatagatg tatatacatg cttagataca tgaagtaaca tgctactatg atttaatcgt    4020
tcttgagtac ctatatattc taataaatca gtatgttttt aattattttg attttactgg    4080
tacttagata gatgtatata tacatgctcg aacatgctta gatacatgaa gtaacatgct    4140
actacggttt aatcattctt gagtacctat atattctaat aaatcagtat gttttaattt    4200
attttgatat tactggtact aacatgtttt agatacatca tatagcatgc acatgctgct    4260 actgttaat cattcgtgaa tacctatata ttctaatata tcagtatgtc ttctaattat    4320
tatgattttg atgtacttgt atggtggcat atgctgcagc tatgtgtaga ttttgaatac    4380
ccagtgtgat gagcatgcat ggcgccttca tagttcatat gctgtttatt tcctttgaga    4440
ctgttctttt ttgttgatag tcaccctgtt gtttggtgat tcttatccag atgtccccgg    4500
agcgccgccc ggtggagatc cgcccggcca ccgccgccga catggccgcc gtgtgcgaca    4560
tcgtgaacca ctacatcgag acctccaccg tgaacttccg caccgagccg cagacccccgc   4620 aggagtggat cgacgacctc gagcgcctcc aggaccgcta cccgtggctc gtggccgagg    4680
tggagggcgt ggtggccggc atcgcctacg ccggcccgtg gaaggcccgc aacgcctacg    4740 actgaccgt ggagtccacc gtgtacgtgt cccaccgcca ccagcgcctc ggcctcggct    4800
ccaccctcta cacccacctc ctcaagtcta tggaggccca gggcttcaag tccgtggtgg    4860
ccgtgatcgg cctcccgaac gacccgtccg tgcgcctcca cgaggccctc ggctacaccg    4920
cccgcggcac cctgcgcgcc gccggctaca agcacggcgg ctggcacgac gtgggcttct    4980
ggcagcgcga cttcgagctg ccggccccgc cgcgcccggt gcgcccggtg acccagattt    5040
gagccaaggt tcaattaagc tgctgctgta cctgggtatc tgcgtcgtct ggtgccctct    5100
ggtgtacctc tatatggatc tcgtcgtcta ataaacatct gtggtttgtg tgtcatcaat    5160
cgtggttgtg gcttcgttgg tttaatggac ctgttgtgtc ctctgtgttg tacccaaaac    5220
tcttctgcag cagtatggct tgaatcctta tgaagtttga tatttgaact taaaagtctg    5280
ctcattatgt tttttttctgg ttatatctcc taattaactg cctgggatca aatttgattc    5340
gctggtgttt attggacccc tcccaggttc ttgctttcta ccgtttcttg ctgaatgtta    5400
acttgattct gtcaggctca gtttcccact atggcttaca gcttaacgtg tttggttttgt    5460 tgaatgttaa cttggttttg tcaagctcag ttttttactc tggcttacag cataacatgt    5520
ttgacttttg gttttgctgc tttgttattg ggttctgggt agttcttgat gaatccaaaa    5580
```

```
gatcatgtgc acagccatat tatctattta agcgatccag gttattacta tgaaaggatg    5640
ccttctagct aaggagtagt taggttttt cttcaaggtt aaatttctc gatgctctag     5700 tgttcctgtg accataatca taataattcc tttgaaagct ctatggtccc tggaagcagg    5760
gcatacaatg caagacagca acttgatcac atcaactgaa gtatacaggg ttctcttaac    5820
tcttggtgac ttcggtttaa tggaccggtt gtactcgtgt tctatccgta accgttgtga    5880
tgtcttgtgt gtttggttgc gggatagctg ggaccacgac gtttccgtct aattctgatg    5940
gatagctata gacggcactg gatggttat attataaccct ctgatcctga actctacgag    6000
atcgtctcat ccgtcattgc caccaaatac accattaaat ta                       6042
```

<210> SEQ ID NO 6
<211> LENGTH: 552
<212> TYPE: DNA
<213> ORGANISM: Artificial Sequence
<220> FEATURE:
<223> OTHER INFORMATION: derived from Streptomyces viridochromogenes

<400> SEQUENCE: 6

```
atgagcccg aaaggaggcc cgtcgaaatc aggcccgcca ccgccgccga catggccgcc      60
gtctgcgaca tcgtgaacca ctacatcgaa accagcaccg tcaactttag gaccgaaccc    120
cagacccccc aggaatggat cgacgacctg gaaaggctgc aggacagata ccctggctg    180 gtcgccgaag tcgaaggcgt cgtcgccggc atagcctacg ccggcccctg gaaggccagg    240
aacgcctacg actggaccgt cgaaagcacc gtctacgtca gccacaggca ccagaggctg    300
ggcctgggca gcaccctgta cacccacctg ctgaagagca tggaagccca gggcttcaag    360
agcgtcgtcg ccgtcatcgg cctgcccaac gaccccagcg tcaggctgca cgaagccctg    420
ggctacaccc caggggcac cctgagggcc gccggctaca gcacggcgg ctggcacgac     480 gtcggcttct ggcagaggga cttcgaactg cccgccccc ccaggcccgt caggcccgtc     540
acccagattt ga                                                        552
```

<210> SEQ ID NO 7
<211> LENGTH: 5552
<212> TYPE: DNA
<213> ORGANISM: Artificial Sequence
<220> FEATURE:
<223> OTHER INFORMATION: derived from Streptomyces viridochromogenes and
      Zea mays

<400> SEQUENCE: 7

```
ggaaaaccaa acaacgaat aagcaaactg caggaaaagt atgcagtgga aaccaaccca     60
gattcggacg ataggaaagt atcaagtgaa tgatttgcca ggaaaaggag aggggtaaaa    120
aggggcgaag atttagaaga tctaaagcac aagaaccaga gattagattg aacaataggg    180
aacttggagc atcctttttt tcttcaggga aaaactgaaa atccaaacca tgttgagcaa    240
aaccgagtgg gattggaaac caaaaaaccc gagataaaga aactcgagaa aaagcatgaa    300
atcgaaacca acttcagtaa aacaaaagga ggacagaaaa gaaagtcgga agctataaag    360
aatacattaa cattcagtga aacagcatgc tgtcttcttc ttttttatg cacaacagag    420 catacatata taccttccca ggctgaggac ttggcggagg agagccgcgg ataggttggc    480
ggtgcagacg gtcggacgg gcccgaagac ggagacgaac agcgggccct tcctgcccag    540
gcaccacgct tggaacgcca agcacgcgcc aaccgcggcc ccgccgagga cgacgatccc    600
cgcgacaagc gtggcgtcga tcctgggcga ccccaagccg aggaacctcc cttccaggac    660
```

```
gagccgtagg acggcggtga gagaggcacc cgtcgcggag gtggcgcagc acaaggtgag    720
cagcgcgggg aaggcggcga gcgtggcggc ctgcaggacg tgacgagcg cgaagacggt    780 gacgccggcg acgaggcagc agcagccgag gttccagtcg taggaggaag ccggaccaaa    840
ccgggcaatg caacctgcag atgcactaga cggaggtaac gaggaggagg agaaaacaga    900
gcaagagcag gcggagagaa gatagagcaa acacgagtg aggcacagcg taagcactcg    960
gtagaagtct ccagaggcga ggtgcgcaca ggagaacaga tgagtaaagt cagccaagga   1020
tgcacgatcc aacggctacg aattttttgga gtgacgtgga taggctcaaa ggcgccattt   1080
ccatccggct ttatagtatt ttaaaaaaat tcattttcct ccctctagtg tgtgcggagg   1140
cgtgagcccg tttaacggcg ttgagaagtc taacggacac caaccacaac caggaaccag   1200
cgccggccgc gccgccgagt gaagcagact gcatacggca cggcgcggca tctctctggc   1260
tgcctctcga gagttccgcc cccaccttcc cgcggtagcg tggtggtttc gctttccgct   1320
gtcggcatcc ggaagttgcg tggcagagtg gacggagacg aggccgggtc ctccagctcc   1380
tctcaaacgt cacggcaccg gcatccggca gccagcgcgg tccttcccaa ccactcgttc   1440
ccaacccatc cccottcctc gcccgccgtc ataaatagcc agcccatcc ccagcttctt   1500 tccccaacct catcttctct cctttttgctc tgaacgcaca caccgcccgg tctccgatct   1560
ccgatccccg atccctcgt cgatcctagg tacggcgacc atcctacccc cccccccccc   1620
ccctctctct ctgccttctc tagatcggcg atccgatcca tgcttacttg gttagggcct   1680
gctaactatg ttcatgtttg cgttagatcc gtgcatggac gcgatctgta cacaccagac   1740
gcgttctgat tgctagctaa ctcgccagta cctgggaatc ctgggatggc tgtagccggc   1800
cccgcacgca gacgggaccg atttcatgat tctctatttt tttctttgtt tcgttgccta   1860
gggtttcgtt cgatcgatcc gcgttattct ttatttccat atattctggt acgatgttga   1920
tacggttcga ccgtgctgct tacgttctgt gcgcttgttt gccgggtcat ttttaccttg   1980
ccttttttgt atggtttggt tgtggcgatg tggtctggtc gggctgtcgt tctagatcgg   2040
agtagagtgc tgtttcaaac tgtctagcgg atctattaga tttggatctg catgtgtgac   2100
atatatcttc gtagttaaga tgatgcatct gtatgtgtga catgcggatc tattagattt   2160
ggatctgtat gtgtgacata tatcttcgta gttgagatga tgcatctgta tgtgtgacat   2220
atatcttcgt agttaagatt atgcatggaa atatcaatcc tttagataag gacgggtata   2280
cttgttgctg tgggttttac tggtacttcg atagatgcat atacatgatc taacatgctt   2340
agatacatga agtaacatgc tgctacggtt taataattct tgagttgatt tttactggta   2400
cttagataga tgtatataca tgcttagata catgaagtaa catgctccta cagttccttt   2460
aatcattatt gagtacctat atattctaat aaatcagtat gttttaaatt attttgattt   2520
tactggtact tagatagatg tatatataca tgctcaaaca tgcttagata catgaagtaa   2580
catgctgcta cggtttagtc attattgagt gcctatatat tctaataaat cagtatgttt   2640
taaattattt tgattttact ggtacttaga tagatgtata tatacatgct caaacatgct   2700
tagatacatg aagtaaatatg ctactacggt ttaattgttc ttgagtacct atatattcta   2760
ataaatcagt atgttttaaa ttatttcgat tttactggta cttagataga tgtatatata   2820
catgcttaga tacatgaagt aacatgctac tacggtttaa ttgttcttga atacctatat   2880
attctaataa atcagtatgt tttaaattat ttcgattttta ctggtactta gatagatgta   2940
tatatacatg ctcgaacatg cttagataca tgaagtaaca tgctacatat atattataat   3000
```

```
aaatcagtat gtcttaaatt attttgattt tactggtact tagatagatg tatatacatg    3060
ctcaaacatg cttagataca tgaagtaaca tgctactacg gtttaatcat tattgagtac    3120
ctatatattc taataaatca gtatgttttc aattgttttg attttactgg tacttagata    3180
tatgtatata tacatgctcg aacatgctta gatacgtgaa gtaacatgct actatggtta    3240
attgttcttg agtacctata tattctaata aatcagtatg ttttaaatta tttcgatttt    3300
actggtactt agatagatgt atatatacat gctcgaacat gcttagatac atgaagtaac    3360
atgctactac ggtttaatcg ttcttgagta cctatatatt ctaataaatc agtatgtctt    3420
aaattatctt gatttactg gtacttagat agatgtatat acatgcttag atacatgaag    3480
taacatgcta ctatgattta atcgttcttg agtacctata tattctaata aatcagtatg    3540
tttttaatta ttttgatttt actggtactt agatagatgt atatatacat gctcgaacat    3600
gcttagatac atgaagtaac atgctactac ggtttaatca ttcttgagta cctatatatt    3660
ctaataaatc agtatgtttt taattatttt gatattactg gtacttaaca tgtttagata    3720
catcatatag catgcacatg ctgctactgt ttaatcattc gtgaatacct atatattcta    3780
atatatcagt atgtcttcta attattatga ttttgatgta cttgtatggt ggcatatgct    3840
gcagctatgt gtagattttg aatacccagt gtgatgagca tgcatggcgc cttcatagtt    3900
catatgctgt ttatttcctt tgagactgtt ctttttttgtt gatagtcacc ctgttgtttg    3960
gtgattctta tccagatcca gatcttcgag atcctaaacc atgagcccg aaaggaggcc    4020
cgtcgaaatc aggcccgcca ccgccgccga catggccgcc gtctgcgaca tcgtgaacca    4080
ctacatcgaa accagcaccg tcaactttag gaccgaaccc cagacccccc aggaatggat    4140
cgacgacctg gaaaggctgc aggacagata ccctggctg gtcgccgaag tcgaaggcgt    4200
cgtcgccggc atagcctacg ccggcccctg gaaggccagg aacgcctacg actgaccgt    4260
cgaaagcacc gtctacgtca gccacaggca ccagaggctg ggcctgggca gcaccctgta    4320
cacccacctg ctgaagagca tggaagccca gggcttcaag agcgtcgtcg ccgtcatcgg    4380
cctgcccaac gaccccagcg tcaggctgca cgaagccctg gctacaccg ccaggggcac    4440
cctgagggcc gccggctaca agcacggcgg ctggcacgac gtcggcttct ggcagagga    4500
cttcgaactg cccgcccccc ccaggcccgt caggcccgtc acccagattt gagccaaggt    4560
tcaattaagc tgctgctgta cctgggtatc tgcgtcgtct ggtgccctct ggtgtacctc    4620
tatatggatc tcgtcgtcta ataaacatct gtggtttgtg tgtcatcaat cgtggttgtg    4680
gcttcgttgg tttaatggac ctgttgtgtc ctctgtgttg tacccaaaac tcttctgcag    4740
cagtatggct tgaatcctta tgaagtttga tatttgaact taaaagtctg ctcattatgt    4800
ttttttctgg ttatatctcc taattaactg cctgggatca aatttgattc gctggtgttt    4860
attggacccc tcccaggttc ttgctttcta ccgtttcttg ctgaatgtta acttgattct    4920
gtcaggctca gtttcccact atggcttaca gcttaacgtg tttggtttgt tgaatgttaa    4980
cttggttttg tcaagctcag ttttttactc tggcttacag cataacatgt ttgactttg    5040
gttttgctgc tttgttattg ggttctgggt agttcttgat gaatccaaaa gatcatgtgc    5100
acagccatat tatctattta agcgatccag gttattacta tgaaaggatg ccttctagct    5160
aaggagtagt taggttttt cttcaaggtt aaattttctc gatgctctag tgttcctgtg    5220
accataatca taataattcc tttgaaagct ctatggtccc tggaagcagg gcatacaatg    5280
caagacagca acttgatcac atcaactgaa gtatacaggg ttctcttaac tcttggtgac    5340
ttcggtttaa tggaccggtt gtactcgtgt tctatccgta accgttgtga tgtcttgtgt    5400
```

```
gtttggttgc gggatagctg ggaccacgac gtttccgtct aattctgatg gatagctata      5460
gacggcactg agatggttat attataacct ctgatcctga actctacgag atcgtctcat      5520
ccgtcattgc caccaaatac accattaaat ta                                    5552

<210> SEQ ID NO 8
<211> LENGTH: 5527
<212> TYPE: DNA
<213> ORGANISM: Artificial Sequence
<220> FEATURE:
<223> OTHER INFORMATION: derived from Streptomyces viridochromogenes and
      Zea mays

<400> SEQUENCE: 8
ggaaaaccaa acaacgaat aagcaaactg caggaaaagt atgcagtgga aaccaaccca         60
gattcggacg ataggaaagt atcaagtgaa tgatttgcca ggaaaaggag aggggtaaaa       120
aggggcgaag atttagaaga tctaaagcac aagaaccaga gattagattg aacaataggg       180
aacttggagc atccttttt tcttcaggga aaaactgaaa atccaaacca tgttgagcaa        240
aaccgagtgg gattggaaac caaaaaaccc gagataaaga aactcgagaa aaagcatgaa       300
atcgaaacca acttcagtaa aacaaaagga ggacagaaaa gaaagtcgga agctataaag       360
aatacattaa cattcagtga aacagcatgc tgtcttcttc ttttttttatg cacaacagag     420 catacatata taccttccca ggctgaggac ttggcggagg agagccgcgg ataggttggc      480
ggtgcagacg gtctggacgg gcccgaagac ggagacgaac agcgggccct tcctgcccag      540
gcaccacgct tggaacgcca agcacgcgcc aaccgcggcc ccgccgagga cgacgatccc      600
cgcgacaagc gtggcgtcga tcctgggcga ccccaagccg aggaacctcc cttccaggac     660
gagccgtagg acggcggtga gagaggcacc cgtcgcggag gtggcgcagc acaaggtgag      720
cagcgcgggg aaggcggcga gcgtggcggc ctgcaggacg gtgacgagcg cgaagacggt      780
gacgccggcg acgaggcagc agcagccgag gttccagtcg taggaggaag ccggaccaaa      840
ccgggcaatg caacctgcag atgcactaga cggaggtaac gaggaggagg agaaaacaga     900
gcaagagcag gcgagagaa gatagagcaa aacacgagtg aggcacagcg taagcactcg       960
gtagaagtct ccagaggcga ggtgcgcaca ggagaacaga tgagtaaagt cagccaagga     1020
tgcacgatcc aacggctacg aattttttgga gtgacgtgga taggctcaaa ggcgccattt    1080
ccatccggct ttatagtatt ttaaaaaaat tcattttcct ccctctagtg tgtgcggagg     1140
cgtgagcccg tttaacggcg ttgagaagtc taacggacac caaccacaac caggaaccag     1200
cgccggccgc gccgccgagt gaagcagact gcatacggca cggcgcggca tctctctggc     1260
tgcctctcga gagttccgcc ccacccttcc cgcggtagcg tggtggtttc gctttccgct    1320
gtcggcatcc ggaagttgcg tggcagagtg gacggagacg aggccgggtc ctccagctcc    1380
tctcaaacgt cacggcaccg gcatccggca gccagcgcgg tccttcccaa ccactcgttc    1440
ccaacccatc ccccttcctc gcccgccgtc ataaatagcc agcccatcc ccagcttctt     1500 tccccaacct catcttctct ccttttgctc tgaacgcaca caccgccgg tctccgatct     1560 ccgatcccg atcccctcgt cgatcctagg tacggcgacc atcctacccc ccccccccc     1620 ccctctctct ctgccttctc tagatcggcg atccgatcca tgcttacttg gttagggcct   1680
gctaactatg ttcatgtttg cgttagatcc gtgcatggac gcgatctgta cacaccagac    1740
gcgttctgat tgctagctaa ctcgccagta cctgggaatc ctgggatggc tgtagccggc    1800
cccgcacgca gacgggaccg atttcatgat tctctatttt tttctttgtt tcgttgccta   1860
```

```
gggtttcgtt cgatcgatcc gcgttattct ttatttccat atattctggt acgatgttga    1920
tacggttcga ccgtgctgct tacgttctgt gcgcttgttt gccgggtcat ttttaccttg    1980 cctttttgt atggtttggt tgtggcgatg tggtctggtc gggctgtcgt tctagatcgg     2040
agtagagtgc tgtttcaaac tgtctagcgg atctattaga tttggatctg catgtgtgac   2100
atatatcttc gtagttaaga tgatgcatct gtatgtgtga catgcggatc tattagattt   2160
ggatctgtat gtgtgacata tatcttcgta gttgagatga tgcatctgta tgtgtgacat   2220
atatcttcgt agttaagatt atgcatggaa atatcaatcc tttagataag gacgggtata   2280
cttgttgctg tgggttttac tggtacttcg atagatgcat atacatgatc taacatgctt   2340
agatacatga agtaacatgc tgctacggtt taataattct tgagttgatt tttactggta   2400
cttagataga tgtatataca tgcttagata catgaagtaa catgctccta cagttccttt   2460
aatcattatt gagtacctat atattctaat aaatcagtat gttttaaatt attttgattt   2520
tactggtact tagatagatg tatatataca tgctcaaaca tgcttagata catgaagtaa   2580
catgctgcta cggtttagtc attattgagt gcctatatat tctaataaat cagtatgttt   2640
taaattattt tgattttact ggtacttaga tagatgtata tacatgct caaacatgct    2700 tagatacatg aagtaatatg ctactacggt ttaattgttc ttgagtacct atatattcta   2760
ataaatcagt atgttttaaa ttatttcgat tttactggta cttagataga tgtatatata   2820
catgcttaga tacatgaagt aacatgctac tacggtttaa ttgttcttga atacctatat   2880
attctaataa atcagtatgt tttaaattat ttcgatttta ctggtactta gatagatgta   2940 tatacatg ctcgaacatg cttagataca tgaagtaaca tgctacatat atattataat   3000
aaatcagtat gtcttaaatt attttgattt tactggtact tagatagatg tatatacatg   3060
ctcaaacatg cttagataca tgaagtaaca tgctactacg gtttaatcat tattgagtac   3120
ctatatattc taataaatca gtatgttttc aattgttttg attttactgg tacttagata   3180
tatgtatata tacatgctcg aacatgctta gatacgtgaa gtaacatgct actatggtta   3240
attgttcttg agtacctata tattctaata atcagtatg ttttaaatta tttcgatttt   3300
actggtactt agatagatgt atatatacat gctcgaacat gcttagatac atgaagtaac   3360
atgctactac ggtttaatcg ttcttgagta cctatatatt ctaataaatc agtatgtctt   3420
aaattatctt gattttactg gtacttagat agatgtatat acatgcttag atacatgaag   3480
taacatgcta ctatgattta atcgttcttg agtacctata tattctaata atcagtatg   3540 tttttaatta ttttgatttt actggtactt agatagatgt atatatacat gctcgaacat   3600
gcttagatac atgaagtaac atgctactac ggtttaatca ttcttgagta cctatatatt   3660
ctaataaatc agtatgtttt taattatttt gatattactg gtacttaaca tgtttagata   3720
catcatatag catgcacatg ctgctactgt ttaatcattc gtgaatacct atatattcta   3780
atatatcagt atgtcttcta attattatga ttttgatgta cttgtatggt ggcatatgct   3840
gcagctatgt gtagattttg aatacccagt gtgatgagca tgcatggcgc cttcatagtt   3900
catatgctgt ttatttcctt tgagactgtt cttttttgtt gatagtcacc ctgttgtttg   3960
gtgattctta tccagatgag ccccgaaagg aggcccgtcg aaatcaggcc cgccaccgcc   4020
gccgacatgg ccgccgtctg cgacatcgtg aaccactaca tcgaaaccag caccgtcaac   4080
tttaggaccg aaccccagac cccccaggaa tggatcgacg acctggaaag gctgcaggac   4140
agatacccct ggctggtcgc cgaagtcgaa ggcgtcgtcg ccggcatagc ctacgccggc   4200
```

```
ccctggaagg ccaggaacgc ctacgactgg accgtcgaaa gcaccgtcta cgtcagccac    4260
aggcaccaga ggctgggcct gggcagcacc ctgtacaccc acctgctgaa gagcatggaa    4320
gcccagggct tcaagagcgt cgtcgccgtc atcggcctgc ccaacgaccc cagcgtcagg    4380
ctgcacgaag ccctgggcta caccgccagg ggcaccctga gggccgccgg ctacaagcac    4440
ggcggctggc acgacgtcgg cttctggcag agggacttcg aactgcccgc ccccccagg    4500 cccgtcaggc ccgtcaccca gatttgagcc aaggttcaat taagctgctg ctgtacctgg    4560
gtatctgcgt cgtctggtgc cctctggtgt acctctatat ggatctcgtc gtctaataaa    4620
catctgtggt ttgtgtgtca tcaatcgtgg ttgtggcttc gttggtttaa tggacctgtt    4680
gtgtcctctg tgttgtaccc aaaactcttc tgcagcagta tggcttgaat ccttatgaag    4740
tttgatattt gaacttaaaa gtctgctcat tatgttttt tctggttata tctcctaatt     4800
aactgcctgg gatcaaattt gattcgctgg tgtttattgg accctccca ggttcttgct     4860 ttctaccgtt tcttgctgaa tgttaacttg attctgtcag gctcagtttc ccactatggc    4920
ttacagctta acgtgtttgg tttgttgaat gttaacttgg ttttgtcaag ctcagttttt    4980
tactctggct tacagcataa catgtttgac ttttggtttt gctgctttgt tattgggttc    5040
tgggtagttc ttgatgaatc caaaagatca tgtgcacagc catattatct atttaagcga    5100
tccaggttat tactatgaaa ggatgccttc tagctaagga gtagttaggt ttttcttca     5160 aggttaaatt ttctcgatgc tctagtgttc ctgtgaccat aatcataata attccctttga   5220 aagctctatg gtccctggaa gcagggcata caatgcaaga cagcaacttg atcacatcaa    5280
ctgaagtata cagggttctc ttaactcttg gtgacttcgg tttaatggac cggttgtact    5340
cgtgttctat ccgtaaccgt tgtgatgtct tgtgtgtttg gttgcgggat agctgggacc    5400
acgacgtttc cgtctaattc tgatggatag ctatagacgg cactgagatg gttatattat    5460
aacctctgat cctgaactct acgagatcgt ctcatccgtc attgccacca aatacaccat    5520
taaatta                                                              5527
```

<210> SEQ ID NO 9
<211> LENGTH: 6067
<212> TYPE: DNA
<213> ORGANISM: Artificial Sequence
<220> FEATURE:
<223> OTHER INFORMATION: derived from Streptomyces viridochromogenes and
      Zea mays

<400> SEQUENCE: 9

```
agctgcttgt ggggaccaga caaaaaagga atggtgcaga attgttaggc gcacctacca     60
aaagcaactt tgcctttatt gcaaagataa agcagattcc tctagtacaa gtggggaaca    120
aaataacgtg gaaagagct gtcctgacag cccactcact attgcgtttg acgaacgcag     180
tgacgaccac aaaactcgag acttttcaac aaagggtatt atccggaaac ctcctcggat    240
tccattgccc agctatctgt cactttattg tgaagatagt ggaaaaggaa ggtggctcct    300
acaaatgcca tcattgcgat aaaggaaagg ctatcgttga agatgcctct gccgacagtg    360
gtcccaaaga tggaccccca cccacgagga gcatcgtgga aaaagaagac gttccaacca    420
cgtcttcaaa gcaagtggat tgatgtgata tctccactga cgtaagggtt gacgaacaat    480
cccactatcc ttctgcctaa ttagctaacg gacccggaaa accaaaacaa cgaataagca    540
aactgcagga aaagtatgca gtggaaacca acccagattc ggacgatagg aaagtatcaa    600
gtgaatgatt tgccaggaaa aggagagggg taaaaagggg cgaagattta gaagatctaa    660
```

-continued

```
agcacaagaa ccagagatta gattgaacaa tagggaactt ggagcatcct ttttttcttc      720
agggaaaaac tgaaaatcca aaccatgttg agcaaaaccg agtgggattg gaaaccaaaa      780
aacccgagat aaagaaactc gagaaaaagc atgaaatcga aaccaacttc agtaaaacaa      840
aaggaggaca gaaaagaaag tcggaagcta taaagaatac attaacattc agtgaaacag      900
catgctgtct tcttcttttt ttatgcacaa cagagcatac atatatacct tcccaggctg      960
aggacttggc ggaggagagc cgcggatagg ttggcggtgc agacggtctg gacgggcccg     1020
aagacggaga cgaacagcgg gcccttcctg cccaggcacc acgcttggaa cgccaagcac     1080
gcgccaaccg cggccccgcc gaggacgacg atccccgcga caagcgtggc gtcgatcctg     1140
ggcgacccca agccgaggaa cctcccttcc aggacgagcc gtaggacggc ggtgagagag     1200
gcacccgtcg cggaggtggc gcagcacaag gtgagcagcg cggggaaggc ggcgagcgtg     1260
gcggcctgca ggacggtgac gagcgcgaag acggtgacgc cggcgacgag gcagcagcag     1320
ccgaggttcc agtcgtagga ggaagccgga ccaaaccggg caatgcaacc tgcagatgca     1380
ctagacggag gtaacgagga ggaggagaaa acagagcaag agcaggcgga gagaagatag     1440
agcaaaacac gagtgaggca cagcgtaagc actcggtaga agtctccaga ggcgaggtgc     1500
gcacaggaga acagatgagt aaagtcagcc aaggatgcac gatccaacgg ctacgaattt     1560
ttggagtgac gtggataggc tcaaaggcgc catttccatc cggctttata gtattttaaa     1620
aaaattcatt ttcctccctc tagtgtgtgc ggaggcgtga gcccgtttaa cggcgttgag     1680
aagtctaacg gacaccaacc acaaccagga accagcgccg gccgcgccgc cgagtgaagc     1740
agactgcata cggcacggcg cggcatctct ctggctgcct ctcgagagtt ccgcccccac     1800
cttcccgcgg tagcgtggtg gtttcgcttt ccgctgtcgg catccggaag ttgcgtggca     1860
gagtggacgg agacgaggcc gggtcctcca gctcctctca aacgtcacgg caccggcatc     1920
cggcagccag cgcggtcctt cccaaccact cgttcccaac ccatccccct tcctcgcccg     1980
ccgtcataaa tagccagccc catccccagc ttctttcccc aacctcatct tctctccttt     2040
tgctctgaac gcacacaccg cccggtctcc gatctccgat ccccgatccc ctcgtcgatc     2100
ctaggtacgg cgaccatcct accccccccc ccccccctc tctctctgcc ttctctagat     2160
cggcgatccg atccatgctt acttggttag ggcctgctaa ctatgttcat gtttgcgtta     2220
gatccgtgca tggacgcgat ctgtacacac cagacgcgtt ctgattgcta gctaactcgc     2280
cagtacctgg gaatcctggg atggctgtag ccggccccgc acgcagacgg gaccgatttc     2340
atgattctct atttttttct ttgtttcgtt gcctagggtt tcgttcgatc gatccgcgtt     2400
attctttatt tccatatatt ctggtacgat gttgatacgg ttcgaccgtg ctgcttacgt     2460
tctgtgcgct tgtttgccgg gtcatttttta ccttgccttt tttgtatggt ttggttgtgg     2520
cgatgtggtc tggtcgggct gtcgttctag atcggagtag agtgctgttt caaactgtct     2580
agcggatcta ttagatttgg atctgcatgt gtgacatata tcttcgtagt taagatgatg     2640
catctgtatg tgtgacatgc ggatctatta gatttggatc tgtatgtgtg acatatatct     2700
tcgtagttga gatgatgcat ctgtatgtgt gacatatatc ttcgtagtta agattatgca     2760
tggaaatatc aatcctttag ataaggacgg gtatacttgt tgctgtgggt tttactggta     2820
cttcgataga tgcatataca tgatctaaca tgcttagata catgaagtaa catgctgcta     2880
cggtttaata attcttgagt tgattttttac tggtacttag atagatgtat atacatgctt     2940
agatacatga agtaacatgc tcctacagtt cctttaatca ttattgagta cctatatatt     3000
ctaataaatc agtatgtttt aaattatttt gattttactg gtacttagat agatgtatat     3060
```

```
atacatgctc aaacatgctt agatacatga agtaacatgc tgctacggtt tagtcattat   3120
tgagtgccta tatattctaa taaatcagta tgttttaaat tattttgatt ttactggtac   3180
ttagatagat gtatatatac atgctcaaac atgcttagat acatgaagta atatgctact   3240
acggtttaat tgttcttgag tacctatata ttctaataaa tcagtatgtt ttaaattatt   3300
tcgattttac tggtacttag atagatgtat atacatgc ttagatacat gaagtaacat    3360
gctactacgg tttaattgtt cttgaatacc tatatattct aataaatcag tatgttttaa   3420
attatttcga ttttactggt acttagatag atgtatatat acatgctcga acatgcttag   3480
atacatgaag taacatgcta catatatatt ataataaatc agtatgtctt aaattatttt   3540
gattttactg gtacttagat agatgtatat acatgctcaa acatgcttag atacatgaag   3600
taacatgcta ctacggttta atcattattg agtacctata tattctaata aatcagtatg   3660
ttttcaattg ttttgatttt actggtactt agatatatgt atatatacat gctcgaacat   3720
gcttagatac gtgaagtaac atgctactat ggttaattgt tcttgagtac ctatatattc   3780
taataaatca gtatgtttta aattatttcg attttactgg tacttagata gatgtatata   3840
tacatgctcg aacatgctta gatacatgaa gtaacatgct actacggttt aatcgttctt   3900
gagtacctat atattctaat aaatcagtat gtcttaaatt atcttgattt tactggtact   3960
tagatagatg tatatacatg cttagataca tgaagtaaca tgctactatg atttaatcgt   4020
tcttgagtac ctatatattc taataaatca gtatgttttt aattattttg attttactgg   4080
tacttagata gatgtatata tacatgctcg aacatgctta gatacatgaa gtaacatgct   4140
actacggttt aatcattctt gagtacctat atattctaat aaatcagtat gttttaatt   4200
attttgatat tactggtact taacatgttt agatacatca tatagcatgc acatgctgct   4260
actgtttaat cattcgtgaa tacctatata ttctaatata tcagtatgtc ttctaattat   4320
tatgattttg atgtacttgt atggtggcat atgctgcagc tatgtgtaga ttttgaatac   4380
ccagtgtgat gagcatgcat ggcgccttca tagttcatat gctgtttatt tcctttgaga   4440
ctgttctttt ttgttgatag tcaccctgtt gtttggtgat tcttatccag atccagatct   4500
tcgagatcct aaaccatgag ccccgaaagg aggcccgtcg aaatcaggcc cgccaccgcc   4560
gccgacatgg ccgccgtctg cgacatcgtg aaccactaca tcgaaaccag caccgtcaac   4620
tttaggaccg aaccccagac cccccaggaa tggatcgacg acctggaaag gctgcaggac   4680
agataccct ggctggtcgc cgaagtcgaa ggcgtcgtcg ccggcatagc ctacgccggc   4740
ccctggaagg ccaggaacgc ctacgactgg accgtcgaaa gcaccgtcta cgtcagccac   4800
aggcaccaga ggctgggcct gggcagcacc ctgtacaccc acctgctgaa gagcatggaa   4860
gcccagggct tcaagagcgt cgtcgccgtc atcggcctgc ccaacgaccc cagcgtcagg   4920
ctgcacgaag ccctgggcta caccgccagg ggcaccctga gggccgccgg ctacaagcac   4980
ggcggctgg acgacgtcgg cttctggcag agggacttcg aactgcccgc ccccccagg   5040
cccgtcaggc ccgtcaccca gatttgagcc aaggttcaat taagctgctg ctgtacctgg   5100
gtatctgcgt cgtctggtgc cctctggtgt acctctatat ggatctcgtc gtctaataaa   5160
catctgtggt ttgtgtgtca tcaatcgtgg ttgtggcttc gttggtttaa tggacctgtt   5220
gtgtcctctg tgttgtaccc aaaactcttc tgcagcagta tggcttgaat ccttatgaag   5280
tttgatattt gaacttaaaa gtctgctcat tatgtttttt tctggttata tctcctaatt   5340
aactgcctgg gatcaaattt gattcgctgg tgtttattgg acccctccca ggttcttgct   5400
```

```
ttctaccgtt tcttgctgaa tgttaacttg attctgtcag gctcagtttc ccactatggc   5460
ttacagctta acgtgtttgg tttgttgaat gttaacttgg ttttgtcaag ctcagttttt   5520
tactctggct tacagcataa catgtttgac ttttggtttt gctgctttgt tattgggttc   5580
tgggtagttc ttgatgaatc caaaagatca tgtgcacagc catattatct atttaagcga   5640
tccaggttat tactatgaaa ggatgccttc tagctaagga gtagttaggt ttttttcttca  5700 aggttaaatt ttctcgatgc tctagtgttc ctgtgaccat aatcataata attcctttga   5760
aagctctatg gtccctggaa gcagggcata caatgcaaga cagcaacttg atcacatcaa   5820
ctgaagtata cagggttctc ttaactcttg gtgacttcgg tttaatggac cggttgtact   5880
cgtgttctat ccgtaaccgt tgtgatgtct tgtgtgtttg gttgcgggat agctgggacc   5940
acgacgtttc cgtctaattc tgatggatag ctatagacgg cactgagatg gttatattat   6000
aacctctgat cctgaactct acgagatcgt ctcatccgtc attgccacca aatacaccat   6060
taaatta                                                             6067

<210> SEQ ID NO 10
<211> LENGTH: 6042
<212> TYPE: DNA
<213> ORGANISM: Artificial Sequence
<220> FEATURE:
<223> OTHER INFORMATION: derived from Streptomyces viridochromogenes and
      Zea mays

<400> SEQUENCE: 10
agctgcttgt ggggaccaga caaaaaagga atggtgcaga attgttaggc gcacctacca     60
aaagcaactt tgcctttatt gcaaagataa agcagattcc tctagtacaa gtggggaaca   120
aaataacgtg gaaagagct gtcctgacag cccactcact attgcgtttg acgaacgcag    180
tgacgaccac aaaactcgag acttttcaac aaagggtatt atccggaaac ctcctcggat   240
tccattgccc agctatctgt cactttattg tgaagatagt ggaaaaggaa ggtggctcct   300
acaaatgcca tcattgcgat aaaggaaagg ctatcgttga gatgcctct gccgacagtg   360 gtcccaaaga tggaccccca cccacgagga gcatcgtgga aaaagaagac gttccaacca   420
cgtcttcaaa gcaagtggat tgatgtgata tctccactga cgtaagggtt gacgaacaat   480
cccactatcc ttctgcctaa ttagctaacg gaccccgaaa accaaaacaa cgaataagca   540
aactgcagga aaagtatgca gtggaaacca acccagattc ggacgatagg aaagtatcaa   600
gtgaatgatt tgccaggaaa aggagagggg taaaagggg cgaagattta gaagatctaa    660
agcacaagaa ccagagatta gattgaacaa tagggaactt ggagcatcct ttttttcttc   720
agggaaaaac tgaaaatcca aaccatgttg agcaaaaccg agtgggattg gaaaccaaaa   780
aacccgagat aaagaaactc gagaaaaagc atgaaatcga aaccaacttc agtaaaacaa   840
aaggaggaca gaaaagaaag tcggaagcta taagaatac attaacattc agtgaaacag    900
catgctgtct tcttcttttt ttatgcacaa cagagcatac atatatacct tcccaggctg   960
aggacttggc ggaggagagc cgcggatagg ttggcggtgc agacggtctg gacgggcccg  1020
aagacggaga cgaacagcgg gcccttcctg cccaggcacc acgcttggaa cgccaagcac  1080
gcgccaaccg cggccccgcc gaggacgacg atccccgcga caagcgtggc gtcgatcctg  1140
ggcgacccca gccgaggaa cctcccttcc aggacgagcc gtaggacggc ggtgagagag   1200
gcacccgtcg cggaggtggc gcagcacaag gtgagcagcg cggggaaggc ggcgagcgtg  1260
gcggcctgca ggacggtgac gagcgcgaag acggtgacgc cggcgacgag gcagcagcag  1320
```

```
ccgaggttcc agtcgtagga ggaagccgga ccaaaccggg caatgcaacc tgcagatgca    1380
ctagacggag gtaacgagga ggaggagaaa acagagcaag agcaggcgga gagaagatag    1440
agcaaaacac gagtgaggca cagcgtaagc actcggtaga agtctccaga ggcgaggtgc    1500
gcacaggaga acagatgagt aaagtcagcc aaggatgcac gatccaacgg ctacgaattt    1560
ttggagtgac gtggataggc tcaaaggcgc catttccatc cggctttata gtattttaaa    1620
aaaattcatt ttcctccctc tagtgtgtgc ggaggcgtga gcccgtttaa cggcgttgag    1680
aagtctaacg gacaccaacc acaaccagga accagcgccg gccgcgccgc cgagtgaagc    1740
agactgcata cggcacggcg cggcatctct ctggctgcct ctcgagagtt ccgcccccac    1800
cttcccgcgg tagcgtggtg gtttcgcttt ccgctgtcgg catccggaag ttgcgtggca    1860
gagtggacgg agacgaggcc gggtcctcca gctcctctca aacgtcacgg caccggcatc    1920
cggcagccag cgcggtcctt cccaaccact cgttcccaac ccatcccct tcctcgcccg     1980
ccgtcataaa tagccagccc catcccagc ttctttcccc aacctcatct tctctccttt     2040
tgctctgaac gcacacaccg cccggtctcc gatctccgat ccccgatccc ctcgtcgatc    2100
ctaggtacgg cgaccatcct acccccccc ccccccctc tctctctgcc ttctctagat     2160
cggcgatccg atccatgctt acttggttag ggcctgctaa ctatgttcat gtttgcgtta    2220
gatccgtgca tggacgcgat ctgtacacac cagacgcgtt ctgattgcta gctaactcgc    2280
cagtacctgg gaatcctggg atggctgtag ccggccccgc acgcagacgg gaccgatttc    2340
atgattctct attttttcct ttgtttcgtt gcctaggtt tcgttcgatc gatccgcgtt     2400
attctttatt tccatatatt ctggtacgat gttgatacgg ttcgaccgtg ctgcttacgt    2460
tctgtgcgct tgtttgccgg gtcatttta ccttgccttt tttgtatggt ttggttgtgg     2520
cgatgtggtc tggtcgggct gtcgttctag atcggagtag agtgctgttt caaactgtct    2580
agcggatcta ttagatttgg atctgcatgt gtgacatata tcttcgtagt aagatgatg     2640
catctgtatg tgtgacatgc ggatctatta gatttggatc tgtatgtgtg acatatatct    2700
tcgtagttga gatgatgcat ctgtatgtgt gacatatatc ttcgtagtta agattatgca    2760
tggaaatatc aatcctttag ataaggacgg gtatacttgt tgctgtgggt tttactggta    2820
cttcgataga tgcatataca tgatctaaca tgcttagata catgaagtaa catgctgcta    2880
cggtttaata attcttgagt tgattttac tggtacttag atagatgtat atacatgctt     2940
agatacatga agtaacatgc tcctacagtt cctttaatca ttattgagta cctatatatt    3000
ctaataaatc agtatgtttt aaattatttt gattttactg gtacttagat agatgtatat    3060
atacatgctc aaacatgctt agatacatga agtaacatgc tgctacggtt tagtcattat    3120
tgagtgccta tatattctaa taaatcagta tgttttaaat tattttgatt ttactggtac    3180
ttagatagat gtatatatac atgctcaaac atgcttagat acatgaagta atatgctact    3240
acggtttaat tgttcttgag tacctatata ttctaataaa tcagtatgtt ttaaattatt    3300
tcgattttac tggtacttag atagatgtat atatacatgc ttagatacat gaagtaacat    3360
gctactacgg tttaattgtt cttgaatacc tatatattct aataaatcag tatgttttaa    3420
attatttcga ttttactggt acttagatag atgtatatat acatgctcga acatgcttag    3480
atacatgaag taacatgcta catatatatt ataataaatc agtatgtctt aaattattt     3540
gattttactg gtacttagat agatgtatat acatgctcaa acatgcttag atacatgaag    3600
taacatgcta ctacggttta atcattattg agtacctata tattctaata aatcagtatg    3660
ttttcaattg ttttgatttt actggtactt agatatatgt atatatacat gctcgaacat    3720
```

```
gcttagatac gtgaagtaac atgctactat ggttaattgt tcttgagtac ctatatattc    3780
taataaatca gtatgtttta aattatttcg attttactgg tacttagata gatgtatata    3840
tacatgctcg aacatgctta gatacatgaa gtaacatgct actacggttt aatcgttctt    3900
gagtacctat atattctaat aaatcagtat gtcttaaatt atcttgattt tactggtact    3960
tagatagatg tatatacatg cttagataca tgaagtaaca tgctactatg atttaatcgt    4020
tcttgagtac ctatatattc taataaatca gtatgttttt aattattttg attttactgg    4080
tacttagata gatgtatata tacatgctcg aacatgctta gatacatgaa gtaacatgct    4140
actacggttt aatcattctt gagtacctat atattctaat aaatcagtat gttttaatt     4200 attttgatat tactggtact taacatgttt agatacatca tatagcatgc acatgctgct    4260
actgtttaat cattcgtgaa tacctatata ttcaatatat tcagtatgtc ttctaattat    4320
tatgattttg atgtacttgt atggtggcat atgctgcagc tatgtgtaga ttttgaatac    4380
ccagtgtgat gagcatgcat ggcgccttca tagttcatat gctgtttatt tcctttgaga    4440
ctgttctttt ttgttgatag tcaccctgtt gtttggtgat tcttatccag atgagccccg    4500
aaaggaggcc cgtcgaaatc aggcccgcca ccgccgccga catggccgcc gtctgcgaca    4560
tcgtgaacca ctacatcgaa accagcaccg tcaactttag gaccgaaccc cagaccccc     4620 aggaatggat cgacgacctg gaaaggctgc aggacagata ccctggctg gtcgccgaag     4680 tcgaaggcgt cgtcgccggc atagcctacg ccggcccctg gaaggccagg aacgcctacg    4740
actggaccgt cgaaagcacc gtctacgtca gccacaggca ccagaggctg ggcctgggca    4800
gcaccctgta cacccacctg ctgaagagca tggaagccca gggcttcaag agcgtcgtcg    4860
ccgtcatcgg cctgcccaac gaccccagcg tcaggctgca cgaagccctg gctacaccg     4920 ccaggggcac cctgagggcc gccggctaca agcacggcgg ctggcacgac gtcggcttct    4980
ggcagaggga cttcgaactg cccgcccccc ccaggcccgt caggcccgtc acccagattt    5040
gagccaaggt tcaattaagc tgctgctgta cctgggtatc tgcgtcgtct ggtgccctct    5100
ggtgtacctc tatatggatc tcgtcgtcta ataaacatct gtggtttgtg tgtcatcaat    5160
cgtggttgtg gcttcgttgg tttaatggac ctgttgtgtc ctctgtgttg tacccaaaac    5220
tcttctgcag cagtatggct tgaatcctta tgaagtttga tatttgaact taaaagtctg    5280
ctcattatgt tttttttctgg ttatatctcc taattaactg cctgggatca aatttgattc    5340
gctggtgttt attggacccc tcccaggttc ttgctttcta ccgtttcttg ctgaatgtta    5400
acttgattct gtcaggctca gtttcccact atggcttaca gcttaacgtg tttggttgt     5460 tgaatgttaa cttggttttg tcaagctcag ttttttactc tggcttacag cataacatgt    5520
ttgacttttg gttttgctgc tttgttattg ggttctgggt agttcttgat gaatccaaaa    5580
gatcatgtgc acagccatat tatctattta agcgatccag gttattacta tgaaaggatg    5640
ccttctagct aaggagtagt taggttttt cttcaaggtt aaattttctc gatgctctag      5700
tgttcctgtg accataatca taataattcc tttgaaagct ctatggtccc tggaagcagg    5760
gcatacaatg caagacagca acttgatcac atcaactgaa gtatacaggg ttctcttaac    5820
tcttggtgac ttcggtttaa tggaccggtt gtactcgtgt tctatccgta accgttgtga    5880
tgtcttgtgt gtttggttgc gggatagctg ggaccacgac gtttccgtct aattctgatg    5940
gatagctata gacggcactg agatggttat attataaccct ctgatcctga actctacgag    6000
atcgtctcat ccgtcattgc caccaaatac accattaaat ta                       6042
```

<210> SEQ ID NO 11
<211> LENGTH: 552
<212> TYPE: DNA
<213> ORGANISM: Artificial Sequence
<220> FEATURE:
<223> OTHER INFORMATION: derived from Streptomyces viridochromogenes

<400> SEQUENCE: 11

| | | | | | |
|---|---|---|---|---|---|
| atgtccccag | agcgccggcc | ggtggagatc | aggccagcca | ccgccgccga | catggccgcc | 60 |
| gtgtgcgaca | tcgtgaacca | ctacatcgag | acctccaccg | tgaacttccg | gaccgagccg | 120 |
| cagaccccac | aggagtggat | cgacgacctc | gagcggctcc | aggaccgata | cccgtggctc | 180 |
| gtggccgagg | tggagggcgt | ggtggccggc | atcgcctacg | ccggcccctg | gaaggctagg | 240 |
| aacgcctacg | actggaccgt | ggagtccacc | gtgtacgtgt | cccaccgcca | ccagaggctc | 300 |
| ggcctcggct | ccaccctcta | cacccacctc | ctcaagtcta | tggaggccca | gggcttcaag | 360 |
| tccgtggtgg | ccgtgatcgg | cctaccgaac | gacccatccg | tgcggctcca | cgaggccctc | 420 |
| ggctacaccg | cccgaggcac | gctcagggcc | gccggctaca | gcacggcgg | ctggcacgac | 480 |
| gtgggcttct | ggcagaggga | cttcgagctg | ccagccccgc | aaggccagt | gcggccggtg | 540 |
| acccagattt | ga | | | | | 552 |

<210> SEQ ID NO 12
<211> LENGTH: 5552
<212> TYPE: DNA
<213> ORGANISM: Artificial Sequence
<220> FEATURE:
<223> OTHER INFORMATION: derived from Streptomyces viridochromogenes and Zea mays

<400> SEQUENCE: 12

| | | | | | |
|---|---|---|---|---|---|
| ggaaaaccaa | acaacgaat | aagcaaactg | caggaaaagt | atgcagtgga | aaccaaccca | 60 |
| gattcggacg | ataggaaagt | atcaagtgaa | tgatttgcca | ggaaaaggag | aggggtaaaa | 120 |
| aggggcgaag | atttagaaga | tctaaagcac | aagaaccaga | gattagattg | aacaataggg | 180 |
| aacttggagc | atccttttt | tcttcaggga | aaaactgaaa | atccaaacca | tgttgagcaa | 240 |
| aaccgagtgg | gattggaaac | caaaaaaccc | gagataaaga | aactcgagaa | aaagcatgaa | 300 |
| atcgaaacca | acttcagtaa | acaaaaagga | ggacagaaaa | gaaagtcgga | agctataaag | 360 |
| aatacattaa | cattcagtga | aacagcatgc | tgtcttcttc | ttttttatg | cacaacagag | 420 |
| catacatata | taccttccca | ggctgaggac | ttggcggagg | agagccgcgg | ataggttggc | 480 |
| ggtgcagacg | tctgacgg | gcccgaagac | ggagacgaac | agcgggccct | tcctgcccag | 540 |
| gcaccacgct | tggaacgcca | agcacgcgcc | aaccgcggcc | ccgccgagga | cgacgatccc | 600 |
| cgcgacaagc | gtggcgtcga | tcctgggcga | ccccaagccg | aggaacctcc | cttccaggac | 660 |
| gagccgtagg | acggcggtga | gagaggcacc | cgtcgcggag | gtggcgcagc | acaaggtgag | 720 |
| cagcgcgggg | aagcggcga | gcgtggcggc | ctgcaggacg | tgacgagcg | cgaagacggt | 780 |
| gacgccggcg | acgaggcagc | agcagccgag | gttccagtcg | taggaggaag | ccggaccaaa | 840 |
| ccgggcaatg | caacctgcag | atgcactaga | cggaggtaac | gaggaggagg | agaaaacaga | 900 |
| gcaagagcag | gcggagagaa | gatagagcaa | aacacgagtg | aggcacagcg | taagcactcg | 960 |
| gtagaagtct | ccagaggcga | ggtgcgcaca | ggagaacaga | tgagtaaagt | cagccaagga | 1020 |
| tgcacgatcc | aacggctacg | aattttttgga | gtgacgtgga | taggctcaaa | ggcgccattt | 1080 |
| ccatccggct | ttatagtatt | ttaaaaaaat | tcatttcct | ccctctagtg | tgtgcggagg | 1140 |

```
cgtgagcccg tttaacggcg ttgagaagtc taacggacac caaccacaac caggaaccag    1200
cgccggccgc gccgccgagt gaagcagact gcatacggca cggcgcggca tctctctggc    1260
tgcctctcga gagttccgcc cccaccttcc cgcggtagcg tggtggtttc gctttccgct    1320
gtcggcatcc ggaagttgcg tggcagagtg gacggagacg aggccgggtc ctccagctcc    1380
tctcaaacgt cacggcaccg gcatccggca gccagcgcgg tccttcccaa ccactcgttc    1440
ccaacccatc cccccttcctc gcccgccgtc ataaatagcc agcccatcc ccagcttctt    1500 tccccaacct catcttctct cctttgctc tgaacgcaca caccgcccgg tctccgatct    1560 ccgatcccg atcccctcgt cgatcctagg tacggcgacc atcctacccc cccccccccc    1620
ccctctctct ctgccttctc tagatcggcg atccgatcca tgcttacttg gttagggcct    1680
gctaactatg ttcatgtttg cgttagatcc gtgcatggac gcgatctgta cacaccagac    1740
gcgttctgat tgctagctaa ctcgccagta cctgggaatc ctgggatggc tgtagccggc    1800
cccgcacgca gacgggaccg atttcatgat tctctatttt tttctttgtt tcgttgccta    1860
gggtttcgtt cgatcgatcc gcgttattct ttatttccat atattctggt acgatgttga    1920
tacggttcga ccgtgctgct tacgttctgt gcgcttgttt gccgggtcat ttttaccttg    1980 cctttttgt atggtttggt tgtggcgatg tggtctggtc gggctgtcgt tctagatcgg    2040
agtagagtgc tgtttcaaac tgtctagcgg atctattaga tttggatctg catgtgtgac    2100
atatatcttc gtagttaaga tgatgcatct gtatgtgtga catgcggatc tattagattt    2160
ggatctgtat gtgtgacata tatcttcgta gttgagatga tgcatctgta tgtgtgacat    2220
atatcttcgt agttaagatt atgcatggaa atatcaatcc tttagataag gacgggtata    2280
cttgttgctg tgggttttac tggtacttcg atagatgcat atacatgatc taacatgctt    2340
agatacatga agtaacatgc tgctacggtt taataattct tgagttgatt tttactggta    2400
cttagataga tgtatataca tgcttagata catgaagtaa catgctccta cagttccttt    2460
aatcattatt gagtacctat atattctaat aaatcagtat gttttaaatt attttgattt    2520
tactggtact tagatagatg tatatataca tgctcaaaca tgcttagata catgaagtaa    2580
catgctgcta cggtttagtc attattgagt gcctatatat tctaataaat cagtatgttt    2640
taaattattt tgattttact ggtacttaga tagatgtata tatacatgct caaacatgct    2700
tagatacatg aagtaatatg ctactacggt ttaattgttc ttgagtacct atatattcta    2760
ataaatcagt atgttttaaa ttatttcgat tttactggta cttagataga tgtatatata    2820
catgcttaga tacatgaagt aacatgctac tacggtttaa ttgttcttga atacctatat    2880
attctaataa atcagtatgt tttaaattat ttcgatttta ctggtactta gatagatgta    2940 tatacatg ctcgaacatg cttagataca tgaagtaaca tgctacatat atattataat    3000
aaatcagtat gtcttaaatt attttgattt tactggtact tagatagatg tatatacatg    3060
ctcaaacatg cttagataca tgaagtaaca tgctactacg tttaatcat tattgagtac    3120 ctatatattc taataaatca gtatgttttc aattgttttg attttactgg tacttagata    3180
tatgtatata tacatgctcg aacatgctta gatacgtgaa gtaacatgct actatggtta    3240
attgttcttg agtacctata tattctaata atcagtatg ttttaaatta tttcgatttt    3300
actggtactt agatagatgt atatatacat gctcgaacat gcttagatac atgaagtaac    3360
atgctactac ggtttaatcg ttcttgagta cctatatatt ctaataaatc agtatgtctt    3420
aaattatctt gattttactg gtacttagat agatgtatat acatgcttag atacatgaag    3480
taacatgcta ctatgattta atcgttcttg agtacctata tattctaata aatcagtatg    3540
```

```
tttttaatta ttttgattttt actggtactt agatagatgt atatatacat gctcgaacat    3600
gcttagatac atgaagtaac atgctactac ggtttaatca ttcttgagta cctatatatt    3660
ctaataaatc agtatgtttt taattatttt gatattactg gtacttaaca tgtttagata    3720
catcatatag catgcacatg ctgctactgt ttaatcattc gtgaatacct atatattcta    3780
atatatcagt atgtcttcta attattatga ttttgatgta cttgtatggt ggcatatgct    3840
gcagctatgt gtagattttg aatacccagt gtgatgagca tgcatggcgc cttcatagtt    3900
catatgctgt ttatttcctt tgagactgtt ctttttttgtt gatagtcacc ctgttgtttg    3960
gtgattctta tccagatcca gatcttcgag atcctaaacc atgtcccag agcgccggcc     4020
ggtggagatc aggccagcca ccgccgccga catggccgcc gtgtgcgaca tcgtgaacca    4080
ctacatcgag acctccaccg tgaacttccg gaccgagccg cagacccac aggagtggat     4140
cgacgacctc gagcggctcc aggaccgata cccgtggctc gtggccgagg tggagggcgt    4200
ggtggccggc atcgcctacg ccggcccctg gaaggctagg aacgcctacg actggaccgt    4260
ggagtccacc gtgtacgtgt cccaccgcca ccagaggctc ggcctcggct ccaccctcta    4320
cacccacctc ctcaagtcta tggaggccca gggcttcaag tccgtggtgg ccgtgatcgg    4380
cctaccgaac gacccatccg tgcggctcca cgaggccctc ggctacaccg cccgaggcac    4440
gctcagggcc gccggctaca agcacggcgg ctggcacgac gtgggcttct ggcagaggga    4500
cttcgagctg ccagccccgc caaggccagt gcggccggtg acccagattt gagccaaggt    4560
tcaattaagc tgctgctgta cctgggtatc tgcgtcgtct ggtgccctct ggtgtacctc    4620
tatatggatc tcgtcgtcta ataaacatct gtggtttgtg tgtcatcaat cgtggttgtg    4680
gcttcgttgg tttaatggac ctgttgtgtc ctctgtgttg tacccaaaac tcttctgcag    4740
cagtatggct tgaatcctta tgaagtttga tatttgaact taaaagtctg ctcattatgt    4800
tttttttctgg ttatatctcc taattaactg cctgggatca aatttgattc gctggtgttt    4860
attggacccc tcccaggttc ttgctttcta ccgtttcttg ctgaatgtta acttgattct    4920
gtcaggctca gttccccact atggcttaca gcttaacgtg tttggtttgt tgaatgttaa    4980
cttggttttg tcaagctcag ttttttactc tggcttacag cataacatgt ttgacttttg    5040
gttttgctgc tttgttattg ggttctgggt agttcttgat gaatccaaaa gatcatgtgc    5100
acagccatat tatctattta agcgatccag gttattacta tgaaaggatg ccttctagct    5160
aaggagtagt taggtttttt cttcaaggtt aaattttctc gatgctctag tgttcctgtg    5220
accataatca taataattcc tttgaaagct ctatggtccc tggaagcagg gcatacaatg    5280
caagacagca acttgatcac atcaactgaa gtatacaggg ttctcttaac tcttggtgac    5340
ttcggtttaa tggaccggtt gtactcgtgt tctatccgta accgttgtga tgtcttgtgt    5400
gtttggttgc gggatagctg gaccacgac gtttccgtct aattctgatg gatagctata     5460
gacggcactg agatggttat attataacct ctgatcctga actctacgag atcgtctcat    5520
ccgtcattgc caccaaatac accattaaat ta                                  5552
```

<210> SEQ ID NO 13
<211> LENGTH: 5527
<212> TYPE: DNA
<213> ORGANISM: Artificial Sequence
<220> FEATURE:
<223> OTHER INFORMATION: derived from Streptomyces viridochromogenes and Zea mays

<400> SEQUENCE: 13

```
ggaaaaccaa aacaacgaat aagcaaactg caggaaaagt atgcagtgga aaccaaccca      60
gattcggacg ataggaaagt atcaagtgaa tgatttgcca ggaaaaggag agggtaaaa      120
aggggcgaag atttagaaga tctaaagcac aagaaccaga gattagattg aacaataggg     180
aacttggagc atccttttt tcttcaggga aaaactgaaa atccaaacca tgttgagcaa      240
aaccgagtgg gattggaaac caaaaaaccc gagataaaga aactcgagaa aaagcatgaa     300
atcgaaacca acttcagtaa aacaaaagga ggacagaaaa gaaagtcgga agctataaag     360
aatacattaa cattcagtga aacagcatgc tgtcttcttc tttttttatg cacaacagag     420
catacatata taccttccca ggctgaggac ttggcggagg agagccgcgg ataggttggc     480
ggtgcagacg gtctggacgg gcccgaagac ggagacgaac agcgggccct tcctgcccag     540
gcaccacgct tggaacgcca agcacgcgcc aaccgcggcc ccgccgagga cgacgatccc     600
cgcgacaagc gtggcgtcga tcctgggcga ccccaagccg aggaacctcc cttccaggac     660
gagccgtagg acggcggtga gagaggcacc cgtcgcggag gtggcgcagc acaaggtgag     720
cagcgcgggg aaggcggcga gcgtggcggc ctgcaggacg tgacgagcg cgaagacggt      780
gacgccggcg acgaggcagc agcagccgag gttccagtcg taggaggaag ccggaccaaa     840
ccgggcaatg caacctgcag atgcactaga cggaggtaac gaggaggagg agaaaacaga     900
gcaagagcag gcggagagaa gatagagcaa aacacgagtg aggcacagcg taagcactcg     960
gtagaagtct ccagaggcga ggtgcgcaca ggagaacaga tgagtaaagt cagccaagga   1020
tgcacgatcc aacggctacg aattttttgga gtgacgtgga taggctcaaa ggcgccattt   1080
ccatccggct ttatagtatt ttaaaaaaat tcattttcct ccctctagtg tgtgcggagg   1140
cgtgagcccg tttaacggcg ttgagaagtc taacggacac caaccacaac caggaaccag   1200
cgccggccgc gccgccgagt gaagcagact gcatacggca cggcgcggca tctctctggc   1260
tgcctctcga gagttccgcc cccaccttcc cgcggtagcg tggtggtttc gctttccgct   1320
gtcggcatcc ggaagttgcg tggcagagtg gacggagacg aggccgggtc ctccagctcc   1380
tctcaaacgt cacggcaccg gcatccggca gccagcgcgg tccttcccaa ccactcgttc   1440
ccaacccatc ccccttcctc gcccgccgtc ataaatagcc agccccatcc ccagcttctt   1500
tccccaacct catcttctct ccttttgctc tgaacgcaca caccgcccgg tctccgatct   1560
ccgatccccg atccctcgt cgatcctagg tacggcgacc atcctacccc cccccccc      1620
ccctctctct ctgccttctc tagatcggcg atccgatcca tgcttacttg gttagggcct   1680
gctaactatg ttcatgtttg cgttagatcc gtgcatggac gcgatctgta cacaccagac   1740
gcgttctgat tgctagctaa ctcgccagta cctgggaatc ctgggatggc tgtagccggc   1800
cccgcacgca gacgggaccg atttcatgat tctctatttt tttctttgtt tcgttgccta   1860
gggtttcgtt cgatcgatcc gcgttattct ttatttccat atattctggt acgatgttga   1920
tacggttcga ccgtgctgct tacgttctgt gcgcttgttt gccgggtcat ttttaccttg   1980
ccttttttgt atggtttggt tgtggcgatg tggtctggtc gggctgtcgt tctagatcgg   2040
agtagagtgc tgtttcaaac tgtctagcgg atctattaga tttggatctg catgtgtgac   2100
atatatcttc gtagttaaga tgatgcatct gtatgtgtga catgcggatc tattagattt   2160
ggatctgtat gtgtgacata tatccttcgta gttgagatga tgcatctgta tgtgtgacat   2220
atatcttcgt agttaagatt atgcatggaa atatcaatcc tttagataag gacgggtata   2280
```

```
cttgttgctg tgggttttac tggtacttcg atagatgcat atacatgatc taacatgctt    2340
agatacatga agtaacatgc tgctacggtt taataattct tgagttgatt tttactggta    2400
cttagataga tgtatataca tgcttagata catgaagtaa catgctccta cagttccttt    2460
aatcattatt gagtacctat atattctaat aaatcagtat gttttaaatt attttgattt    2520
tactggtact tagatagatg tatatataca tgctcaaaca tgcttagata catgaagtaa    2580
catgctgcta cggtttagtc attattgagt gcctatatat tctaataaat cagtatgttt    2640
taaattattt tgattttact ggtacttaga tagatgtata tatacatgct caaacatgct    2700
tagatacatg aagtaaatg ctactacggt ttaattgttc ttgagtacct atatattcta    2760
ataaatcagt atgttttaaa ttatttcgat tttactggta cttagataga tgtatatata    2820
catgcttaga tacatgaagt aacatgctac tacggtttaa ttgttcttga atacctatat    2880
attctaataa atcagtatgt tttaaattat ttcgatttta ctggtactta gatagatgta    2940
tatatacatg ctcgaacatg cttagataca tgaagtaaca tgctacatat atattataat    3000
aaatcagtat gtcttaaatt attttgattt tactggtact tagatagatg tatatacatg    3060
ctcaaacatg cttagataca tgaagtaaca tgctactacg gtttaatcat tattgagtac    3120
ctatatattc taataaatca gtatgttttc aattgttttg attttactgg tacttagata    3180
tatgtatata tacatgctcg aacatgctta gatacgtgaa gtaacatgct actatggtta    3240
attgttcttg agtacctata tattctaata atcagtatg ttttaaatta tttcgattttt    3300
actggtactt agatagatgt atatatacat gctcgaacat gcttagatac atgaagtaac    3360
atgctactac ggtttaatcg ttcttgagta cctatatatt ctaataaatc agtatgtctt    3420
aaattatctt gattttactg gtacttagat agatgtatat acatgcttag atacatgaag    3480
taacatgcta ctatgattta atcgttcttg agtacctata tattctaata atcagtatg    3540
tttttaatta ttttgatttt actggtactt agatagatgt atatatacat gctcgaacat    3600
gcttagatac atgaagtaac atgctactac ggtttaatca ttcttgagta cctatatatt    3660
ctaataaatc agtatgtttt taattatttt gatattactg gtacttaaca tgtttagata    3720
catcatatag catgcacatg ctgctactgt ttaatcattc gtgaatacct atatattcta    3780
atatatcagt atgtcttcta attattatga ttttgatgta cttgtatggt ggcatatgct    3840
gcagctatgt gtagattttg aatacccagt gtgatgagca tgcatggcgc ttcatagtt    3900
catatgctgt ttatttcctt tgagactgtt ctttttttgtt gatagtcacc ctgttgtttg    3960
gtgattctta tccagatgtc cccagagcgc cggccggtgg agatcaggcc agccaccgcc    4020
gccgacatgg ccgccgtgtg cgacatcgtg aaccactaca tcgagacctc caccgtgaac    4080
ttccggaccg agccgcagac cccacaggag tggatcgacg acctcgagcg gctccaggac    4140
cgatacccgt ggctcgtggc cgaggtggag ggcgtggtgg ccggcatcgc ctacgccggc    4200
ccctggaagg ctaggaacgc ctacgactgg accgtggagt ccaccgtgta cgtgtcccac    4260
cgccaccaga ggctcggcct cggctccacc ctctacaccc acctcctcaa gtctatggag    4320
gcccagggct tcaagtccgt ggtggccgtg atcggcctac cgaacgaccc atccgtgcgg    4380
ctccacgagg ccctcggcta caccgccga ggcacgctca gggccgccgg ctacaagcac    4440
ggcggctggc acgacgtggg cttctggcag agggacttcg agctgccagc cccgccaagg    4500
ccagtgcggc cggtgaccca gatttgagcc aaggttcaat taagctgctg ctgtacctgg    4560
gtatctgcgt cgtctggtgc cctctggtgt acctctatat ggatctcgtc gtctaataaa    4620
catctgtggt ttgtgtgtca tcaatcgtgg ttgtggcttc gttggtttaa tggacctgtt    4680
```

```
gtgtcctctg tgttgtaccc aaaactcttc tgcagcagta tggcttgaat ccttatgaag   4740
tttgatattt gaacttaaaa gtctgctcat tatgttttt tctggttata tctcctaatt    4800
aactgcctgg gatcaaattt gattcgctgg tgtttattgg acccctccca ggttcttgct   4860
ttctaccgtt tcttgctgaa tgttaacttg attctgtcag gctcagtttc ccactatggc   4920
ttacagctta acgtgtttgg tttgttgaat gttaacttgg ttttgtcaag ctcagttttt   4980
tactctggct tacagcataa catgtttgac ttttggtttt gctgctttgt tattgggttc   5040
tgggtagttc ttgatgaatc aaaagatca tgtgcacagc catattatct atttaagcga    5100
tccaggttat tactatgaaa ggatgccttc tagctaagga gtagttaggt tttttcttca   5160
aggttaaatt ttctcgatgc tctagtgttc ctgtgaccat aatcataata attcctttga   5220
aagctctatg gtccctggaa gcagggcata caatgcaaga cagcaacttg atcacatcaa   5280
ctgaagtata cagggttctc ttaactcttg gtgacttcgg tttaatggac cggttgtact   5340
cgtgttctat ccgtaaccgt tgtgatgtct tgtgtgtttg gttgcgggat agctgggacc   5400
acgacgtttc cgtctaattc tgatggatag ctatagacgg cactgagatg gttatattat   5460
aacctctgat cctgaactct acgagatcgt ctcatccgtc attgccacca aatacaccat   5520
taaatta                                                            5527

<210> SEQ ID NO 14
<211> LENGTH: 6067
<212> TYPE: DNA
<213> ORGANISM: Artificial Sequence
<220> FEATURE:
<223> OTHER INFORMATION: derived from Streptomyces viridochromogenes and
      Zea mays

<400> SEQUENCE: 14
agctgcttgt ggggaccaga caaaaaagga atggtgcaga attgttaggc gcacctacca     60
aaagcaactt tgcctttatt gcaaagataa agcagattcc tctagtacaa gtggggaaca    120 aataacgtg gaaaagagct gtcctgacag cccactcact attgcgtttg acgaacgcag     180
tgacgaccac aaaactcgag acttttcaac aaagggtatt atccggaaac ctcctcggat    240
tccattgccc agctatctgt cactttattg tgaagatagt ggaaaaggaa ggtggctcct    300
acaaatgcca tcattgcgat aaaggaaagg ctatcgttga agatgcctct gccgacagtg    360
gtcccaaaga tggacccca cccacgagga gcatcgtgga aaaagaagac gttccaacca     420
cgtcttcaaa gcaagtggat tgatgtgata tctccactga cgtaagggtt gacgaacaat    480
cccactatcc ttctgcctaa ttagctaacg gacccggaaa accaaaacaa cgaataagca    540
aactgcagga aaagtatgca gtggaaacca acccagattc ggacgatagg aaagtatcaa    600
gtgaatgatt tgccaggaaa aggagagggg taaaaggggg cgaagattta aagatctaa     660 agcacaagaa ccagagatta gattgaacaa tagggaactt ggagcatcct ttttttcttc    720
agggaaaaac tgaaaatcca aaccatgttg agcaaaaccg agtgggattg gaaaccaaaa    780
aacccgagat aaagaaactc gagaaaaagc atgaaatcga accaacttc agtaaaacaa     840 aaggaggaca gaaagaaag tcggaagcta taagaatac attaacattc agtgaaacag      900
catgctgtct tcttcttttt ttatgcacaa cagagcatac atatataccct tcccaggctg    960 aggacttggc ggaggagagc cgcggatagg ttggcggtgc agacggtctg gacgggcccg   1020
aagacggaga cgaacagcgg gcccttcctg cccaggcacc acgcttggaa cgccaagcac   1080
gcgccaaccg cggccccgcc gaggacgacg atccccgcga caagcgtggc gtcgatcctg   1140
```

```
ggcgacccca agccgaggaa cctcccttcc aggacgagcc gtaggacggc ggtgagagag    1200
gcacccgtcg cggaggtggc gcagcacaag gtgagcagcg cggggaaggc ggcgagcgtg    1260
gcggcctgca ggacggtgac gagcgcgaag acggtgacgc cggcgacgag gcagcagcag    1320
ccgaggttcc agtcgtagga ggaagccgga ccaaaccggg caatgcaacc tgcagatgca    1380
ctagacggag gtaacgagga ggaggagaaa acagagcaag agcaggcgga gagaagatag    1440
agcaaaacac gagtgaggca cagcgtaagc actcggtaga agtctccaga ggcgaggtgc    1500
gcacaggaga acagatgagt aaagtcagcc aaggatgcac gatccaacgg ctacgaattt    1560
ttggagtgac gtggatagcc tcaaaggcgc catttccatc cggctttata gtattttaaa    1620
aaaattcatt ttcctccctc tagtgtgtgc ggaggcgtga gcccgtttaa cggcgttgag    1680
aagtctaacg gacaccaacc acaaccagga accagcgccg gccgcgccgc cgagtgaagc    1740
agactgcata cggcacggcg cggcatctct ctggctgcct ctcgagagtt ccgcccccac    1800
cttcccgcgg tagcgtggtg gtttcgcttt ccgctgtcgg catccggaag ttgcgtggca    1860
gagtggacgg agacgaggcc gggtcctcca gctcctctca aacgtcacgg caccggcatc    1920
cggcagccag cgcggtcctt cccaaccact cgttcccaac ccatcccccct tcctcgcccg    1980 ccgtcataaa tagccagccc catccccagc ttctttcccc aacctcatct tctctccttt    2040
tgctctgaac gcacacaccg cccggtctcc gatctccgat ccccgatccc ctcgtcgatc    2100
ctaggtacgg cgaccatcct accccccccc cccccccctc tctctctgcc ttctctagat    2160
cggcgatccg atccatgctt acttggttag ggcctgctaa ctatgttcat gtttgcgtta    2220
gatccgtgca tggacgcgat ctgtacacac cagacgcgtt ctgattgcta gctaactcgc    2280
cagtacctgg gaatcctggg atggctgtag ccggccccgc acgcagacgg gaccgatttc    2340
atgattctct attttttct ttgtttcgtt gcctagggtt tcgttcgatc gatccgcgtt    2400
attctttatt tccatatatt ctggtacgat gttgatacgg ttcgaccgtg ctgcttacgt    2460
tctgtgcgct tgtttgccgg gtcatttttta ccttgccttt tttgtatggt ttggttgtgg    2520
cgatgtggtc tggtcgggct gtcgttctag atcggagtag agtgctgttt caaactgtct    2580
agcggatcta ttagatttgg atctgcatgt gtgacatata tcttcgtagt taagatgatg    2640
catctgtatg tgtgacatgc ggatctatta gatttggatc tgtatgtgtg acatatatct    2700
tcgtagttga gatgatgcat ctgtatgtgt gacatatatc ttcgtagtta agattatgca    2760
tggaaatatc aatcctttag ataaggacgg gtatacttgt tgctgtgggt tttactggta    2820
cttcgataga tgcatataca tgatctaaca tgcttagata catgaagtaa catgctgcta    2880
cggtttaata attcttgagt tgatttttac tggtacttag atagatgtat atacatgctt    2940
agatacatga agtaacatgc tcctacagtt cctttaatca ttattgagta cctatatatt    3000
ctaataaatc agtatgtttt aaattatttt gattttactg gtacttagat agatgtatat    3060
atacatgctc aaacatgctt agatacatga agtaacatgc tgctacggtt tagtcattat    3120
tgagtgccta tatattctaa taaatcagta tgttttaaat tattttgatt ttactggtac    3180
ttagatagat gtatatatac atgctcaaac atgcttagat acatgaagta atatgctact    3240
acggtttaat tgttcttgag tacctatata ttctaataaa tcagtatgtt ttaaattatt    3300
tcgattttac tggtacttag atagatgtat atacatgc ttagatacat gaagtaacat    3360
gctactacgg tttaattgtt cttgaatacc tatatattct aataaatcag tatgttttaa    3420
attatttcga ttttactggt acttagatag atgtatatat acatgctcga acatgcttag    3480
```

| | |
|---|---|
| atacatgaag taacatgcta catatatatt ataataaatc agtatgtctt aaattatttt | 3540 |
| gattttactg gtacttagat agatgtatat acatgctcaa acatgcttag atacatgaag | 3600 |
| taacatgcta ctacggttta atcattattg agtacctata tattctaata aatcagtatg | 3660 |
| ttttcaattg ttttgatttt actggtactt agatatatgt atatatacat gctcgaacat | 3720 |
| gcttagatac gtgaagtaac atgctactat ggttaattgt tcttgagtac ctatatattc | 3780 |
| taataaatca gtatgtttta aattatttcg atttttactgg tacttagata gatgtatata | 3840 |
| tacatgctcg aacatgctta gatacatgaa gtaacatgct actacggttt aatcgttctt | 3900 |
| gagtacctat atattctaat aaatcagtat gtcttaaatt atcttgattt tactggtact | 3960 |
| tagatagatg tatatacatg cttagataca tgaagtaaca tgctactatg atttaatcgt | 4020 |
| tcttgagtac ctatatattc taataaatca gtatgttttt aattattttg attttactgg | 4080 |
| tacttagata gatgtatata tacatgctcg aacatgctta gatacatgaa gtaacatgct | 4140 |
| actacggttt aatcattctt gagtacctat atattctaat aaatcagtat gttttttaatt | 4200 |
| attttgatat tactggtact taacatgttt agatacatca tatagcatgc acatgctgct | 4260 |
| actgtttaat cattcgtgaa tacctatata ttctaatata tcagtatgtc ttctaattat | 4320 |
| tatgattttg atgtacttgt atggtggcat atgctgcagc tatgtgtaga ttttgaatac | 4380 |
| ccagtgtgat gagcatgcat ggcgccttca tagttcatat gctgtttatt tcctttgaga | 4440 |
| ctgttctttt ttgttgatag tcaccctgtt gtttggtgat tcttatccag atccagatct | 4500 |
| tcgagatcct aaaccatgtc cccagagcgc cggccggtgg agatcaggcc agccaccgcc | 4560 |
| gccgacatgg ccgccgtgtg cgacatcgtg aaccactaca tcgagacctc caccgtgaac | 4620 |
| ttccggaccg agccgcagac cccacaggag tggatcgacg acctcgagcg gctccaggac | 4680 |
| cgataccgt ggctcgtggc cgaggtggag ggcgtggtgg ccggcatcgc ctacgccggc | 4740 |
| ccctggaagg ctaggaacgc ctacgactgg accgtggagt ccaccgtgta cgtgtcccac | 4800 |
| cgccaccaga ggctcggcct cggctccacc ctctacaccc acctcctcaa gtctatggag | 4860 |
| gcccagggct tcaagtccgt ggtggccgtg atcggcctac cgaacgaccc atccgtgcgg | 4920 |
| ctccacgagg ccctcggcta caccgcccga ggcacgctca gggccgccgg ctacaagcac | 4980 |
| ggcggctggc acgacgtggg cttctggcag agggacttcg agctgccagc cccgccaagg | 5040 |
| ccagtgcggc cggtgaccca gatttgagcc aaggttcaat taagctgctg ctgtacctgg | 5100 |
| gtatctgcgt cgtctggtgc cctctggtgt acctctatat ggatctcgtc gtctaataaa | 5160 |
| catctgtggt ttgtgtgtca tcaatcgtgg ttgtggcttc gttggtttaa tggacctgtt | 5220 |
| gtgtcctctg tgttgtaccc aaaactcttc tgcagcagta tggcttgaat ccttatgaag | 5280 |
| tttgatattt gaacttaaaa gtctgctcat tatgtttttt tctggttata tctcctaatt | 5340 |
| aactgcctgg gatcaaattt gattcgctgg tgtttattgg accctccca ggttcttgct | 5400 |
| ttctaccgtt tcttgctgaa tgttaacttg attctgtcag gctcagtttc ccactatggc | 5460 |
| ttacagctta acgtgtttgg tttgttgaat gttaacttgg ttttgtcaag ctcagttttt | 5520 |
| tactctggct tacagcataa catgtttgac ttttggtttt gctgctttgt tattgggttc | 5580 |
| tgggtagttc ttgatgaatc caaaagatca tgtgcacagc catattatct atttaagcga | 5640 |
| tccaggttat tactatgaaa ggatgccttc tagctaagga gtagttaggt ttttcttca | 5700 |
| aggttaaatt ttctcgatgc tctagtgttc ctgtgaccat aatcataata attcctttga | 5760 |
| aagctctatg gtccctggaa gcagggcata caatgcaaga cagcaacttg atcacatcaa | 5820 |
| ctgaagtata cagggttctc ttaactcttg gtgacttcgg tttaatggac cggttgtact | 5880 |

```
cgtgttctat ccgtaaccgt tgtgatgtct tgtgtgtttg gttgcgggat agctgggacc    5940
acgacgtttc cgtctaattc tgatggatag ctatagacgg cactgagatg gttatattat    6000
aacctctgat cctgaactct acgagatcgt ctcatccgtc attgccacca aatacaccat    6060
taaatta                                                              6067
```

<210> SEQ ID NO 15
<211> LENGTH: 6042
<212> TYPE: DNA
<213> ORGANISM: Artificial Sequence
<220> FEATURE:
<223> OTHER INFORMATION: derived from Streptomyces viridochromogenes and
      Zea mays

<400> SEQUENCE: 15

```
agctgcttgt ggggaccaga caaaaaagga atggtgcaga attgttaggc gcacctacca      60
aaagcaactt tgcctttatt gcaaagataa agcagattcc tctagtacaa gtggggaaca     120
aaataacgtg gaaaagagct gtcctgacag cccactcact attgcgtttg acgaacgcag     180
tgacgaccac aaaactcgag acttttcaac aaagggtatt atccggaaac ctcctcggat     240
tccattgccc agctatctgt cacttttattg tgaagatagt ggaaaaggaa ggtggctcct     300
acaaatgcca tcattgcgat aaaggaaagg ctatcgttga agatgcctct gccgacagtg     360
gtcccaaaga tggaccccca cccacgagga gcatcgtgga aaaagaagac gttccaacca     420
cgtcttcaaa gcaagtggat tgatgtgata tctccactga cgtaagggtt gacgaacaat     480
cccactatcc ttctgcctaa ttagctaacg gacccggaaa accaaaacaa cgaataagca     540
aactgcagga aaagtatgca gtggaaacca acccagattc ggacgatagg aaagtatcaa     600
gtgaatgatt tgccaggaaa aggagagggg taaaagggg cgaagattta gaagatctaa       660
agcacaagaa ccagagatta gattgaacaa tagggaactt ggagcatcct tttttttcttc    720 agggaaaaac tgaaaatcca aaccatgttg agcaaaaccg agtgggattg gaaaccaaaa     780
aacccgagat aaagaaactc gagaaaaagc atgaaatcga aaccaacttc agtaaaacaa     840
aaggaggaca gaaaagaaag tcggaagcta taaagaatac attaacattc agtgaaacag     900
catgctgtct tcttcttttt ttatgcacaa cagagcatac atatataccct tcccaggctg     960 aggacttggc ggaggagagc cgcggatagg ttggcggtgc agacggtctg gacgggcccg    1020
aagacggaga cgaacagcgg gccccttcctg cccaggcacc acgcttggaa cgccaagcac    1080
gcgccaaccg cggccccgcc gaggacgacg atccccgcga caagcgtggc gtcgatcctg    1140
ggcgacccca agccgaggaa cctcccttcc aggacgagcc gtaggacggc ggtgagagag    1200
gcacccgtcg cggaggtggc gcagcacaag gtgagcagcg cggggaaggc ggcgagcgtg    1260
gcggcctgca ggacggtgac gagcgcgaag acggtgacgc cggcgacgag gcagcagcag    1320
ccgaggttcc agtcgtagga ggaagccgga ccaaaccggg caatgcaacc tgcagatgca    1380
ctagacggag gtaacgagga ggaggagaaa acagagcaag agcaggcgga gagaagatag    1440
agcaaaacac gagtgaggca cagcgtaagc actcggtaga agtctccaga ggcgaggtgc    1500
gcacaggaga acagatgagt aaagtcagcc aaggatgcac gatccaacgg ctacgaattt    1560
ttggagtgac gtggataggc tcaaaggcgc catttccatc cggctttata gtattttaaa    1620
aaaattcatt ttcctccctc tagtgtgtgc ggaggcgtga gccgtttaa cggcgttgag    1680 aagtctaacg gacaccaacc acaaccagga accagcgccg gccgcgccgc cgagtgaagc    1740
agactgcata cggcacggcg cggcatctct ctggctgcct ctcgagagtt ccgcccccac    1800
```

```
cttcccgcgg tagcgtggtg gtttcgcttt ccgctgtcgg catccggaag ttgcgtggca   1860
gagtggacgg agacgaggcc gggtcctcca gctcctctca aacgtcacgg caccggcatc   1920
cggcagccag cgcggtcctt cccaaccact cgttcccaac ccatcccect tcctcgcccg   1980 ccgtcataaa tagccagccc catccccagc ttctttcccc aacctcatct tctctccttt   2040
tgctctgaac gcacacaccg cccggtctcc gatctccgat ccccgatccc ctcgtcgatc   2100
ctaggtacgg cgaccatcct accccccccc ccccccctc tctctctgcc ttctctagat    2160
cggcgatccg atccatgctt acttggttag ggcctgctaa ctatgttcat gtttgcgtta   2220
gatccgtgca tggacgcgat ctgtacacac cagacgcgtt ctgattgcta gctaactcgc   2280
cagtacctgg gaatcctggg atggctgtag ccggccccgc acgcagacgg gaccgatttc   2340
atgattctct attttttct ttgtttcgtt gcctagggtt tcgttcgatc gatccgcgtt    2400
attctttatt tccatatatt ctggtacgat gttgatacgg ttcgaccgtg ctgcttacgt   2460
tctgtgcgct tgtttgccgg gtcattttta ccttgccttt tttgtatggt ttggttgtgg   2520
cgatgtggtc tggtcgggct gtcgttctag atcggagtag agtgctgttt caaactgtct   2580
agcggatcta ttagatttgg atctgcatgt gtgacatata tcttcgtagt taagatgatg   2640
catctgtatg tgtgacatgc ggatctatta gatttggatc tgtatgtgtg acatatatct   2700
tcgtagttga gatgatgcat ctgtatgtgt gacatatatc ttcgtagtta agattatgca   2760
tggaaatatc aatcctttag ataaggacgg gtatacttgt tgctgtgggt tttactggta   2820
cttcgataga tgcatataca tgatctaaca tgcttagata catgaagtaa catgctgcta   2880
cggtttaata attcttgagt tgatttttac tggtacttag atagatgtat atacatgctt   2940
agatacatga agtaacatgc tcctacagtt cctttaatca ttattgagta cctatatatt   3000
ctaataaatc agtatgtttt aaattatttt gattttactg gtacttagat agatgtatat   3060
atacatgctc aaacatgctt agatacatga agtaacatgc tgctacggtt tagtcattat   3120
tgagtgccta tatattctaa taaatcagta tgttttaaat tattttgatt ttactggtac   3180
ttagatagat gtatatatac atgctcaaac atgcttagat acatgaagta atatgctact   3240
acggtttaat tgttcttgag tacctatata ttctaataaa tcagtatgtt ttaaattatt   3300
tcgattttac tggtacttag atagatgtat atacatgc ttagatacat gaagtaacat   3360
gctactacgg tttaattgtt cttgaatacc tatatattct aataaatcag tatgttttaa   3420
attatttcga ttttactggt acttagatag atgtatatat acatgctcga acatgcttag   3480
atacatgaag taacatgcta catatatatt ataataaatc agtatgtctt aaattatttt   3540
gattttactg gtacttagat agatgtatat acatgctcaa acatgcttag atacatgaag   3600
taacatgcta ctacggttta atcattattg agtacctata tattctaata atcagtatg    3660 ttttcaattg ttttgatttt actggtactt agatatatgt atatatacat gctcgaacat   3720
gcttagatac gtgaagtaac atgctactat ggttaattgt tcttgagtac ctatatattc   3780
taataaatca gtatgtttta aattatttcg attttactgg tacttagata gatgtatata   3840
tacatgctcg aacatgctta gatacatgaa gtaacatgct actacggttt aatcgttctt   3900
gagtacctat atattctaat aaatcagtat gtcttaaatt atcttgattt tactggtact   3960
tagatagatg tatatacatg cttagataca tgaagtaaca tgctactatg atttaatcgt   4020
tcttgagtac ctatatattc taataaatca gtatgttttt aattattttg attttactgg   4080
tacttagata gatgtatata tacatgctcg aacatgctta gatacatgaa gtaacatgct   4140
```

```
actacggttt aatcattctt gagtacctat atattctaat aaatcagtat gttttttaatt    4200 attttgatat tactggtact taacatgttt agatacatca tatagcatgc acatgctgct    4260
actgtttaat cattcgtgaa tacctatata ttctaatata tcagtatgtc ttctaattat    4320
tatgattttg atgtacttgt atggtggcat atgctgcagc tatgtgtaga ttttgaatac    4380
ccagtgtgat gagcatgcat ggcgccttca tagttcatat gctgtttatt ccttttgaga    4440
ctgttctttt ttgttgatag tcaccctgtt gtttggtgat tcttatccag atgtccccag    4500
agcgccggcc ggtggagatc aggccagcca ccgccgccga catggccgcc gtgtgcgaca    4560
tcgtgaacca ctacatcgag acctccaccg tgaacttccg gaccgagcca cagaccccac    4620
aggagtggat cgacgacctc gagcggctcc aggaccgata cccgtggctc gtggccgagg    4680
tggagggcgt ggtggccggc atcgcctacg ccggcccctg gaaggctagg aacgcctacg    4740
actggaccgt ggagtccacc gtgtacgtgt cccaccgcca ccagaggctc ggcctcggct    4800
ccaccctcta cacccacctc ctcaagtcta tggaggccca gggcttcaag tccgtggtgg    4860
ccgtgatcgg cctaccgaac gacccatccg tgcggctcca cgaggccctc ggctacaccg    4920
cccgaggcac gctcagggcc gccggctaca agcacggcgg ctggcacgac gtgggcttct    4980
ggcagaggga cttcgagctg ccagcccgc caaggccagt gcggccggtg acccagattt    5040
gagccaaggt tcaattaagc tgctgctgta cctgggtatc tgcgtcgtct ggtgccctct    5100
ggtgtacctc tatatggatc tcgtcgtcta ataaacatct gtggtttgtg tgtcatcaat    5160
cgtggttgtg gcttcgttgg tttaatggac ctgttgtgtc ctctgtgttg tacccaaaac    5220
tcttctgcag cagtatggct tgaatcctta tgaagtttga tatttgaact taaaagtctg    5280
ctcattatgt tttttttctgg ttatatctcc taattaactg cctgggatca aatttgattc    5340
gctggtgttt attggacccc tcccaggttc ttgctttcta ccgtttcttg ctgaatgtta    5400
acttgattct gtcaggctca gtttcccact atggcttaca gcttaacgtg tttggtttgt    5460
tgaatgttaa cttggttttg tcaagctcag ttttttactc tggcttacag cataacatgt    5520
ttgacttttg gttttgctgc tttgttattg ggttctgggt agttcttgat gaatccaaaa    5580
gatcatgtgc acagccatat tatctattta agcgatccag gttattacta tgaaaggatg    5640
ccttctagct aaggagtagt taggtttttt cttcaaggtt aaattttctc gatgctctag    5700
tgttcctgtg accataatca taataattcc tttgaaagct ctatggtccc tggaagcagg    5760
gcatacaatg caagacagca acttgatcac atcaactgaa gtatacaggg ttctcttaac    5820
tcttggtgac ttcggtttaa tggaccggtt gtactcgtgt tctatccgta accgttgtga    5880
tgtcttgtgt gtttggttgc gggatagctg ggaccacgac gtttccgtct aattctgatg    5940
gatagctata gacggcactg agatggttat attataaccct ctgatcctga actctacgag    6000
atcgtctcat ccgtcattgc caccaaatac accattaaat ta                       6042
```

<210> SEQ ID NO 16
<211> LENGTH: 552
<212> TYPE: DNA
<213> ORGANISM: Artificial Sequence
<220> FEATURE:
<223> OTHER INFORMATION: derived from Streptomyces viridochromogenes

<400> SEQUENCE: 16

```
atgtccccag agaggaggcc agtggagatc aggccagcca ccgccgccga catggccgcc     60
gtgtgcgaca tcgtgaacca ctacatcgag acctccaccg tgaacttcag gaccgagcca    120
cagaccccac aggagtggat cgacgacctc gagaggctcc aggacagata cccctggctc    180
```

```
gtggccgagg tggagggcgt ggtggccggc atcgcctacg ccggcccctg gaaagctagg    240
aacgcctacg actggaccgt ggagtccacc gtgtacgtgt cccacaggca ccagaggctc    300
ggcctcggct ccaccctcta cacccacctc ctcaagtcta tggaggccca gggcttcaag    360
tccgtggtgg ccgtgatcgg cctaccaaac gacccatccg tgaggctcca cgaggccctc    420
ggctacaccg cgagaggcac cctcagggcc gccggctaca agcacggcgg ctggcacgac    480
gtgggcttct ggcagaggga cttcgagctg ccagccccac caaggccagt gaggccagtg    540
acccagattt ga                                                        552
```

<210> SEQ ID NO 17
<211> LENGTH: 5552
<212> TYPE: DNA
<213> ORGANISM: Artificial Sequence
<220> FEATURE:
<223> OTHER INFORMATION: derived from Streptomyces viridochromogenes and
      Zea mays

<400> SEQUENCE: 17

```
ggaaaaccaa acaacgaat aagcaaactg caggaaaagt atgcagtgga accaaccca      60 gattcggacg ataggaaagt atcaagtgaa tgatttgcca ggaaaaggag aggggtaaaa    120
aggggcgaag atttagaaga tctaaagcac aagaaccaga gattagattg aacaataggg    180
aacttggagc atccttttttt tcttcaggga aaaactgaaa atccaaacca tgttgagcaa    240
aaccgagtgg gattggaaac caaaaaaccc gagataaaga aactcgagaa aaagcatgaa    300
atcgaaacca acttcagtaa aacaaaagga ggacagaaaa gaaagtcgga agctataaag    360
aatacattaa cattcagtga aacagcatgc tgtcttcttc tttttttatg cacaacagag    420
catacatata taccttccca ggctgaggac ttggcggagg agagccgcgg ataggttggc    480
ggtgcagacg gtctggacgg gcccgaagac ggagacgaac agcgggccct tcctgcccag    540
gcaccacgct tggaacgcca agcacgcgcc aaccgcggcc ccgccgagga cgacgatccc    600
cgcgacaagc gtggcgtcga tcctgggcga ccccaagccg aggaacctcc cttccaggac    660
gagccgtagg acggcggtga gagaggcacc cgtcgcggag gtggcgcagc acaaggtgag    720
cagcgcgggg aaggcggcga gcgtggcggc ctgcaggacg gtgacgagcg cgaagacggt    780
gacgccggcg acgaggcagc agcagccgag gttccagtcg taggaggaag ccggaccaaa    840
ccgggcaatg caacctgcag atgcactaga cggaggtaac gaggaggagg agaaaacaga    900
gcaagagcag gcggagagaa gatagagcaa aacacgagtg aggcacagcg taagcactcg    960
gtagaagtct ccagaggcga ggtgcgcaca ggagaacaga tgagtaaagt cagccaagga    1020
tgcacgatcc aacggctacg aatttttgga gtgacgtgga taggctcaaa ggcgccattt    1080
ccatccggct ttatagtatt ttaaaaaaat tcatttttcct ccctctagtg tgtgcggagg    1140
cgtgagcccg tttaacggcg ttgagaagtc taacggacac caaccacaac caggaaccag    1200
cgccggccgc gccgccgagt gaagcagact gcatacggca cggcgcggca tctctctggc    1260
tgcctctcga gagttccgcc cccaccttcc cgcggtagcg tggtggtttc gctttccgct    1320
gtcggcatcc ggaagttgcg tggcagagtg acggagacg aggccgggtc ctccagctcc    1380
tctcaaacgt cacggcaccg gcatccggca gccagcgcgg tccttcccaa ccactcgttc    1440
ccaacccatc cccctttcctc gcccgccgtc ataaatagcc agccccatcc ccagcttctt    1500
tccccaacct catcttctct ccttttgctc tgaacgcaca caccgccggg tctccgatct    1560
ccgatccccg atccctcgt cgatcctagg tacggcgacc atcctacccc cccccccccc    1620
```

```
ccctctctct ctgccttctc tagatcggcg atccgatcca tgcttacttg gttagggcct    1680
gctaactatg ttcatgtttg cgttagatcc gtgcatggac gcgatctgta cacaccagac    1740
gcgttctgat tgctagctaa ctcgccagta cctgggaatc ctgggatggc tgtagccggc    1800
cccgcacgca gacgggaccg atttcatgat tctctatttt tttctttgtt tcgttgccta    1860
gggtttcgtt cgatcgatcc gcgttattct ttatttccat atattctggt acgatgttga    1920
tacggttcga ccgtgctgct tacgttctgt gcgcttgttt gccgggtcat ttttaccttg    1980
ccttttttgt atggtttggt tgtggcgatg tggtctggtc gggctgtcgt tctagatcgg    2040
agtagagtgc tgtttcaaac tgtctagcgg atctattaga tttggatctg catgtgtgac    2100
atatatcttc gtagttaaga tgatgcatct gtatgtgtga catgcggatc tattagattt    2160
ggatctgtat gtgtgacata tatcttcgta gttgagatga tgcatctgta tgtgtgacat    2220
atatcttcgt agttaagatt atgcatggaa atatcaatcc tttagataag gacgggtata    2280
cttgttgctg tgggttttac tggtacttcg atagatgcat atacatgatc taacatgctt    2340
agatacatga agtaacatgc tgctacggtt taataattct tgagttgatt tttactggta    2400
cttagataga tgtatataca tgcttagata catgaagtaa catgctccta cagttccttt    2460
aatcattatt gagtacctat atattctaat aaatcagtat gttttaaatt attttgattt    2520
tactggtact tagatagatg tatatataca tgctcaaaca tgcttagata catgaagtaa    2580
catgctgcta cggtttagtc attattgagt gcctatatat tctaataaat cagtatgttt    2640
taaattattt tgatttact ggtacttaga tagatgtata tacatgct caaacatgct       2700 tagatacatg aagtaatatg ctactacggt ttaattgttc ttgagtacct atatattcta    2760
ataaatcagt atgttttaaa ttatttcgat tttactggta cttagataga tgtatatata    2820
catgcttaga tacatgaagt aacatgctac tacggtttaa ttgttcttga atacctatat    2880
attctaataa atcagtatgt tttaaattat ttcgatttta ctggtactta gatagatgta    2940
tatatacatg ctcgaacatg cttagataca tgaagtaaca tgctacatat atattataat    3000
aaatcagtat gtcttaaatt attttgattt tactggtact tagatagatg tatatacatg    3060
ctcaaacatg cttagataca tgaagtaaca tgctactacg gtttaatcat tattgagtac    3120
ctatatattc taataaatca gtatgttttc aattgttttg attttactgg tacttagata    3180
tatgtatata tacatgctcg aacatgctta gatacgtgaa gtaacatgct actatggtta    3240
attgttcttg agtacctata tattctaata atcagtatg ttttaaatta tttcgatttt     3300
actggtactt agatagatgt atatatacat gctcgaacat gctagatac atgaagtaac     3360 atgctactac ggtttaatcg ttcttgagta cctatatatt ctaataaatc agtatgtctt    3420
aaattatctt gatttactg gtacttagat agatgtatat acatgcttag atacatgaag    3480
taacatgcta ctatgattta atcgttcttg agtacctata tattctaata aatcagtatg    3540
tttttaatta ttttgatttt actggtactt agatagatgt atatatacat gctcgaacat    3600
gcttagatac atgaagtaac atgctactac ggtttaatca ttcttgagta cctatatatt    3660
ctaataaatc agtatgtttt taattatttt gatattactg gtacttaaca tgtttagata    3720
catcatatag catgcacatg ctgctactgt ttaatcattg gtgaatacct atatattcta    3780
atatatcagt atgtcttcta attattatga ttttgatgta cttgtatggt ggcatatgct    3840
gcagctatgt gtagattttg aatacccagt gtgatgagca tgcatggcgc cttcatagtt    3900
catatgctgt ttatttcctt tgagactgtt ctttttttgtt gatagtcacc ctgttgtttg    3960
```

| | |
|---|---:|
| gtgattctta tccagatcca gatcttcgag atcctaaacc atgtccccag agaggaggcc | 4020 |
| agtggagatc aggccagcca ccgccgccga catggccgcc gtgtgcgaca tcgtgaacca | 4080 |
| ctacatcgag acctccaccg tgaacttcag gaccgagcca cagaccccac aggagtggat | 4140 |
| cgacgacctc gagaggctcc aggacagata cccctggctc gtggccgagg tggagggcgt | 4200 |
| ggtggccggc atcgcctacg ccggcccctg gaaagctagg aacgcctacg actggaccgt | 4260 |
| ggagtccacc gtgtacgtgt cccacaggca ccagaggctc ggcctcggct ccaccctcta | 4320 |
| cacccacctc ctcaagtcta tggaggccca gggcttcaag tccgtggtgg ccgtgatcgg | 4380 |
| cctaccaaac gacccatccg tgaggctcca cgaggccctc ggctacaccg cgagaggcac | 4440 |
| cctcagggcc gccggctaca agcacggcgg ctggcacgac gtgggcttct ggcagaggga | 4500 |
| cttcgagctg ccagccccac caaggccagt gaggccagtg acccagattt gagccaaggt | 4560 |
| tcaattaagc tgctgctgta cctgggtatc tgcgtcgtct ggtgccctct ggtgtacctc | 4620 |
| tatatggatc tcgtcgtcta ataaacatct gtggtttgtg tgtcatcaat cgtggttgtg | 4680 |
| gcttcgttgg tttaatggac ctgttgtgtc ctctgtgttg tacccaaaac tcttctgcag | 4740 |
| cagtatggct tgaatcctta tgaagtttga tatttgaact taaaagtctg ctcattatgt | 4800 |
| ttttttctgg ttatatctcc taattaactg cctgggatca aatttgattc gctggtgttt | 4860 |
| attggacccc tcccaggttc ttgctttcta ccgtttcttg ctgaatgtta acttgattct | 4920 |
| gtcaggctca gtttcccact atggcttaca gcttaacgtg tttggtttgt tgaatgttaa | 4980 |
| cttggttttg tcaagctcag ttttttactc tggcttacag cataacatgt ttgacttttg | 5040 |
| gttttgctgc tttgttattg ggttctgggt agttcttgat gaatccaaaa gatcatgtgc | 5100 |
| acagccatat tatctattta agcgatccag gttattacta tgaaaggatg ccttctagct | 5160 |
| aaggagtagt taggtttttt cttcaaggtt aaatttctc gatgctctag tgttcctgtg | 5220 |
| accataatca taataattcc tttgaaagct ctatggtccc tggaagcagg gcatacaatg | 5280 |
| caagacagca acttgatcac atcaactgaa gtatacaggg ttctcttaac tcttggtgac | 5340 |
| ttcggtttaa tggaccggtt gtactcgtgt tctatccgta accgttgtga tgtcttgtgt | 5400 |
| gtttggttgc gggatagctg gaccacgac gtttccgtct aattctgatg gatagctata | 5460 |
| gacggcactg agatggttat attataaact ctgatcctga actctacgag atcgtctcat | 5520 |
| ccgtcattgc caccaaatac accattaaat ta | 5552 |

<210> SEQ ID NO 18
<211> LENGTH: 5527
<212> TYPE: DNA
<213> ORGANISM: Artificial Sequence
<220> FEATURE:
<223> OTHER INFORMATION: derived from Streptomyces viridochromogenes and
      Zea mays

<400> SEQUENCE: 18

| | |
|---|---:|
| ggaaaccaa acaacgaat aagcaaactg caggaaaagt atgcagtgga aaccaaccca | 60 |
| gattcggacg ataggaaagt atcaagtgaa tgatttgcca ggaaaaggag aggggtaaaa | 120 |
| aggggcgaag atttagaaga tctaaagcac aagaaccaga gattagattg aacaataggg | 180 |
| aacttggagc atcctttttt tcttcaggga aaaactgaaa atccaaacca tgttgagcaa | 240 |
| aaccgagtgg gattggaaac caaaaaaccc gagataaaga aactcgagaa aaagcatgaa | 300 |
| atcgaaacca acttcagtaa aacaaaagga ggacagaaaa gaaagtcgga agctataaag | 360 |
| aatacattaa cattcagtga aacagcatgc tgtcttcttc ttttttatg cacaacagag | 420 |

```
catacatata taccttccca ggctgaggac ttggcggagg agagccgcgg ataggttggc    480
ggtgcagacg gtctggacgg gcccgaagac ggagacgaac agcgggccct tcctgcccag    540
gcaccacgct tggaacgcca agcacgcgcc aaccgcggcc ccgccgagga cgacgatccc    600
cgcgacaagc gtggcgtcga tcctgggcga ccccaagccg aggaacctcc cttccaggac    660
gagccgtagg acggcggtga gagaggcacc cgtcgcggag gtggcgcagc acaaggtgag    720
cagcgcgggg aaggcggcga gcgtggcggc ctgcaggacg tgacgagcg cgaagacggt    780 gacgccggcg acgaggcagc agcagccgag gttccagtcg taggaggaag ccggaccaaa    840
ccgggcaatg caacctgcag atgcactaga cggaggtaac gaggaggagg agaaaacaga    900
gcaagagcag gcggagagaa gatagagcaa aacacgagtg aggcacagcg taagcactcg    960
gtagaagtct ccagaggcga ggtgcgcaca ggagaacaga tgagtaaagt cagccaagga   1020
tgcacgatcc aacggctacg aatttttgga gtgacgtgga taggctcaaa ggcgccattt   1080
ccatccggct ttatagtatt ttaaaaaaat tcattttcct ccctctagtg tgtgcggagg   1140
cgtgagcccg tttaacggcg ttgagaagtc taacggacac caaccacaac caggaaccag   1200
cgccggccgc gccgccgagt gaagcagact gcatacggca cggcgcggca tctctctggc   1260
tgcctctcga gagttccgcc cccaccttcc cgcggtagcg tggtggtttc gctttccgct   1320
gtcggcatcc ggaagttgcg tggcagagtg gacggagacg aggccgggtc ctccagctcc   1380
tctcaaacgt cacggcaccg gcatccggca gccagcgcgg tccttcccaa ccactcgttc   1440
ccaacccatc cccttcctc gcccgccgtc ataaatagcc agccccatcc ccagcttctt    1500
tccccaacct catcttctct cctttgctc tgaacgcaca caccgccggg tctccgatct    1560
ccgatccccg atccctcgt cgatcctagg tacggcgacc atcctacccc cccccccccc    1620
ccctctctct ctgccttctc tagatcgcg atccgatcca tgcttacttg gttagggcct    1680
gctaactatg ttcatgtttg cgttagatcc gtgcatggac gcgatctgta cacaccagac   1740
gcgttctgat tgctagctaa ctcgccagta cctgggaatc ctgggatggc tgtagccggc   1800
cccgcacgca gacgggaccg atttcatgat tctctatttt tttctttgtt tcgttgccta   1860
gggtttcgtt cgatcgatcc gcgttattct ttatttccat atattctggt acgatgttga   1920
tacggttcga ccgtgctgct tacgttctgt gcgcttgttt gccgggtcat ttttaccttg   1980
ccttttttgt atggtttggt tgtggcgatg tggtctggtc gggctgtcgt tctagatcgg   2040
agtagagtgc tgtttcaaac tgtctagcgg atctattaga tttggatctg catgtgtgac   2100
atatatcttc gtagttaaga tgatgcatct gtatgtgtga catgcggatc tattagattt   2160
ggatctgtat gtgtgacata tatcttcgta gttgagatga tgcatctgta tgtgtgacat   2220
atatcttcgt agttaagatt atgcatggaa atatcaatcc tttagataag gacgggtata   2280
cttgttgctg tgggttttac tggtacttcg atagatgcat atacatgatc taacatgctt   2340
agatacatga gtaacatgc tgctacggtt taataattct tgagttgatt tttactggta    2400
cttagataga tgtatataca tgcttagata catgaagtaa catgctccta cagttccttt   2460
aatcattatt gagtacctat atattctaat aaatcagtat gttttaaatt attttgattt   2520
tactggtact tagatagatg tatatataca tgctcaaaca tgcttagata catgaagtaa   2580
catgctgcta cggtttagtc attattgagt gcctatatat tctaataaat cagtatgttt   2640
taaattattt tgatttact ggtacttaga tagtgtata tacatgct caaacatgct      2700 tagatacatg aagtaaatg ctactacggtt ttaattgttc ttgagtacct atatattcta   2760
ataaatcagt atgttttaaa ttatttcgat tttactggta cttagataga tgtatatata   2820
```

```
catgcttaga tacatgaagt aacatgctac tacggtttaa ttgttcttga atacctatat    2880
attctaataa atcagtatgt tttaaattat ttcgatttta ctggtactta gatagatgta    2940
tatatacatg ctcgaacatg cttagataca tgaagtaaca tgctacatat atattataat    3000
aaatcagtat gtcttaaatt attttgattt tactggtact tagatagatg tatatacatg    3060
ctcaaacatg cttagataca tgaagtaaca tgctactacg gtttaatcat tattgagtac    3120
ctatatattc taataaatca gtatgttttc aattgttttg attttactgg tacttagata    3180
tatgtatata tacatgctcg aacatgctta gatacgtgaa gtaacatgct actatggtta    3240
attgttcttg agtacctata tattctaata atcagtatg ttttaaatta tttcgatttt    3300
actggtactt agatagatgt atatatacat gctcgaacat gcttagatac atgaagtaac    3360
atgctactac ggtttaatcg ttcttgagta cctatatatt ctaataaatc agtatgtctt    3420
aaattatctt gattttactg gtacttagat agatgtatat acatgcttag atacatgaag    3480
taacatgcta ctatgattta atcgttcttg agtacctata tattctaata atcagtatg    3540 tttttaatta ttttgatttt actggtactt agatagatgt atatatacat gctcgaacat    3600
gcttagatac atgaagtaac atgctactac ggtttaatca ttcttgagta cctatatatt    3660
ctaataaatc agtatgtttt taattatttt gatattactg gtacttaaca tgtttagata    3720
catcatatag catgcacatg ctgctactgt ttaatcattc gtgaataccct atatattcta    3780 atatatcagt atgtcttcta attattatga ttttgatgta cttgtatggt ggcatatgct    3840
gcagctatgt gtagattttg aatacccagt gtgatgagca tgcatggcgc cttcatagtt    3900
catatgctgt ttatttcctt tgagactgtt cttttttgtt gatagtcacc ctgttgtttg    3960
gtgattctta tccagatgtc cccagagagg aggccagtgg agatcaggcc agccaccgcc    4020
gccgacatgg ccgccgtgtg cgacatcgtg aaccactaca tcgagacctc caccgtgaac    4080
ttcaggaccg agccacagac cccacaggag tggatcgacg acctcgagag gctccaggac    4140
agatacccct ggctcgtggc cgaggtggag ggcgtggtgg ccggcatcgc ctacgccggc    4200
ccctggaaag ctaggaacgc ctacgactgg accgtggagt ccaccgtgta cgtgtcccac    4260
aggcaccaga ggctcggcct cggctccacc ctctacaccc acctcctcaa gtctatggag    4320
gcccagggct tcaagtccgt ggtggccgtg atcggcctac aaaacgaccc atccgtgagg    4380
ctccacgagg ccctcggcta caccgcgaga ggcaccctca gggccgccgg ctacaagcac    4440
ggcggctggc acgacgtggg cttctggcag agggacttcg agctgccagc cccaccaagg    4500
ccagtgaggc cagtgaccca gatttgagcc aaggttcaat taagctgctg ctgtacctgg    4560
gtatctgcgt cgtctggtgc cctctggtgt acctctatat ggatctcgtc gtctaataaa    4620
catctgtggt ttgtgtgtca tcaatcgtgg ttgtggcttc gttggtttaa tggacctgtt    4680
gtgtcctctg tgttgtaccc aaaactcttc tgcagcagta tggcttgaat ccttatgaag    4740
tttgatattt gaacttaaaa gtctgctcat tatgtttttt tctggttata tctcctaatt    4800
aactgcctgg gatcaaattt gattcgctgg tgtttattgg acccctccca ggttcttgct    4860
ttctaccgtt tcttgctgaa tgttaacttg attctgtcag gctcagtttc ccactatggc    4920
ttacagctta acgtgtttgg tttgttgaat gttaacttgg ttttgtcaag ctcagttttt    4980
tactctggct tacagcataa catgtttgac ttttggtttt gctgctttgt tattgggttc    5040
tgggtagttc ttgatgaatc caaaagatca tgtgcacagc catattatct atttaagcga    5100
tccaggttat tactatgaaa ggatgccttc tagctaagga gtagttaggt ttttcttca    5160
```

```
aggttaaatt ttctcgatgc tctagtgttc ctgtgaccat aatcataata attcctttga    5220
aagctctatg gtccctggaa gcagggcata caatgcaaga cagcaacttg atcacatcaa    5280
ctgaagtata cagggttctc ttaactcttg gtgacttcgg tttaatggac cggttgtact    5340
cgtgttctat ccgtaaccgt tgtgatgtct tgtgtgtttg gttgcgggat agctgggacc    5400
acgacgtttc cgtctaattc tgatggatag ctatagacgg cactgagatg gttatattat    5460
aacctctgat cctgaactct acgagatcgt ctcatccgtc attgccacca aatacaccat    5520
taaatta                                                              5527

<210> SEQ ID NO 19
<211> LENGTH: 6067
<212> TYPE: DNA
<213> ORGANISM: Artificial Sequence
<220> FEATURE:
<223> OTHER INFORMATION: derived from Streptomyces viridochromogenes and
      Zea mays

<400> SEQUENCE: 19
agctgcttgt ggggaccaga caaaaaagga atggtgcaga attgttaggc gcacctacca      60
aaagcaactt tgcctttatt gcaaagataa agcagattcc tctagtacaa gtggggaaca     120
aaataacgtg gaaagagagct gtcctgacag cccactcact attgcgtttg acgaacgcag    180
tgacgaccac aaaactcgag acttttcaac aaagggtatt atccggaaac ctcctcggat     240
tccattgccc agctatctgt cactttattg tgaagatagt ggaaaaggaa ggtggctcct     300
acaaatgcca tcattgcgat aaaggaaagg ctatcgttga agatgcctct gccgacagtg     360
gtcccaaaga tggaccccca cccacgagga gcatcgtgga aaaagaagac gttccaacca     420
cgtcttcaaa gcaagtggat tgatgtgata tctccactga cgtaagggtt gacgaacaat     480
cccactatcc ttctgcctaa ttagctaacg gacccggaaa accaaaacaa cgaataagca     540
aactgcagga aaagtatgca gtggaaacca cccagattcc ggacgatagg aaagtatcaa     600
gtgaatgatt tgccaggaaa aggagagggg taaaagggg cgaagattta aagatctaa      660 agcacaagaa ccagagatta gattgaacaa tagggaactt ggagcatcct ttttttcttc     720
agggaaaaac tgaaaatcca aaccatgttg agcaaaaccg agtgggattg gaaaccaaaa     780
aacccgagat aaagaaactc gagaaaaagc atgaaatcga aaccaacttc agtaaaacaa     840
aaggaggaca gaaaagaaag tcggaagcta taagaatac attaacattc agtgaaacag      900
catgctgtct tcttcttttt ttatgcacaa cagagcatac atatatacct tcccaggctg     960
aggacttggc ggaggagagc cgcggatagg ttggcggtgc agacggtctg gacgggcccg    1020
aagacggaga cgaacagcgg gcccttcctg cccaggcacc acgcttggaa cgccaagcac    1080
gcgccaaccg cggccccgcc gaggacgacg atccccgcga caagcgtggc gtcgatcctg    1140
ggcgacccca gccgaggaa cctcccttcc aggacgagcc gtaggacggc ggtgagagag     1200
gcacccgtcg cggaggtggc gcagcacaag gtgagcagcg cggggaaggc ggcgagcgtg    1260
gcggcctgca ggacggtgac gagcgcgaag acggtgacgc cggcgacgag gcagcagcag    1320
ccgaggttcc agtcgtagga ggaagccgga ccaaaccggg caatgcaacc tgcagatgca    1380
ctagacggag gtaacgagga ggaggagaaa acagagcaag agcaggcgga gagaagatag    1440
agcaaaacac gagtgaggca cagcgtaagc actcggtaga agtctccaga ggcgaggtgc    1500
gcacaggaga acagatgagt aaagtcagcc aaggatgcac gatccaacgg ctacgaattt    1560
ttggagtgac gtggataggc tcaaaggcgc catttccatc cggctttata gtattttaaa    1620
```

```
aaaattcatt ttcctccctc tagtgtgtgc ggaggcgtga gcccgtttaa cggcgttgag    1680
aagtctaacg gacaccaacc acaaccagga accagcgccg gccgcgccgc cgagtgaagc    1740
agactgcata cggcacggcg cggcatctct ctggctgcct ctcgagagtt ccgcccccac    1800
cttcccgcgg tagcgtggtg gtttcgcttt ccgctgtcgg catccggaag ttgcgtggca    1860
gagtggacgg agacgaggcc gggtcctcca gctcctctca aacgtcacgg caccggcatc    1920
cggcagccag cgcggtcctt cccaaccact cgttcccaac ccatcccct tcctcgcccg     1980 ccgtcataaa tagccagccc catccccagc ttctttcccc aacctcatct tctctccttt    2040
tgctctgaac gcacacaccg cccggtctcc gatctccgat ccccgatccc ctcgtcgatc    2100
ctaggtacgg cgaccatcct acccccccc ccccccctc tctctctgcc ttctctagat      2160
cggcgatccg atccatgctt acttggttag ggcctgctaa ctatgttcat gtttgcgtta    2220
gatccgtgca tggacgcgat ctgtacacac cagacgcgtt ctgattgcta gctaactcgc    2280
cagtacctgg gaatcctggg atggctgtag ccggccccgc acgcagacgg gaccgatttc    2340
atgattctct attttttct ttgtttcgtt gcctaggggt tcgttcgatc gatccgcgtt     2400
attctttatt tccatatatt ctggtacgat gttgatacgg ttcgaccgtg ctgcttacgt    2460
tctgtgcgct tgtttgccgg gtcatttta ccttgccttt tttgtatggt ttggttgtgg     2520
cgatgtggtc tggtcgggct gtcgttctag atcggagtag agtgctgttt caaactgtct    2580
agcggatcta ttagatttgg atctgcatgt gtgacatata tcttcgtagt taagatgatg    2640
catctgtatg tgtgacatgc ggatctatta gatttggatc tgtatgtgtg acatatatct    2700
tcgtagttga gatgatgcat ctgtatgtgt gacatatatc ttcgtagtta agattatgca    2760
tggaaatatc aatcctttag ataaggacgg gtatacttgt tgctgtgggt tttactggta    2820
cttcgataga tgcatataca tgatctaaca tgcttagata catgaagtaa catgctgcta    2880
cggtttaata attcttgagt tgattttttac tggtacttag atagatgtat atacatgctt   2940
agatacatga agtaacatgc tcctacagtt cctttaatca ttattgagta cctatatatt    3000
ctaataaatc agtatgtttt aaattatttt gatttactg gtacttagat agatgtatat     3060
atacatgctc aaacatgctt agatacatga agtaacatgc tgctacggtt tagtcattat    3120
tgagtgccta tatattctaa taaatcagta tgttttaaat tattttgatt ttactggtac    3180
ttagatagat gtatatatac atgctcaaac atgcttagat acatgaagta atatgctact    3240
acggtttaat tgttcttgag tacctatata ttctaataaa tcagtatgtt ttaaattatt    3300
tcgattttac tggtacttag atagatgtat atatacatgc ttagatacat gaagtaacat    3360
gctactacgg tttaattgtt cttgaatacc tatatattct aataaatcag tatgttttaa    3420
attatttcga tttactggt acttagatag atgtatatat acatgctcga acatgcttag     3480
atacatgaag taacatgcta catatatatt ataataaatc agtatgtctt aaattatttt    3540
gattttactg gtacttagat agatgtatat acatgctcaa acatgcttag atacatgaag    3600
taacatgcta ctacggttta atcattattg agtacctata tattctaata aatcagtatg    3660
ttttcaattg ttttgatttt actggtactt agatatatgt atatatacat gctcgaacat    3720
gcttagatac gtgaagtaac atgctactat ggttaattgt tcttgagtac ctatatattc    3780
taataaatca gtatgtttta aattatttcg attttactgg tacttagata gatgtatata    3840
tacatgctcg aacatgctta gatacatgaa gtaacatgct actacggttt aatcgttctt    3900
gagtacctat atattctaat aaatcagtat gtcttaaatt atcttgattt tactggtact    3960
tagatagatg tatatacatg cttagataca tgaagtaaca tgctactatg atttaatcgt    4020
```

```
tcttgagtac ctatatattc taataaatca gtatgttttt aattattttg attttactgg    4080
tacttagata gatgtatata tacatgctcg aacatgctta gatacatgaa gtaacatgct    4140
actacggttt aatcattctt gagtacctat atattctaat aaatcagtat gtttttaatt    4200
attttgatat tactggtact taacatgttt agatacatca tatagcatgc acatgctgct    4260
actgtttaat cattcgtgaa tacctatata ttctaatata tcagtatgtc ttctaattat    4320
tatgattttg atgtacttgt atggtggcat atgctgcagc tatgtgtaga ttttgaatac    4380
ccagtgtgat gagcatgcat ggcgccttca tagttcatat gctgtttatt tcctttgaga    4440
ctgttctttt ttgttgatag tcaccctgtt gtttggtgat tcttatccag atccagatct    4500
tcgagatcct aaaccatgtc cccagagagg aggccagtgg agatcaggcc agccaccgcc    4560
gccgacatgg ccgccgtgtg cgacatcgtg aaccactaca tcgagacctc caccgtgaac    4620
ttcaggaccg agccacagac cccacaggag tggatcgacg acctcgagag gctccaggac    4680
agatacccct ggctcgtggc cgaggtggag ggcgtggtgg ccggcatcgc ctacgccggc    4740
ccctggaaag ctaggaacgc ctacgactgg accgtggagt ccaccgtgta cgtgtcccac    4800
aggcaccaga ggctcggcct cggctccacc ctctacaccc acctcctcaa gtctatggag    4860
gcccagggct tcaagtccgt ggtggccgtg atcggcctac caaacgaccc atccgtgagg    4920
ctccacgagg ccctcggcta caccgcgaga ggcaccctca gggccgccgg ctacaagcac    4980
ggcggctggc acgacgtggg cttctggcag agggacttcg agctgccagc cccaccaagg    5040
ccagtgaggc cagtgaccca gatttgagcc aaggttcaat taagctgctg ctgtacctgg    5100
gtatctgcgt cgtctggtgc cctctggtgt acctctatat ggatctcgtc gtctaataaa    5160
catctgtggt ttgtgtgtca tcaatcgtgg ttgtggcttc gttggtttaa tggacctgtt    5220
gtgtcctctg tgttgtaccc aaaactcttc tgcagcagta tggcttgaat ccttatgaag    5280
tttgatattt gaacttaaaa gtctgctcat tatgttttttt tctggttata tctcctaatt    5340
aactgcctgg gatcaaattt gattcgctgg tgtttattgg acccctccca ggttcttgct    5400
ttctaccgtt tcttgctgaa tgttaacttg attctgtcag gctcagtttc ccactatggc    5460
ttacagctta acgtgtttgg tttgttgaat gttaacttgg ttttgtcaag ctcagttttt    5520
tactctggct tacagcataa catgtttgac ttttggtttt gctgctttgt tattgggttc    5580
tgggtagttc ttgatgaatc caaaagatca tgtgcacagc catattatct atttaagcga    5640
tccaggttat tactatgaaa ggatgccttc tagctaagga gtagttaggt ttttttcttca    5700 aggttaaatt ttctcgatgc tctagtgttc ctgtgaccat aatcataata attcctttga    5760
aagctctatg gtccctggaa gcagggcata caatgcaaga cagcaacttg atcacatcaa    5820
ctgaagtata cagggttctc ttaactcttg gtgacttcgg tttaatggac cggttgtact    5880
cgtgttctat ccgtaaccgt tgtgatgtct tgtgtgtttg gttgcgggat agctgggacc    5940
acgacgtttc cgtctaattc tgatggatag ctatagacgg cactgagatg gttatattat    6000
aacctctgat cctgaactct acgagatcgt ctcatccgtc attgccacca aatacaccat    6060
taaatta                                                              6067
```

<210> SEQ ID NO 20
<211> LENGTH: 6042
<212> TYPE: DNA
<213> ORGANISM: Artificial Sequence
<220> FEATURE:
<223> OTHER INFORMATION: derived from Streptomyces viridochromogenes and Zea mays

<400> SEQUENCE: 20

```
agctgcttgt ggggaccaga caaaaaagga atggtgcaga attgttaggc gcacctacca    60
aaagcaactt tgcctttatt gcaaagataa agcagattcc tctagtacaa gtggggaaca   120
aaataacgtg gaaaagagct gtcctgacag cccactcact attgcgtttg acgaacgcag   180
tgacgaccac aaaactcgag acttttcaac aaagggtatt atccggaaac ctcctcggat   240
tccattgccc agctatctgt cactttattg tgaagatagt ggaaaaggaa ggtggctcct   300
acaaatgcca tcattgcgat aaaggaaagg ctatcgttga agatgcctct gccgacagtg   360
gtcccaaaga tggaccccca cccacgagga gcatcgtgga aaaagaagac gttccaacca   420
cgtcttcaaa gcaagtggat tgatgtgata tctccactga cgtaagggtt gacgaacaat   480
cccactatcc ttctgcctaa ttagctaacg gacccggaaa accaaaacaa cgaataagca   540
aactgcagga aaagtatgca gtggaaacca acccagattc ggacgatagg aaagtatcaa   600
gtgaatgatt tgccaggaaa aggagagggg taaaagggg cgaagattta gaagatctaa    660
agcacaagaa ccagagatta gattgaacaa tagggaactt ggagcatcct ttttttcttc   720
agggaaaaac tgaaaatcca aaccatgttg agcaaaaccg agtgggattg gaaaccaaaa   780
aacccgagat aaagaaactc gagaaaaagc atgaaatcga aaccaacttc agtaaaacaa   840
aaggaggaca gaaaagaaag tcggaagcta taaagaatac attaacattc agtgaaacag   900
catgctgtct tcttcttttt ttatgcacaa cagagcatac atatatacct tcccaggctg   960
aggacttggc ggaggagagc cgcggatagg ttggcggtgc agacggtctg gacgggcccg   1020
aagacggaga cgaacagcgg gcccttcctg cccaggcacc acgcttggaa cgccaagcac   1080
gcgccaaccg cggccccgcc gaggacgacg atccccgcga caagcgtggc gtcgatcctg   1140
ggcgacccca agccgaggaa cctcccttcc aggacgagcc gtaggacggc ggtgagagag   1200
gcacccgtcg cggaggtggc gcagcacaag gtgagcagcg cggggaaggc ggcgagcgtg   1260
gcggcctgca ggacggtgac gagcgcgaag acggtgacgc cggcgacgag gcagcagcag   1320
ccgaggttcc agtcgtagga ggaagccgga ccaaaccggg caatgcaacc tgcagatgca   1380
ctagacggag gtaacgagga ggaggagaaa acagagcaag agcaggcgga gagaagatag   1440
agcaaaacac gagtgaggca cagcgtaagc actcggtaga agtctccaga ggcgaggtgc   1500
gcacaggaga acagatgagt aaagtcagcc aaggatgcac gatccaacgg ctacgaattt   1560
ttggagtgac gtggataggc tcaaaggcgc catttccatc cggctttata gtattttaaa   1620
aaaattcatt ttcctccctc tagtgtgtgc ggaggcgtga gcccgtttaa cggcgttgag   1680
aagtctaacg gacaccaacc acaaccagga accagcgccg gccgcgccgc cgagtgaagc   1740
agactgcata cggcacggcg cggcatctct ctggctgcct ctcgagagtt ccgccccac    1800
cttcccgcgg tagcgtggtg gtttcgcttt ccgctgtcgg catccggaag ttgcgtggca   1860
gagtggacgg agacgaggcc gggtcctcca gctcctctca aacgtcacgg caccggcatc   1920
cggcagccag cgcggtcctt cccaaccact cgttcccaac ccatccccct tcctcgcccg   1980
ccgtcataaa tagccagccc catccccagc ttctttcccc aacctcatct tctctccttt   2040
tgctctgaac gcacacaccg cccggtctcc gatctccgat ccccgatccc ctcgtcgatc   2100
ctaggtacgg cgaccatcct acccccccc ccccccctc tctctctgcc ttctctagat     2160
cggcgatccg atccatgctt acttggttag ggcctgctaa ctatgttcat gtttgcgtta   2220
gatccgtgca tggacgcgat ctgtacacac cagacgcgtt ctgattgcta gctaactcgc   2280
```

-continued

```
cagtacctgg gaatcctggg atggctgtag ccggccccgc acgcagacgg gaccgatttc    2340
atgattctct attttttct ttgtttcgtt gcctagggtt tcgttcgatc gatccgcgtt     2400
attctttatt tccatatatt ctggtacgat gttgatacgg ttcgaccgtg ctgcttacgt    2460
tctgtgcgct tgtttgccgg gtcattttta ccttgccttt tttgtatggt ttggttgtgg    2520
cgatgtggtc tggtcgggct gtcgttctag atcggagtag agtgctgttt caaactgtct    2580
agcggatcta ttagatttgg atctgcatgt gtgacatata tcttcgtagt taagatgatg    2640
catctgtatg tgtgacatgc ggatctatta gatttggatc tgtatgtgtg acatatatct    2700
tcgtagttga gatgatgcat ctgtatgtgt gacatatatc ttcgtagtta agattatgca    2760
tggaaatatc aatcctttag ataaggacgg gtatacttgt tgctgtgggt tttactggta    2820
cttcgataga tgcatataca tgatctaaca tgcttagata catgaagtaa catgctgcta    2880
cggtttaata attcttgagt tgattttac tggtacttag atagatgtat atacatgctt     2940
agatacatga agtaacatgc tcctacagtt cctttaatca ttattgagta cctatatatt    3000
ctaataaatc agtatgtttt aaattatttt gattttactg gtacttagat agatgtatat    3060
atacatgctc aaacatgctt agatacatga agtaacatgc tgctacggtt tagtcattat    3120
tgagtgccta tatattctaa taaatcagta tgttttaaat tattttgatt ttactggtac    3180
ttagatagat gtatatatac atgctcaaac atgcttagat acatgaagta atatgctact    3240
acggtttaat tgttcttgag tacctatata ttctaataaa tcagtatgtt ttaaattatt    3300
tcgattttac tggtacttag atagatgtat atacatgc ttagatacat gaagtaacat      3360
gctactacgg tttaattgtt cttgaatacc tatatattct aataaatcag tatgttttaa    3420
attatttcga ttttactggt acttagatag atgtatatat acatgctcga acatgcttag    3480
atacatgaag taacatgcta catatatatt ataataaatc agtatgtctt aaattatttt    3540
gattttactg gtacttagat agatgtatat acatgctcaa acatgcttag atacatgaag    3600
taacatgcta ctacgtttta atcattattg agtacctata tattctaata atcagtatg     3660 ttttcaattg ttttgatttt actggtactt agatatatgt atatatacat gctcgaacat    3720
gcttagatac gtgaagtaac atgctactat ggttaattgt tcttgagtac ctatatattc    3780
taataaatca gtatgtttta aattatttcg attttactgg tacttagata gatgtatata    3840
tacatgctcg aacatgctta gatacatgaa gtaacatgct actacggttt aatcgttctt    3900
gagtacctat atattctaat aaatcagtat gtcttaaatt atcttgattt tactggtact    3960
tagatagatg tatatacatg cttagataca tgaagtaaca tgctactatg atttaatcgt    4020
tcttgagtac ctatatattc taataaatca gtatgttttt aattattttg attttactgg    4080
tacttagata gatgtatata tacatgctcg aacatgctta gatacatgaa gtaacatgct    4140
actacggttt aatcattctt gagtacctat atattctaat aaatcagtat gttttaatt    4200 attttgatat tactggtact taacatgttt agatacatca tatagcatgc acatgctgct    4260
actgtttaat cattcgtgaa tacctatata ttctaatata tcagtatgtc ttctaattat    4320
tatgattttg atgtacttgt atggtggcat atgctgcagc tatgtgtaga ttttgaatac    4380
ccagtgtgat gagcatgcat ggcgccttca tagttcatat gctgtttatt cctttgaga    4440 ctgttctttt ttgttgatag tcaccctgtt gtttggtgat tcttatccag atgtccccag    4500
agaggaggcc agtggagatc aggccagcca ccgccgccga catggccgcc gtgtgcgaca    4560
tcgtgaacca ctacatcgag acctccaccg tgaacttcag gaccgagcca cagaccccac    4620
aggagtggat cgacgaccte gagaggctcc aggacagata cccctggctc gtggccgagg    4680
```

```
tggagggcgt ggtggccggc atcgcctacg ccggccccctg gaaagctagg aacgcctacg   4740
actggaccgt ggagtccacc gtgtacgtgt cccacaggca ccagaggctc ggcctcggct   4800
ccaccctcta cacccacctc ctcaagtcta tggaggccca gggcttcaag tccgtggtgg   4860
ccgtgatcgg cctaccaaac gacccatccg tgaggctcca cgaggccctc ggctacaccg   4920
cgagaggcac cctcagggcc gccggctaca agcacggcgg ctggcacgac gtgggcttct   4980
ggcagaggga cttcgagctg ccagccccac caaggccagt gaggccagtg acccagattt   5040
gagccaaggt tcaattaagc tgctgctgta cctgggtatc tgcgtcgtct ggtgccctct   5100
ggtgtacctc tatatggatc tcgtcgtcta ataaacatct gtggtttgtg tgtcatcaat   5160
cgtggttgtg gcttcgttgg tttaatggac ctgttgtgtc ctctgtgttg tacccaaaac   5220
tcttctgcag cagtatggct tgaatcctta tgaagtttga tatttgaact taaaagtctg   5280
ctcattatgt ttttttctgg ttatatctcc taattaactg cctgggatca aatttgattc   5340
gctggtgttt attggacccc tcccaggttc ttgctttcta ccgtttcttg ctgaatgtta   5400
acttgattct gtcaggctca gtttcccact atggcttaca gcttaacgtg tttggtttgt   5460
tgaatgttaa cttggttttg tcaagctcag ttttttactc tggcttacag cataacatgt   5520
ttgacttttg gttttgctgc tttgttattg ggttctgggt agttcttgat gaatccaaaa   5580
gatcatgtgc acagccatat tatctattta agcgatccag gttattacta tgaaaggatg   5640
ccttctagct aaggagtagt taggtttttt cttcaaggtt aaatttttctc gatgctctag   5700 tgttcctgtg accataatca taataattcc tttgaaagct ctatggtccc tggaagcagg   5760
gcatacaatg caagacagca acttgatcac atcaactgaa gtatacaggg ttctcttaac   5820
tcttggtgac ttcggtttaa tggaccggtt gtactcgtgt tctatccgta accgttgtga   5880
tgtcttgtgt gtttggttgc gggatagctg ggaccacgac gtttccgtct aattctgatg   5940
gatagctata gacggcactg agatggttat attataaccct ctgatcctga actctacgag   6000
atcgtctcat ccgtcattgc caccaaatac accattaaat ta                       6042
```

<210> SEQ ID NO 21
<211> LENGTH: 552
<212> TYPE: DNA
<213> ORGANISM: Artificial Sequence
<220> FEATURE:
<223> OTHER INFORMATION: derived from Streptomyces viridochromogenes

<400> SEQUENCE: 21

```
atgtctccgg agaggagacc agttgagatt aggccagcta cagcagctga tatggccgcg    60
gtttgtgata tcgttaacca ttacattgag acgtctacag tgaactttag gacagagcca   120
caaacaccac aagagtggat tgatgatcta gagaggttgc aagatagata cccttggttg   180
gttgctgagg ttgagggtgt tgtggctggt attgcttacg ctgggccctg gaaggctagg   240
aacgcttacg attggacagt tgagagtact gtttacgtgt cacataggca tcaaaggttg   300
ggcctaggct ccacattgta cacacatttg cttaagtcta tggaggcgca aggttttaag   360
tcagtggttg ctgttatagg ccttccaaac gatccatctg ttaggttgca tgaggctcta   420
ggatacacag cgcggggtac actgcgcgca gctggataca agcatggtgg atggcatgat   480
gttggttttt ggcaaaggga ttttgagttg ccagctcctc caaggccagt gaggccagtt   540
acccagatct ga                                                       552
```

<210> SEQ ID NO 22

```
<211> LENGTH: 1343
<212> TYPE: DNA
<213> ORGANISM: Artificial Sequence
<220> FEATURE:
<223> OTHER INFORMATION: derived from Streptomyces viridochromogenes and
      Zea mays

<400> SEQUENCE: 22
agtcaaagat tcaaatagag gacctaacag aactcgccgt aaagactggc gaacagttca      60
tacagagtct cttacgactc aatgacaaga agaaaatctt cgtcaacttg gtggagcacg     120
acacgctagt ctactccaaa aatatcaaag atacagtctc agaagaccaa agggcaattg     180 agactttttca acaaagggta atatccggaa acctcctcgg attccattgc ccagctatct     240
gtcacttaat tgtgaagata gtggaaaagg aaggtggctc ctacaaatgc catcattgcg     300
ataaaggaaa ggccatcgtt gaagatgcct ctgccgacag tggtcccaaa gatggacccc     360
cacccacgag gagcatcgtg gtaaaagaag acgttccaac cacgtcttca aagcaagtgg     420
attgatgtga tatctccact gacgtaaggg atgacgcaca atcccactat ccttcgcaag     480
acccttcctc tatataagga agttcatttc atttggagag gataattatc caccatgtct     540
ccggagagga gaccagttga gattaggcca gctacagcag ctgatatggc cgcggtttgt     600
gatatcgtta accattacat tgagacgtct acagtgaact ttaggacaga gccacaaaca     660
ccacaagagt ggattgatga tctagagagg ttgcaagata gataccctttg gttggttgct     720 gaggttgagg gtgttgtggc tggtattgct tacgctgggc cctggaaggc taggaacgct     780
tacgattgga cagttgagag tactgtttac gtgtcacata ggcatcaaag gttgggccta     840
ggctccacat tgtacacaca tttgcttaag tctatggagg cgcaaggttt taagtcagtg     900
gttgctgtta taggccttcc aaacgatcca tctgttaggt tgcatgaggc tctaggatac     960
acagcgcggg gtacactgcg cgcagctgga tacaagcatg gtggatggca tgatgttggt    1020 tttttggcaaa gggatttttga gttgccagct cctccaaggc cagtgaggcc agttacccag    1080
atctgactaa gatcgttcaa acatttggca ataaagtttc ttaagattga atcctgttgc    1140
cggtcttgcg atgattatca tataatttct gttgaattac gttaagcatg taataattaa    1200
catgtaatgc atgacgttat ttatgagatg ggttttttatg attagagtcc cgcaattata    1260
catttaatac gcgatagaaa acaaaatata gcgcgcaaac taggataaat tatcgcgcgc    1320
ggtgtcatct atgttactag atc                                            1343

<210> SEQ ID NO 23
<211> LENGTH: 6135
<212> TYPE: DNA
<213> ORGANISM: Artificial Sequence
<220> FEATURE:
<223> OTHER INFORMATION: derived from Streptomyces viridochromogenes and
      Zea mays

<400> SEQUENCE: 23
agctgcttgt ggggaccaga caaaaaagga atggtgcaga attgttaggc gcacctacca      60
aaagcatctt tgcctttatt gcaaagataa agcagattcc tctagtacaa gtggggaaca     120
aaataacgtg gaaagagct gtcctgacag cccactcact attgcgtttg acgaacgcag     180
tgacgaccac aaaactcgag acttttcaac aaagggtaat atccggaaac ctcctcggat     240
tccattgccc agctatctgt cactttattg tgaagatagt ggaaaaggaa ggtggctcct     300
acaaatgcca tcattgcgat aaaggaaggc tatcgttga agatgcctct gccgacagtg     360
gtcccaaaga tggaccccca cccacgagga gcatcgtgga aaagaagac gttccaacca     420
```

```
cgtcttcaaa gcaagtggat tgatgtgata tctccactga cgtaagggat gacgaacaat    480
cccactatcc ttctgccgga ccctggaaaa ccaaaacaac gaataagcaa actgcaggaa    540
aagtatgcag tggaaaccaa cccagattcg gacgatagga agtatcaag tgaatgattt     600 gccaggaaaa ggagagggt aaaaaggggc gaagatttag aagatctaaa gcacaagaac     660
cagagattag attgaacaat agggaacttg gagcatcctt tttttcttca gggaaaaact    720
gaaaatccaa accatgttga gcaaaaccga gtgggattgg aaaccaaaaa acccgagata    780
aagaaactcg agaaaaagca tgaaatcgaa accaacttca gtaaaacaaa aggaggacag    840
aaaagaaagt cggaaggtat aaagaataca ttaacattca gtgaaacagc atgctgtctt    900
cttctttttt tatgcacaac agagcataca tatataccct cccaggctga ggacttggcg    960
gaggagagcc gcggagaggt tggcggtgca gacggtctgg acgggcccga agacggagac   1020
gaacagcggg cccttcctgc ccaggcacca cgcttggaac gccaagcacg cgccaaccgc   1080
ggccccgccg aggacgacga tccccgcgac aagcgtggcg tcgatcctgg gcgaccccaa   1140
gccgaggaac ctcccttcca ggacgagccg caggacggcg gtgagagagg cacccgtcgc   1200
ggaggtggcg cagcacaagg tgagcagcgc ggggaaggcg gcgagcgtgg cggcctgcag   1260
gacggtgacg agcgcgaaga cggtgacgcc ggcgacgagg cagcagcagc cgaggatcca   1320
gtcgtaggag gaagccggac caaaccgggc aatgcaacct gcagatgcac tagacggagg   1380
aaacgaggag gaggagaaaa cagagcaaga gcaggcggag agaagataga gcaaaacacg   1440
agtgaggcac agcgtaagca ctcggtagaa gtctccagag gcgaggtgcg cacaggagaa   1500
cagatgagta aagtcagcca aggatccacg atccaacggc tacgaatttt tggagtgacg   1560
tggataggct caaaggcgcc atttccatcc ggctttatag tattttaaaa aaattcattt    1620
tcctccctct agtgtgtgcg gaggcgtgag cccgtttaac ggcgttgaga agtctaacgg   1680
acaccaacca caaccaggaa ccagcgccgg ccgcgccgcc gagtgaagca gactgcatac   1740
ggcacggcgc ggcatctctc tggctgcctc tcgagagttc cgcccccacc ttcccgcggt   1800
agcgtggtgg tttcgctttc cgctgtcggc atcggaagt tgcgtggcag agtggacgga   1860
gacgaggccg ggtcctccag ctcctctcaa acgtcacggc accggcatcc ggcagccagc   1920
gcggtccttc ccaaccactc gttcccaacc catcccccctt cctcgcccgc cgtcataaat   1980
agccagcccc atccccagct tctttcccca acctcatctt ctctccttttt gctctgaacg   2040 cacacaccgc ccggtctccg atctccgatc cccgatcccc tcgtcgatcc taggtacggc   2100
gaccatcctc cccccccccc cccccctct ctctctgcct tctctagatc ggcgatccga   2160
tccatgctta cttggttagg gcctgctaac tatgttcatg tttgcgttag atccgtgcat   2220
ggacgcgatc tgtacacacc agacgcgttc tgattgctag ctaactcgcc agtacctggg   2280
aatcctggga tggctgtagc cggccccgca cgcagacggg accgatttca tgattctcta   2340 ttttttttctt tgtttcgttg cctagggttt cgttcgatcg atccgcgtta ttctttattt   2400
ccatatattc tggtacgatg ttgatacggt tcgaccgtgc tgcttacgtt ctgtgcgctt   2460
gtttgccggg tcatttttac cttgcctttt ttgtatggtt tggttgtggc gatgtggtct   2520
ggtcgggctc tcgttctaga tcggagtaga gtgctgtttc aaactgtcta gcggatctat   2580
tagatttgga tctgcatgtg tgacatatat cttcgtagtt aagatgatgc atctgtatgt   2640
gtgacatgcg gatctattag atttggatct gtatgtgtga catatatctt cgtagttgag   2700
atgatgcatc tgtatgtgtg acatatatct tcgtagttaa gattatgcat ggaaatatca   2760
```

```
atcctttaga taaggacggg tatacttgtt gctgtgggtt ttactggtac ttcgatagat    2820
gcatatacat gatctaacat gcttagatac atgaagtaac atgctgctac ggtttaataa    2880
ttcttgagtt gattttttact ggtacttaga tagatgtata tacatgctta gatacatgaa   2940
gtaacatgct cctacagttc ctttaatcat tattgagtac ctatatattc taataaatca    3000 gtatgttttta aattattttg attttactgg tacttagata gatgtatata tacatgctca   3060
aacatgctta gatacatgaa gtaacatgct gctacggttt agtcattatt gagtgcctat    3120
atattctaat aaatcagtat gttttaaatt attttgattt tactggtact tagatagatg    3180
tatatataca tgctcaaaca tgcttagata catgaagtaa tatgctacta cggtttaatt    3240
gttcttgagt acctatatat tctaataaat cagtatgttt taaattatttt cgattttact   3300 ggtacttaga tagatgtata tacatgctag atacatg aagtaacatg ctactacggt        3360
ttaattgttc ttgaataccct atatattcta ataaatcagt atgttttaaa ttatttcgat   3420
tttactggta cttagataga tgtatatata catgctcgaa catgcttaga tacatgaagt    3480
aacatgctac atatatatta taataaatca gtatgtctta aattattttg atttttactgg   3540 tacttagata gatgtatata catgctcaaa catgcttaga tacatgaagt aacatgctac    3600
tacggtttaa tcattattga gtacctatat attctaataa atcagtatgt tttcaattgt    3660
tttgatttta ctggtactta gatatatgta tatatacatg ctcgaacatg cttagatacg    3720
tgaagtaaca tgctactatg gttaattgtt cttgagtacc tatatattct aataaatcag    3780
tatgttttaa attatttcga ttttactggt acttagatag atgtatatat acatgctcga    3840
acatgcttag atacatgaag taacatgcta ctacggttta atcgttcttg agtacctata    3900
tattctaata atcagtatg tcttaaatta tcttgatttt actggtactt agatagatgt     3960
atatacatgc ttagatacat gaagtaacat gctactatga tttaatcgtt cttgagtacc    4020
tatatattct aataaatcag tatgttttta attattttga ttttactggt acttagatag    4080
atgtatatat acatgctcga acatgcttag atacatgaag taacatgcta ctacggttta    4140
atcattcttg agtacctata tattctaata atcagtatg tttttaatta tttttgatatt    4200 actggtactt aacatgttta gatacatcat atagcatgca catgctgcta ctgtttaatc    4260
attcgtgaat acctatatat tctaatatat cagtatgtct tctaattatt atgatttttga   4320 tgtacttgta tggtggcata tgctgcagct atgtgtagat tttgaatacc cagtgtgatg    4380
agcatgcatg gcgccttcat agttcatatg ctgttttattt cctttgagac tgttctttttt  4440 tgttgatagt caccctgttg tttggtgatt cttatgcaga tccagatctt cgtatttta     4500 caacaattac caacaacaac aaacaacaaa caacattaca attactattt acataaaccca   4560 tggtctaatt atccaccatg tctccggaga ggagaccagt tgagattagg ccagctacag    4620
cagctgatat ggccgcggtt tgtgatatcg ttaaccatta cattgagacg tctacagtga    4680
actttaggac agagccacaa acaccacaag agtggattga tgatctagag aggttgcaag    4740
atagataccc ttggttggtt gctgagggttg agggtgttgt ggctggtatt gcttacgctg    4800
ggccctggaa ggctaggaac gcttacgatt ggacagttga gagtactgtt tacgtgtcac    4860
ataggcatca aaggttgggc ctaggctcca cattgtacac acatttgctt aagtctatgg    4920
aggcgcaagg ttttaagtca gtggttgctg ttataggcct tccaaacgat ccatctgtta    4980
ggttgcatga ggctctagga tacacagcgc ggggtacact gcgcgcagct ggatacaagc    5040
atggtggatg gcatgatgtt ggttttttggc aaagggattt tgagttgcca gctcctccaa    5100
ggccagtgag gccagttacc cagatctgag agctcgccaa ggttcaatta agctgctgct    5160
```

```
gtacctgggt atctgcgtcg tctggtgccc tctggtgtac ctctatatgg atgtcgtcgt    5220
ctaataaaca tctgtggttt gtgtgtcatg aatcgtggtt gtggcttcgt tggtttaatg    5280
gacctgttgt gtcctctgtg ttgtacccaa aactcttctg cagcagtatg gcttgaatcc    5340
ttatgaagtt tgatatttga acttaaaagt ctgctcatta tgttttttc tggttatatc     5400 tcctaattaa ctgcctggga tcaaatttga ttcgctggtg tttattggac ccctcccagg    5460
ttcttgcttt ctaccgtttc ttgctgaatg ttaacttgat tctgtcaggc tcagtttccc    5520
actatggctt acagcttaac gtgtttggtt tgttgaatgt taacttggtt ttgtcaagct    5580
cagtttttta ctctggctta cagcataaca tgtttgactt ttggttttgc tgctttgtta    5640
ttgggttctg ggtagttctt gatgaatcca aaagatcatg tgcacagcca tattatctat    5700
ttaagcgatc caggttatta ctatgaaagg atgccttcta gctaaggagt agttaggttt    5760
tttcttcaag gttaaatttt ctcgatgctc tagtgttcct gtgaccataa tcataataat    5820
tcctttgaaa gctctatggt ccctggaagc agggcataca atgcaagaca gcaacttgat    5880
cacatcaact gaagtataca gggttctctt aactcttggt gacttcggtt taatggaccg    5940
gttgtactcg tgttctatcc gtaaccgttg tgatgtcttg tgtgtttggt tgcgggatag    6000
ctgggaccac gacgtttccg tctaattctg atggatagct atagacggca ctgagatggt    6060
tatattataa cctctgatcc tgaactctac gagatcgtct catccgtcat tgccaccaaa    6120
tacaccatta aatta                                                     6135

<210> SEQ ID NO 24
<211> LENGTH: 22
<212> TYPE: DNA
<213> ORGANISM: Artificial Sequence
<220> FEATURE:
<223> OTHER INFORMATION: derived from Streptomyces viridochromogenes

<400> SEQUENCE: 24
gcgacatcgt gaaccactac at                                             22

<210> SEQ ID NO 25
<211> LENGTH: 19
<212> TYPE: DNA
<213> ORGANISM: Artificial Sequence
<220> FEATURE:
<223> OTHER INFORMATION: derived from Streptomyces viridochromogenes

<400> SEQUENCE: 25
gctcgaggtc gtcgatcca                                                 19

<210> SEQ ID NO 26
<211> LENGTH: 21
<212> TYPE: DNA
<213> ORGANISM: Artificial Sequence
<220> FEATURE:
<223> OTHER INFORMATION: derived from Streptomyces viridochromogenes

<400> SEQUENCE: 26
ccaccgtgaa cttccgcacc g                                              21

<210> SEQ ID NO 27
<211> LENGTH: 17
<212> TYPE: DNA
<213> ORGANISM: Artificial Sequence
<220> FEATURE:
<223> OTHER INFORMATION: derived from Streptomyces viridochromogenes
```

```
<400> SEQUENCE: 27
gcgtcaggct gcacgaa                                                    17

<210> SEQ ID NO 28
<211> LENGTH: 20
<212> TYPE: DNA
<213> ORGANISM: Artificial Sequence
<220> FEATURE:
<223> OTHER INFORMATION: derived from Streptomyces viridochromogenes

<400> SEQUENCE: 28
cgaagtccct ctgccagaag                                                 20

<210> SEQ ID NO 29
<211> LENGTH: 22
<212> TYPE: DNA
<213> ORGANISM: Artificial Sequence
<220> FEATURE:
<223> OTHER INFORMATION: derived from Streptomyces viridochromogenes

<400> SEQUENCE: 29
ctacaagcac ggcggctggc ac                                              22

<210> SEQ ID NO 30
<211> LENGTH: 17
<212> TYPE: DNA
<213> ORGANISM: Artificial Sequence
<220> FEATURE:
<223> OTHER INFORMATION: derived from Streptomyces viridochromogenes

<400> SEQUENCE: 30
cgaggccctc ggctaca                                                    17

<210> SEQ ID NO 31
<211> LENGTH: 20
<212> TYPE: DNA
<213> ORGANISM: Artificial Sequence
<220> FEATURE:
<223> OTHER INFORMATION: derived from Streptomyces viridochromogenes

<400> SEQUENCE: 31
cgaagtccct ctgccagaag                                                 20

<210> SEQ ID NO 32
<211> LENGTH: 22
<212> TYPE: DNA
<213> ORGANISM: Artificial Sequence
<220> FEATURE:
<223> OTHER INFORMATION: derived from Streptomyces viridochromogenes

<400> SEQUENCE: 32
ctacaagcac ggcggctggc ac                                              22

<210> SEQ ID NO 33
<211> LENGTH: 20
<212> TYPE: DNA
<213> ORGANISM: Artificial Sequence
<220> FEATURE:
<223> OTHER INFORMATION: derived from Streptomyces viridochromogenes

<400> SEQUENCE: 33
tgagggtgtt gtggctggta                                                 20

<210> SEQ ID NO 34
<211> LENGTH: 21
```

```
<212> TYPE: DNA
<213> ORGANISM: Artificial Sequence
<220> FEATURE:
<223> OTHER INFORMATION: derived from Streptomyces viridochromogenes

<400> SEQUENCE: 34
tgtccaatcg taagcgttcc t                                              21

<210> SEQ ID NO 35
<211> LENGTH: 22
<212> TYPE: DNA
<213> ORGANISM: Artificial Sequence
<220> FEATURE:
<223> OTHER INFORMATION: derived from Streptomyces viridochromogenes

<400> SEQUENCE: 35
cttccagggc ccagcgtaag ca                                             22
```

METHODS FOR IMPROVING TRANSFORMATION FREQUENCY

RELATED APPLICATIONS

This application is a § 371 of International Application No. PCT/US2017/063343, filed Nov. 28, 2017 and designating the U.S., which claims the benefit of U.S. Provisional Application 62/731,664, filed Dec. 8, 2016, all of which are incorporated herein by reference in their entirety.

SEQUENCE LISTING

A Sequence Listing in ASCII text format, submitted under 37 C.F.R. § 1.821, entitled "81157_ST25.txt", 139 kilobytes in size, generated on Oct. 25, 2017 and filed via EFS-Web is provided in lieu of a paper copy. This Sequence Listing is hereby incorporated by reference into the specification for its disclosures.

FIELD OF THE INVENTION

The present invention relates generally to the field of plant biotechnology. More specifically, the present invention relates to compositions and methods for improving transformation frequency. Specifically, the invention includes compositions and methods for using improved selectable markers to improve transformation frequency.

BACKGROUND OF THE INVENTION

Cultivated crops such as maize, soybean, and cotton have substantial commercial value throughout the world. The development of scientific methods useful in improving the quantity and quality of important crops is, therefore, of significant commercial interest. Significant effort has been expended to improve the quality of cultivated crop species by conventional plant breeding. Conventional means for crop and horticultural improvements utilize selective breeding techniques to identify plants having desirable characteristics. However, such selective breeding techniques have several drawbacks, namely that these techniques are often labor intensive and result in plants that often contain heterogeneous genetic components that may not always result in the desirable trait being passed on from the parent plants. Advances in molecular biology have allowed mankind to modify the germplasm of animals and plants. Genetic engineering of plants entails the isolation and manipulation of genetic material (typically in the form of DNA) and the subsequent introduction of that genetic material into a plant's genome. Such technology has the capacity to deliver crops or plants having various improved economic, agronomic or horticultural traits.

The introduction of the foreign genetic material into a plant's genome is typically performed through one of two ways, although other ways are known to those skilled in the art. The first is biolistic particle bombardment, whereby the foreign DNA, or "transgene," is coated onto a metal particle, which is then shot into plant tissue. Some of that foreign genetic material is taken up by the plant cells, which are thereby "transformed." The second method is by *Agrobacterium*-mediated transformation, which involves exposing plant cells and tissues to a suspension of *Agrobacterium* cells that contain certain DNA plasmids. In both methods, the foreign DNA typically encodes for a selectable marker that permits plant cells to grow in the presence of a selection agent, for example an antibiotic or herbicide. These cells can be further manipulated to regenerate into whole fertile transgenic plants.

Glutamine synthetase (GS) constitutes in most plants one of the essential enzymes for the development and life of plant cells. It is known that GS converts glutamate into glutamine. GS is involved in an efficient pathway in most plants for the detoxification of ammonia released by nitrate reduction, amino acid degradation or photorespiration. Therefore potent inhibitors of GS are very toxic to plant cells and can be used as broad-spectrum herbicides. A class of herbicides, which include phosphinothricin (PPT) and glufosinate, are GS inhibitors. Transgenic plants have been made tolerant to this class of herbicides through the introduction of a gene encoding a phosphinothricin acetyltransferase (PAT). Such plants are said to be herbicide tolerant. In these transgenic plants, PAT detoxifies PPT by acetylation of the free amino group of PPT. The PAT gene is derived from *Streptomyces viridochromogenes* and confers tolerance to GS inhibitors. (U.S. Pat. Nos. 5,531,236, 5,646,024, 5,648, 477, and 5,276,268).

In addition to the PAT gene functioning as an herbicide tolerance trait gene for GS inhibitor herbicides, it can also be used as a selectable marker in the transformation of monocotyledonous and dicotyledonous plant species. In cereal transformation, its use is more widespread than the other selectable markers. However, although the PAT gene has been used successfully as a selectable marker, the transformation frequency is quite low, such that using it as a selectable marker is very resource intensive. An improved PAT, which can confer an increase in transformation frequency, is needed to improve the utility of PAT as a selectable marker.

SUMMARY OF THE INVENTION

The present invention provides an optionally isolated nucleic acid molecule that is at least 90% identical to any one of SEQ ID NO: 1-20. The present invention also provides for a nucleic acid molecule a chimeric nucleic acid molecule, and/or a recombinant nucleic acid construct or vector which comprise, consist, or essentially consist of a nucleic acid sequence that is any one of SEQ ID NO: 1-20. The present invention also provides for a nucleic acid molecule a chimeric nucleic acid molecule, and/or a recombinant nucleic acid construct or vector which comprise, consist, or essentially consist of a nucleic acid sequence that is at least 90% identical to any one of SEQ ID NO: 1-20.

The present invention also provides for use of a nucleic acid molecule of the invention as described herein, wherein expression of said nucleic acid molecule in a cell confers herbicide tolerance to glutamine synthetase (GS) inhibitor herbicides.

The present invention also provides for a transgenic host cell comprising a nucleic acid molecule of the invention as described herein. The transgenic host cell described above may be a bacterial cell or a plant cell. The transgenic bacterial cell may be an *Escherichia coli, Bacillus thuringiensis, Bacillus subtilis, Bacillus megaterium; Bacillus cereus, Agrobacterium* ssp. or a *Pseudomonas* ssp. cell. The transgenic plant cell may be found within a transgenic plant, plant part, plant tissue, or plant cell culture. The transgenic plant may be a monocotyledonous or dicotyledonous plant. The transgenic plant may be selected from the group comprising maize, sorghum, wheat, sunflower, tomato, crucifers, oat, turf grass, pasture grass, flax, peppers, potato, cotton, rice, soybean, sugarcane, sugar beet, tobacco, barley, and oilseed rape.

The present invention also provides for a progeny of any generation of a transgenic plant, wherein said transgenic plant comprises a nucleic acid molecule of the invention as described herein. The present invention also provides for a transgenic seed, a cutting from a transgenic plant for the purposes of propagation, and for a transgenic propagule from said transgenic plant.

The present invention also provides for an improved method of plant transformation, comprising the steps of: providing a nucleic acid molecule of the invention as described herein; (b) introducing into a plant, tissue culture, or a plant cell the nucleic acid molecule of step (a) to produce a transformed plant, transformed tissue culture, or a transformed cell having herbicide tolerance; (c) selecting for transformants using a concentration of herbicide that permits cells that express a nucleic acid molecule of step (a) to grow, while killing or inhibiting the growth of cells that do not comprise a nucleic acid molecule of the invention. This improved method with a nucleic acid molecule of the invention results in a greater transformation frequency compared to a similar method not using a nucleic acid molecule of the invention.

The present invention also provides for an improved method of producing an herbicide tolerant plant, comprising the steps of (a) providing a nucleic acid molecule of the invention as described herein; (b) introducing into a plant, tissue culture, or a plant cell the nucleic acid molecule of step (a) to produce a transformed plant, transformed tissue culture, or a transformed cell having herbicide tolerance; (c) selecting for the transformed plant, transformed tissue culture, or a transformed cell having herbicide tolerance using an appropriate amount of a GS inhibitor herbicide; and (d) growing said transformed plant or regenerating a transformed plant from the transformed tissue culture or transformed plant cell, so a herbicide tolerant plant is produced. This improved method with a nucleic acid molecule of the invention results in a greater transformation frequency compared to a similar method not using a nucleic acid molecule of the invention. In a preferred embodiment, the transgenic plant expresses a PAT gene in an amount that allows for control weeds.

The present invention also provides for a transgenic herbicide tolerant plant cell produced by the methods of the invention, and further embodiments include a transgenic herbicide tolerant plant comprising a plant cell produced by the methods of the invention. The transgenic herbicide tolerant plant cell is tolerant to herbicides comprising a GS inhibitor as its active ingredient, including phosphinothricin or a compound with a phosphinothricin moiety. The present invention also provides for a method of producing transgenic seed from the transgenic plant described above, where the plant is cultured or grown under appropriate conditions to produce progeny seed which is transgenic.

The present invention also provides an improved process for producing a transgenic plant that is tolerant to the herbicidal activity of a glutamine synthetase inhibitor, including phosphinothricin or a compound with a phosphinothricin moiety, which comprises the steps of: (a) producing a transgenic plant cell comprising a nucleic acid molecule of the invention; and (b) regenerating a transgenic plant from said cell, wherein more transgenic plant cells are recovered compared to a method that does not use a nucleic acid molecule of the invention, for example cPAT-09 or another PAT variant.

The present invention also provides for a process for protecting a group of cultivated transgenic herbicide tolerant plants in a field by destroying weeds wherein said plants comprise a nucleic acid molecule of the invention, and wherein said weeds are destroyed by application of an herbicide comprising a glutamine synthetase inhibitor as an active ingredient. The application may be, for example, at least 595 g/acre of ammonium glufosinate, at least 1190 g/acre, at least 1,785 g/acre, at least 2380 g/acre, at least 2,975 g/acre, at least 3,570 g/acre, at least 4,165 g/acre, or at least 4,760 g/acre of ammonium glufosinate.

The present invention also provides for a method of producing progeny of any generation of an herbicide tolerant fertile transgenic plant, comprising the steps of: (a) obtaining a herbicide tolerant fertile transgenic plant comprising a nucleic acid molecule of the invention as described herein; (b) collecting transgenic seed from said transgenic plant; (c) planting the collected transgenic seed; and (d) growing the progeny transgenic plants from said seed, wherein said progeny has enhanced herbicide tolerance relative to a non-transformed plant.

The present invention also provides for a method for producing a plant with herbicide tolerance, comprising the steps of sexually crossing a first parent plant with a second parent plant, wherein said first or second parent plant is a transgenic plant comprising a nucleic acid molecule of the invention as described herein. A first generation progeny plant that is a transgenic plant comprising a nucleic acid molecule of the invention as described herein is produced and is also an embodiment of the invention. The present invention also provides for a method for producing a plant with herbicide tolerance, comprising the steps of: (a) sexually crossing a first parent plant with a second parent plant, wherein said first or second parent plant is a transgenic plant comprising a nucleic acid molecule of the invention as described herein; (b) selecting a first generation progeny plant with herbicide tolerance; (c) selfing the first generation progeny plant, thereby producing a plurality of second generation progeny plants; and (d) selecting from the second generation progeny plants a plant with herbicide tolerance, wherein the second generation progeny plants comprise a nucleic acid molecule of the invention as described herein. These second generation progeny are also embodiments of the invention.

The present invention also provides for a method of selecting or distinguishing an individual plant or a group of crop plants comprising a nucleic acid molecule of the invention from a population of plants of the same species not containing the nucleic acid molecule, said method comprising applying a composition comprising a GS inhibitor as an active ingredient to the population of plants.

The present invention also provides a method of detecting a nucleic acid molecule of the invention in a sample comprising nucleic acids, said method comprising the steps of: (a) obtaining a sample comprising nucleic acids; (b) contacting the sample with a probe comprising the nucleic acid sequence of, for example, any one of SEQ ID NO: 22-32 or complements thereof, that hybridized under high stringency conditions to a nucleic acid molecule of the invention and does not hybridize under high stringency conditions with DNA of a control corn plant; (c) subjecting the sample and the probe to high stringency hybridization conditions; and (d) detecting hybridization of the probe to the DNA.

The present invention also provides a method of detecting the presence of a nucleic acid molecule of the invention in a sample comprising nucleic acids, the method comprising: (a) obtaining a sample comprising nucleic acids; (b) combining the sample with a pair of polynucleotide primers, for example SEQ ID NO: 24 and 25, SEQ ID NO: 27 and 28, or SEQ ID NO: 30 and 31, or complements thereof, which will amplify a product from a template which contains a nucleic acid molecule of the invention and will not amplify a product when the template does not contain a nucleic acid molecule of the invention; (c) performing a nucleic acid amplification reaction which results in an amplicon; and (d) detecting the amplicon.

The present invention also provides a method of detecting the presence of a nucleic acid molecule of the invention in a sample comprising nucleic acids, the method comprising: (a) obtaining a sample comprising nucleic acids; (b) combining the sample with a pair of polynucleotide primers, for example SEQ ID NO: 24 and 25, SEQ ID NO: 27 and 28, or SEQ ID NO: 30 and 31, or complements thereof, which will amplify a product from a template which contains a nucleic acid molecule of the invention and will not amplify a product when the template does not contain a nucleic acid molecule of the invention, and also combining the sample with a polynucleotide probe comprising, for example, a nucleotide sequence of SEQ ID NO: 26, SEQ ID NO: 29, SEQ ID NO: 32, or a complement thereof, which will detect the amplicon; (c) performing a nucleic acid amplification reaction which results in an amplicon which can be detected by the probe; and (d) detecting the probe.

BRIEF DESCRIPTION OF THE SEQUENCE LISTING

SEQ ID NO: 1 is a nucleic acid sequence of PAT variant 2.

SEQ ID NO: 2-5 are nucleic acid sequences of expression cassettes comprising PAT variant 2 (SEQ ID NO: 1).

SEQ ID NO: 6 is a nucleic acid sequence of PAT variant 1

SEQ ID NO: 7-10 are nucleic acid sequences of expression cassettes comprising PAT variant 1 (SEQ ID NO: 6).

SEQ ID NO: 11 is a nucleic acid sequence of PAT variant 3.

SEQ ID NO: 12-15 are nucleic acid sequences of expression cassettes comprising PAT variant 3 (SEQ ID NO: 11).

SEQ ID NO: 16 is a nucleic acid sequence of PAT variant 4.

SEQ ID NO: 17-20 are nucleic acid sequences of expression cassettes comprising PAT variant 4 (SEQ ID NO: 16).

SEQ ID NO: 21 is a nucleic acid sequence of PAT variant cPAT-09.

SEQ ID NO: 22-23 are nucleic acid sequences of expression cassettes comprising PAT variant cPAT-09 (SEQ ID NO: 21)

SEQ ID NO: 24-26 are primers and probe useful for the detection and identification of PAT variant 1 (SEQ ID NO: 6).

SEQ ID NO: 27-29 are primers and probe useful for the detection and identification of PAT variant 2 (SEQ ID NO: 1).

SEQ ID NO: 30-32 are primers and probe useful for the detection and identification of PAT variant 3 (SEQ ID NO: 11) or PAT variant 4 (SEQ ID NO: 16).

SEQ ID NO: 33-35 are primers and prove useful for the detection and identification of PAT variant cPAT-09 (SEQ ID NO: 21).

DETAILED DESCRIPTION OF THE INVENTION

The present invention provides compositions and methods for improving plant transformation frequency and for identifying, selecting, and/or producing plants and/or plant parts having herbicide tolerance to compositions comprising a glutamine synthetase (GS) inhibitor.

The methods of the present invention improve transformation frequency, which can also be referred to as transformation efficiency. "Transformation frequency" (TF) is calculated as the percentage of transgenic events for a given construct with a given number of immature embryos used for the transformation. For example, if 100 immature maize embryos were initially transformed, and it was eventually determined that 5 of the events contained full or part of the T-DNA, the transformation frequency would be 5%. By improved transformation frequency it is intended that the number of transformed plants recovered by a transformation attempt is increased by at least 10%, at least 15%, at least 20%, at least 25%, at least 30%, at least 40%, at least 50%, at least 60%, at least 70%, at least 80%, at least 90%, at least 100%, at least 125%, at least 150%, at least 175%, at least 200%, at least 300%, at least 400%, at least 500%, at least 600%, at least 700%, at least 800%, at least 900%, or at least 1000% or greater compared to a method that uses a nucleic acid molecule and/or PAT gene variant, for example cPAT-09, which is not a nucleic acid molecule of the invention.

Although the following terms are believed to be well understood by one of ordinary skill in the art, the following definitions are set forth to facilitate understanding of the presently disclosed subject matter.

All technical and scientific terms used herein, unless otherwise defined below, are intended to have the same meaning as commonly understood by one of ordinary skill in the art. References to techniques employed herein are intended to refer to the techniques as commonly understood in the art, including variations on those techniques or substitutions of equivalent techniques that would be apparent to one of skill in the art.

All patents, patent publications, non-patent publications referenced herein are incorporated by reference in their entireties for the teachings relevant to the sentence or paragraph in which the reference is presented. In case of a conflict in terminology, the present specification is controlling.

As used herein, the terms "a" or "an" or "the" may refer to one or more than one, unless the context clearly and unequivocally indicates otherwise. For example, "an" endogenous nucleic acid can mean one endogenous nucleic acid or a plurality of endogenous nucleic acids.

As used herein, the term "and/or" refers to and encompasses any and all possible combinations of one or more of the associated listed items, as well as the lack of combinations when interpreted in the alternative ("or").

As used herein, the term "about," when used in reference to a measurable value such as an amount of mass, dose, time, temperature, and the like, refers to a variation of ±0.1%, 0.25%, 0.5%, 0.75%, 1%, 2%, 3%, 4%, 5%, 6%, 7%, 8%, 9%, 10%, 15% or even 20% of the specified value as well as the specified value. Thus, if a given composition is described as comprising "about 50% X," it is to be understood that, in some embodiments, the composition comprises 50% X whilst in other embodiments it may comprise anywhere from 40% to 60% X (i.e., 50%±10%).

It will be understood that, although the terms "first," "second," etc. may be used herein to describe various elements, these elements should not be limited by these terms. These terms are only used to distinguish one element from another. Thus, a "first" element (e.g., a first promoter sequence) as described herein could also be termed a "second" element (e.g., a second promoter sequence) without departing from the teachings of the present invention.

The term "plant" refers to any plant, particularly to agronomically useful plants (e.g. seed plants), and "plant cell" is a structural and physiological unit of the plant, which comprises a cell wall but may also refer to a protoplast. The plant cell may be in form of an isolated single cell or a cultured cell, or as a part of higher organized units such as for example, a plant tissue, or a plant organ differentiated into a structure that is present at any stage of a plant's development. The promoters and compositions described herein may be utilized in any plant. A plant may be a monocotyledonous or dicotyledonous plant species. Examples of plants that may be utilized in contained embodiments herein include, but are not limited to, maize (corn), wheat, rice, barley, soybean, cotton, sorghum, beans in general, rape/canola, alfalfa, flax, sunflower, safflower, millet, rye, sugarcane, sugar beet, cocoa, tea, tropical sugar beet, *Brassica* spp., cotton, coffee, sweet potato, flax, peanut, clover; vegetables such as lettuce, tomato, cucurbits, cassava, potato, carrot, radish, pea, lentils, cabbage, cauliflower, broccoli, Brussel sprouts, peppers, and pineapple; tree fruits such as citrus, apples, pears, peaches, apricots, walnuts, avocado, banana, and coconut; and flowers such as orchids, carnations and roses. Other plants useful in the practice of the invention include perennial grasses, such as switchgrass, prairie grasses, Indiangrass, Big bluestem grass, Miscanthus and the like.

As used herein, "plant material," "plant part" or "plant tissue" means plant cells, plant protoplasts, plant cell tissue cultures from which plants can be regenerated, plant calli, plant clumps, and plant cells that are intact in plants or parts of plants such as embryos, pollen, ovules, seeds, leaves, flowers, branches, fruit, kernels, ears, cobs, husks, stalks, roots, root tips, anthers, tubers, rhizomes and the like.

As used herein, "propagule" refers to any material that is used for propagating a plant, preferably a transgenic plant, more preferably a transgenic plant comprising a nucleic acid molecule of the invention. A propagule may be a seed, cutting, or plurality of cells from a transgenic plant, which can be used to produce a crop of transgenic plants.

As used herein "plant sample" or "biological sample" refers to either intact or non-intact (e.g. milled seed or plant tissue, chopped plant tissue, lyophilized tissue) plant tissue. It may also be an extract comprising intact or non-intact seed or plant tissue. The biological sample or extract may be selected from the group consisting of corn flour, corn meal, corn syrup, corn oil, corn starch, and cereals manufactured in whole or in part to contain corn by-products.

The term "RNA" includes any molecule comprising at least one ribonucleotide residue, including those possessing one or more natural ribonucleotides of the following bases: adenine, cytosine, guanine, and uracil; abbreviated A, C, G, and U, respectively, modified ribonucleotides, and non-ribonucleotides. "Ribonucleotide" means a nucleotide with a hydroxyl group at the 2' position of the D-ribofuranose moiety.

As used herein, the terms and phrases "RNA," "RNA molecule(s)," and "RNA sequence(s)," are used interchangeably to refer to single-stranded RNA, double-stranded RNA, isolated RNA, partially purified RNA, essentially pure RNA, synthetic RNA, recombinant RNA, intracellular RNA, and also includes RNA that differs from naturally occurring RNA by the addition, deletion, substitution, and/or alteration of one or more nucleotides of the naturally occurring RNA.

As used herein, "heterologous" refers to a nucleotide sequence that either originates from another species or is from the same species or organism but is modified from either its original form or the form primarily expressed in the cell. Thus, a nucleotide sequence derived from an organism or species different from that of the cell into which the nucleotide sequence is introduced, is heterologous with respect to that cell and the cell's descendants. In addition, a heterologous nucleotide sequence includes a nucleotide sequence derived from and inserted into the same natural, original cell type, but which is present in a non-natural state, e.g. present in a different copy number, different location, and/or under the control of different regulatory sequences, than that found naturally in nature.

As used herein, the term "nucleic acid," "nucleic acid molecule," and/or "nucleotide sequence" refers to a heteropolymer of nucleotides or the sequence of these nucleotides from the 5' to 3' end of a nucleic acid molecule and includes DNA or RNA molecules, including cDNA, a DNA fragment, genomic DNA, synthetic (e.g., chemically synthesized) DNA, plasmid DNA, mRNA, and anti-sense RNA, any of which can be single stranded or double stranded. The terms "nucleotide sequence" "nucleic acid," "nucleic acid molecule," "oligonucleotide" and "polynucleotide" are also used interchangeably herein to refer to a heteropolymer of nucleotides. Nucleic acid sequences provided herein are presented herein in the 5' to 3' direction, from left to right and are represented using the standard code for representing the nucleotide characters as set forth in the sequence rules for the U.S. Patent and Trademark Office, 37 CFR § 1.821-1.825, and the World Intellectual Property Organization (WIPO) Standard ST.25.

As used herein, the term "gene" is used broadly to refer to any segment of nucleic acid associated with a biological function. Thus, genes include coding sequences and/or the regulatory sequences required for their expression. For example, "gene" refers to a nucleic acid fragment that expresses mRNA or functional RNA, or encodes a specific protein, and which includes regulatory sequences. Genes also include nonexpressed DNA segments that, for example, form recognition sequences for other proteins. Genes can be obtained from a variety of sources, including cloning from a source of interest or synthesizing from known or predicted sequence information, and may include sequences designed to have desired parameters.

"Coding sequence" refers to a DNA or RNA sequence that codes for a specific amino acid sequence and excludes the non-coding sequences. It may constitute an "uninterrupted coding sequence", i.e., lacking an intron, such as in a cDNA or it may include one or more introns bounded by appropriate splice junctions. An "intron" is a sequence of RNA which is contained in the primary transcript but which is removed through cleavage and re-ligation, or splicing, of the RNA within the cell to create the mature mRNA that can be translated into a protein.

"Operably linked" refers to the association of nucleic acid sequences on a single nucleic acid fragment so that the function of one is affected by the other. For example, a promoter is operably linked to a coding sequence or functional RNA when it is capable of affecting the expression of that coding sequence or functional RNA (i.e., that the coding sequence or functional RNA is under the transcriptional control of the promoter). Coding sequences in sense or antisense orientation can be operably-linked to regulatory sequences.

The terms "complementary" or "complementarity," or "complement" as used herein, refer to the natural binding of polynucleotides under permissive salt and temperature conditions by base-pairing. For example, the sequence "A-G-T" binds to the complementary sequence "T-C-A." The term "complementarity" includes within its meaning two single-stranded molecules that are "partial," in which only some of the nucleotides bind, or where two single-stranded molecules that are complete when total complementarity exists between the single stranded molecules. The degree of complementarity between nucleic acid strands has significant effects on the efficiency and strength of hybridization between nucleic acid strands.

The term "nucleic acid fragment," "DNA fragment" or a fragment of a gene will be understood to mean a nucleotide sequence of reduced length relative to a reference nucleic acid or nucleotide sequence and comprising, consisting essentially of and/or consisting of a nucleotide sequence of contiguous nucleotides identical or almost identical (e.g., 80%, 81%, 82%, 83%, 84%, 85%, 86%, 87%, 88%, 89%, 90%, 91%, 92%, 93%, 94%, 95%, 96%, 98%, 99% identical) to the reference nucleic acid or nucleotide sequence. Such a nucleic acid fragment according to the invention may be, where appropriate, included in a larger polynucleotide of which it is a constituent. In some embodiments, such fragments can comprise, consist essentially of and/or consist of, oligonucleotides having a length of at least about 6, 7, 8, 9, 10, 11, 12, 13, 14, 15, 16, 17, 18, 19, 20, 21, 22, 23, 24, 25, 50, 75, 100, 150, 200, 250, 300, 350, 400, 450, 500, 750, or 1000 consecutive nucleotides of a nucleic acid or nucleotide sequence according to the invention.

An "isolated" nucleic acid of the present invention is generally free of nucleic acid sequences that flank the nucleic acid of interest in the genomic DNA of the organism from which the nucleic acid was derived (such as coding sequences present at the 5' or 3' ends). However, the nucleic acid of this invention can include some additional bases or moieties that do not deleteriously affect the basic structural and/or functional characteristics of the nucleic acid. "Isolated" does not mean that the preparation is technically pure (homogeneous). Thus, an "isolated nucleic acid" is present in a form or setting that is different from that in which it is found in nature and is not immediately contiguous with nucleotide sequences with which it is immediately contiguous (one on the 5' end and one on the 3' end) in the naturally occurring genome of the organism from which it is derived. Accordingly, in one embodiment, an isolated nucleic acid includes some or all of the 5' non-coding (e.g., promoter) sequences that are immediately contiguous to a coding sequence. The term therefore includes, for example, a recombinant nucleic acid that is incorporated into a vector, into an autonomously replicating plasmid or virus, or into the genomic DNA of a prokaryote or eukaryote, or which exists as a separate molecule (e.g., a cDNA or a genomic DNA fragment produced by PCR or restriction endonuclease treatment), independent of other sequences. Thus, a nucleic acid found in nature that is removed from its native environment and transformed into a plant is still considered "isolated" even when incorporated into the genome of the resulting transgenic plant. It also includes a recombinant nucleic acid that is part of a hybrid nucleic acid encoding an additional polypeptide or peptide sequence.

The term "isolated" can further refer to a nucleic acid, nucleotide sequence, polypeptide, peptide or fragment that is substantially free of cellular material, viral material, and/or culture medium (e.g., when produced by recombinant DNA techniques), or chemical precursors or other chemicals (e.g., when chemically synthesized). Moreover, an "isolated fragment" is a fragment of a nucleic acid, nucleotide sequence or polypeptide that is not naturally occurring as a fragment and would not be found as such in the natural state. "Isolated" does not mean that the preparation is technically pure (homogeneous), but it is sufficiently pure to provide the polypeptide or nucleic acid in a form in which it can be used for the intended purpose.

The terms "polypeptide," "protein," and "peptide" refer to a chain of covalently linked amino acids. In general, the term "peptide" can refer to shorter chains of amino acids (e.g., 2-50 amino acids); however, all three terms overlap with respect to the length of the amino acid chain. As used herein, the terms "protein" and "polypeptide" are used interchangeably and encompass peptides, unless indicated otherwise. Polypeptides, proteins, and peptides may comprise naturally occurring amino acids, non-naturally occurring amino acids, or a combination of both. The polypeptides, proteins, and peptides may be isolated from sources (e.g., cells or tissues) in which they naturally occur, produced recombinantly in cells in vivo or in vitro or in a test tube in vitro, or synthesized chemically. Such techniques are known to those skilled in the art. See, e.g., Sambrook et al., Molecular Cloning: A Laboratory Manual 2nd Ed. (Cold Spring Harbor, N.Y., 1989); Ausubel et al. Current Protocols in Molecular Biology (Green Publishing Associates, Inc. and John Wiley & Sons, Inc., NY, 1987).

A "transgene" refers to a gene, polynucleotide or nucleic acid introduced into the genome of an organism by genetic manipulation in order to alter its genotype. A transgene may be introduced by transformation, recombination, or breeding. Transgenes may include, for example, genes, polynucleotides or nucleic acids that are either heterologous or homologous to the particular plant to be transformed. Additionally, transgenes may comprise native genes inserted into a non-native organism, or chimeric genes, polynucleotides or nucleic acids. A transgene can be a coding sequence, a non-coding sequence, a cDNA, a gene or fragment or portion thereof, a genomic sequence, a regulatory element and the like. A "transgenic" organism, such as a transgenic plant, transgenic microorganism, or transgenic animal, is an organism into which a transgene has been delivered or introduced and the transgene can be expressed in the transgenic organism to produce a product, the presence of which can impart an effect and/or a phenotype in the organism. "Transgenic" or "transgenic host" are used herein to include any cell, cell line, callus, tissue, plant part or plant, the genotype of which has been altered by the presence of a heterologous nucleic acid sequence, including those transgenics initially so altered as well as those created by sexual crosses or asexual propagation from the initial transgenic host cell. The term "transgenic" as used herein does not encompass the alteration of the genome (chromosomal or extra-chromosomal) by conventional plant breeding methods or by naturally occurring events such as random cross-fertilization, non-recombinant viral infection, non-recombinant bacterial transformation, non-recombinant transposition or spontaneous mutation.

The term "transgenic plant" includes reference to a plant, which comprises within its genome a heterologous nucleic acid sequence. Generally, the heterologous nucleic acid sequence is stably integrated within the genome such that the nucleic acid sequence is passed on to successive generations. The heterologous nucleic acid sequence may be integrated into the genome alone or as part of a recombinant expression cassette.

Different nucleic acids or polypeptides having homology are referred to herein as "homologues." The term homologue includes homologous sequences from the same and other species and orthologous sequences from the same and other species. "Homology" refers to the level of similarity between two or more nucleic acid and/or amino acid sequences in terms of percent of positional identity (i.e., sequence similarity or identity). Homology also refers to the concept of similar functional properties among different nucleic acids or proteins.

"Expression" refers to the transcription and stable accumulation of mRNA. Expression may also refer to the production of protein.

The terms "transcriptional cassette," "expression cassette," or "cassette" as used herein means a DNA sequence capable of directing expression of a particular nucleotide sequence in an appropriate host cell, comprising a promoter operably linked to the nucleotide sequence which is operably linked to termination signals. The expression of the nucleotide sequence in the expression cassette may be under the control of a constitutive promoter or of an inducible promoter that initiates transcription only when the host cell is exposed to some particular external stimulus. Additionally, the promoter can also be specific to a particular tissue or organ or stage of development. The expression cassette also typically comprises sequences required for proper translation of the nucleotide sequence. The coding region usually codes for a protein of interest but may also code for a functional RNA of interest, for example antisense RNA or a nontranslated RNA, in the sense or antisense direction. The transcriptional cassette comprising the nucleotide sequence of interest may be chimeric. "Chimeric" is used to indicate that a DNA sequence, such as a vector or a gene, is comprised of two or more DNA sequences of distinct origin that are fused together by recombinant DNA techniques resulting in a DNA sequence, which does not occur naturally. A transcriptional cassette, expression cassette or cassette can incorporate numerous nucleotide sequences, promoters, regulatory elements, nucleotide sequences of interest, etc.

As used herein, "vector" includes reference to a nucleic acid used in transfection of a host cell and into which can be inserted a polynucleotide. Vectors may also be referred to as "constructs" or "vector constructs". Vectors are often replicons. Expression vectors permit transcription of a nucleic acid inserted therein. "Vector" is defined to include, inter alia, any plasmid, cosmid, phage or *Agrobacterium* binary vector in double or single stranded linear or circular form which may or may not be self transmissible or mobilizable, and which can transform prokaryotic or eukaryotic host either by integration into the cellular genome or exist extrachromosomally (e.g. autonomous replicating plasmid with an origin of replication). Specifically included are shuttle vectors by which is meant a DNA vehicle capable, naturally or by design, of replication in two different host organisms, which may be selected from actinomycetes and related species, bacteria and eukaryotic (e.g. higher plant, mammalian, yeast or fungal cells).

"Trait gene" refers to transgenes of agronomic interest which provide beneficial agronomic traits to crop plants. Trait genes encode for "desired traits". Trait genes include but are not limited to genetic elements comprising or that relate to herbicide resistance, increased yield, insect control, fungal disease resistance, virus resistance, nematode resistance, bacterial disease resistance, starch production, modified oils production, high oil production, modified fatty acid content, high protein production, fruit ripening, enhanced animal and human nutrition, biopolymers, environmental stress resistance, pharmaceutical peptides, improved processing traits, improved digestibility, industrial enzyme production, improved flavor, nitrogen fixation, hybrid seed production, and biofuel production.

"Intron" refers to an intervening section of DNA which occurs almost exclusively within a eukaryotic gene, but which is not translated to amino acid sequences in the gene product. The introns are removed from the pre-mature mRNA through a process called splicing, which leaves the exons untouched, to form an mRNA. Various intron sequences have been shown to enhance expression, particularly in monocotyledonous cells. For example, the introns of the maize Adh1 gene have been found to significantly enhance the expression of the wild-type gene under its cognate promoter when introduced into maize cells. Intron 1 of Adh1 was found to be particularly effective and enhanced expression in fusion constructs with the chloramphenicol acetyltransferase gene (Callis et al. 1987, Genes Develop. 1: 1183-1200). In the same experimental system, the intron from the maize bronze 1 gene had a similar effect in enhancing expression. Intron sequences have been routinely incorporated into plant transformation vectors, typically within the non-translated leader.

"Linker" refers to a polynucleotide that comprises the connecting sequence between two other polynucleotides. The linker may be at least 1, 3, 5, 8, 10, 15, 20, 30, 50, 100, 200, 500, 1000, or 2000 polynucleotides in length. A linker may be synthetic, such that its sequence is not found in nature, or it may naturally occur, such as an intron.

"Exon" refers to a section of DNA which carries the coding sequence for a protein or part of it. Exons are separated by intervening, non-coding sequences (introns).

"Transit peptides" generally refer to peptide molecules that when linked to a protein of interest directs the protein to a particular tissue, cell, subcellular location, or cell organelle. Examples include, but are not limited to, chloroplast transit peptides, nuclear targeting signals, and vacuolar signals. To ensure localization to the plastids it is conceivable to use, but not limited to, the signal peptides of the ribulose bisphosphate carboxylase small subunit (Wolter et al. 1988, PNAS 85: 846-850; Nawrath et al., 1994, PNAS 91: 12760-12764), of the NADP malate dehydrogenase (Galiardo et al. 1995, Planta 197: 324-332), of the glutathione reductase (Creissen et al. 1995, Plant J 8: 167-175) or of the R1 protein Lorberth et al. (1998, Nature Biotechnology 16: 473-477).

The term "transformation" as used herein refers to the transfer of a nucleic acid fragment into the genome of a host cell, resulting in genetically stable inheritance. In some particular embodiments, the introduction into a plant, plant part and/or plant cell is via bacterial-mediated transformation, particle bombardment transformation, calcium-phosphate-mediated transformation, cyclodextrin-mediated transformation, electroporation, liposome-mediated transformation, nanoparticle-mediated transformation, polymer-mediated transformation, virus-mediated nucleic acid delivery, whisker-mediated nucleic acid delivery, microinjection, sonication, infiltration, polyethylene glycol-mediated transformation, protoplast transformation, or any other electrical, chemical, physical and/or biological mechanism that results in the introduction of nucleic acid into the plant, plant part and/or cell thereof, or a combination thereof.

Procedures for transforming plants are well known and routine in the art and are described throughout the literature. Non-limiting examples of methods for transformation of plants include transformation via bacterial-mediated nucleic acid delivery (e.g., via bacteria from the genus *Agrobacterium*), viral-mediated nucleic acid delivery, silicon carbide or nucleic acid whisker-mediated nucleic acid delivery, liposome mediated nucleic acid delivery, microinjection, microparticle bombardment, calcium-phosphate-mediated transformation, cyclodextrin-mediated transformation, electroporation, nanoparticle-mediated transformation, sonication, infiltration, PEG-mediated nucleic acid uptake, as well as any other electrical, chemical, physical (mechanical) and/or biological mechanism that results in the introduction of nucleic acid into the plant cell, including any combination thereof. General guides to various plant transformation methods known in the art include Miki et al. ("Procedures for Introducing Foreign DNA into Plants" in Methods in Plant Molecular Biology and Biotechnology, Glick, B. R. and Thompson, J. E., Eds. (CRC Press, Inc., Boca Raton, 1993), pages 67-88) and Rakowoczy-Trojanowska (2002, Cell Mol Biol Lett 7:849-858 (2002)).

Thus, in some particular embodiments, the introducing into a plant, plant part and/or plant cell is via bacterial-mediated transformation, particle bombardment transformation, calcium-phosphate-mediated transformation, cyclodextrin-mediated transformation, electroporation, liposome-mediated transformation, nanoparticle-mediated transformation, polymer-mediated transformation, virus-mediated nucleic acid delivery, whisker-mediated nucleic acid delivery, microinjection, sonication, infiltration, polyethyleneglycol-mediated transformation, any other electrical, chemical, physical and/or biological mechanism that results in the introduction of nucleic acid into the plant, plant part and/or cell thereof, or a combination thereof.

*Agrobacterium*-mediated transformation is a commonly used method for transforming plants because of its high efficiency of transformation and because of its broad utility with many different species. *Agrobacterium*-mediated transformation typically involves transfer of the binary vector carrying the foreign DNA of interest to an appropriate *Agrobacterium* strain that may depend on the complement of vir genes carried by the host *Agrobacterium* strain either on a co-resident Ti plasmid or chromosomally (Uknes et al 1993, Plant Cell 5:159-169). The transfer of the recombinant binary vector to *Agrobacterium* can be accomplished by a tri-parental mating procedure using *Escherichia coli* carrying the recombinant binary vector, a helper *E. coli* strain that carries a plasmid that is able to mobilize the recombinant binary vector to the target *Agrobacterium* strain. Alternatively, the recombinant binary vector can be transferred to *Agrobacterium* by nucleic acid transformation (Hagen and Willmitzer 1988, Nucleic Acids Res 16:9877).

Transformation of a plant by recombinant *Agrobacterium* usually involves co-cultivation of the *Agrobacterium* with explants from the plant and follows methods well known in the art. Transformed tissue is typically regenerated on selection medium carrying an antibiotic or herbicide resistance marker between the binary plasmid T-DNA borders.

Another method for transforming plants, plant parts and plant cells involves propelling inert or biologically active particles at plant tissues and cells. See, e.g., U.S. Pat. Nos. 4,945,050; 5,036,006 and 5,100,792. Generally, this method involves propelling inert or biologically active particles at the plant cells under conditions effective to penetrate the outer surface of the cell and afford incorporation within the interior thereof. When inert particles are utilized, the vector can be introduced into the cell by coating the particles with the vector containing the nucleic acid of interest. Alternatively, a cell or cells can be surrounded by the vector so that the vector is carried into the cell by the wake of the particle. Biologically active particles (e.g., dried yeast cells, dried bacterium or a bacteriophage, each containing one or more nucleic acids sought to be introduced) also can be propelled into plant tissue.

Thus, in particular embodiments of the present invention, a plant cell can be transformed by any method known in the art and as described herein and intact plants can be regenerated from these transformed cells using any of a variety of known techniques. Plant regeneration from plant cells, plant tissue culture and/or cultured protoplasts is described, for example, in Evans et al. (Handbook of Plant Cell Cultures, Vol. 1, MacMilan Publishing Co. New York (1983)); and Vasil I. R. (ed.) (Cell Culture and Somatic Cell Genetics of Plants, Acad. Press, Orlando, Vol. I (1984), and Vol. II (1986)). Methods of selecting for transformed transgenic plants, plant cells and/or plant tissue culture are routine in the art and can be employed in the methods of the invention provided herein.

By "stably introducing" or "stably introduced" in the context of a polynucleotide introduced into a cell is intended the introduced polynucleotide is stably incorporated into the genome of the cell, and thus the cell is stably transformed with the polynucleotide.

"Stable transformation" or "stably transformed" as used herein means that a nucleic acid is introduced into a cell and integrates into the genome of the cell. As such, the integrated nucleic acid is capable of being inherited by the progeny thereof, more particularly, by the progeny of multiple successive generations. "Genome" as used herein also includes the nuclear and the plastid genome, and therefore includes integration of the nucleic acid into, for example, the chloroplast genome. Stable transformation as used herein can also refer to a transgene that is maintained extrachromosomally, for example, as a minichromosome.

Stable transformation of a cell can be detected by, for example, a Southern blot hybridization assay of genomic DNA of the cell with nucleic acid sequences which specifically hybridize with a nucleotide sequence of a transgene introduced into an organism (e.g., a plant). Stable transformation of a cell can be detected by, for example, a Northern blot hybridization assay of RNA of the cell with nucleic acid sequences which specifically hybridize with a nucleotide sequence of a transgene introduced into a plant or other organism. Stable transformation of a cell can also be detected by, e.g., a polymerase chain reaction (PCR) or other amplification reactions as are well known in the art, employing specific primer sequences that hybridize with target sequence(s) of a transgene, resulting in amplification of the transgene sequence, which can be detected according to standard methods Transformation can also be detected by direct sequencing and/or hybridization protocols well known in the art.

The "transformation and regeneration process" refers to the process of stably introducing a transgene into a plant cell and regenerating a plant from the transgenic plant cell. As used herein, transformation and regeneration includes the selection process, whereby a transgene comprises a selectable marker and the transformed cell has incorporated and expressed the transgene, such that the transformed cell will survive and developmentally flourish in the presence of the selection agent. "Regeneration" refers to growing a whole plant from a plant cell, a group of plant cells, or a plant piece such as from a protoplast, callus, or tissue part.

A "selectable marker" or "selectable marker gene" refers to a gene whose expression in a plant cell gives the cell a selective advantage. "Positive selection" refers to a transformed cell acquiring the ability to metabolize a substrate that it previously could not use or could not use efficiently, typically by being transformed with and expressing a positive selectable marker gene. This transformed cell thereby grows out of the mass of nontransformed tissue. Positive selection can be of many types from inactive forms of plant growth regulators that are then converted to active forms by the transferred enzyme to alternative carbohydrate sources that are not utilized efficiently by the nontransformed cells, for example mannose, which then become available upon transformation with an enzyme, for example phosphomannose isomerase, that allows them to be metabolized. Non-transformed cells either grow slowly in comparison to transformed cells or not at all. Other types of selection may be due to the cells transformed with the selectable marker gene gaining the ability to grow in presence of a negative selection agent, such as an antibiotic or an herbicide, compared to the ability to grow of non-transformed cells. A selective advantage possessed by a transformed cell may also be due to the loss of a previously possessed gene in what is called "negative selection". In this, a compound is added that is toxic only to cells that did not lose a specific gene (a negative selectable marker gene) present in the parent cell (typically a transgene).

Examples of selectable markers include, but are not limited to, genes that provide resistance or tolerance to antibiotics such as kanamycin (Dekeyser et al. 1989, Plant Phys 90: 217-23), spectinomycin (Svab and Maliga 1993, Plant Mol Biol 14: 197-205), streptomycin (Maliga et al. 1988, Mol Gen Genet 214: 456-459), hygromycin B (Waldron et al. 1985, Plant Mol Biol 5: 103-108), bleomycin (Hille et al. 1986, Plant Mol Biol 7: 171-176), sulphonamides (Guerineau et al. 1990, Plant Mol Biol 15: 127-136), streptothricin (Jelenska et al. 2000, Plant Cell Rep 19: 298-303), or chloramphenicol (De Block et al. 1984, EMBO J 3: 1681-1689). Other selectable markers include genes that provide resistance or tolerance to herbicides, such as the S4 and/or Hra mutations of acetolactate synthase (ALS) that confer resistance to herbicides including sulfonylureas, imidazolinones, triazolopyrimidines, and pyrimidinyl thiobenzoates; 5-enol-pyrovyl-shikimate-3-phosphate-synthase (EPSPS) genes, including but not limited to those described in U.S. Pat. Nos. 4,940,935, 5,188,642, 5,633,435, 6,566,587, 7,674,598 (as well as all related applications) and the glyphosate N-acetyltransferase (GAT) which confers resistance to glyphosate (Castle et al. 2004, Science 304:1151-1154, and U.S. Patent Application Publication Nos. 20070004912, 20050246798, and 20050060767); BAR which confers resistance to glufosinate (see e.g., U.S. Pat. No. 5,561,236); aryloxy alkanoate dioxygenase or AAD-1, AAD-12, or AAD-13 which confer resistance to 2,4-D; genes such as *Pseudomonas* HPPD which confer HPPD resistance; Sprotophorphyrinogen oxidase (PPO) mutants and variants, which confer resistance to peroxidizing herbicides including fomesafen, acifluorfen-sodium, oxyfluorfen, lactofen, fluthiacet-methyl, saflufenacil, flumioxazin, flumiclorac-pentyl, carfentrazone-ethyl, sulfentrazone,); and genes conferring resistance to dicamba, such as dicamba monooxygenase (Herman et al. 2005, J Biol Chem 280: 24759-24767 and U.S. Pat. No. 7,812,224 and related applications and patents). Other examples of selectable markers can be found in Sundar and Sakthivel (2008, J Plant Physiology 165: 1698-1716), herein incorporated by reference.

Other selection systems include using drugs, metabolite analogs, metabolic intermediates, and enzymes for positive selection or conditional positive selection of transgenic plants. Examples include, but are not limited to, a gene encoding phosphomannose isomerase (PMI) where mannose is the selection agent, or a gene encoding xylose isomerase where D-xylose is the selection agent (Haldrup et al. 1998, Plant Mol Biol 37: 287-96). Finally, other selection systems may use hormone-free medium as the selection agent. One non-limiting example is the maize homeobox gene kn1, whose ectopic expression results in a 3-fold increase in transformation efficiency (Luo et al., 2006, Plant Cell Rep 25: 403-409). Examples of various selectable markers and genes encoding them are disclosed in Mild and McHugh (J Biotechnol, 2004, 107: 193-232; incorporated by reference).

The term "transgenic plant" includes reference to a plant, which comprises within its genome a heterologous nucleic acid sequence. Generally, the heterologous nucleic acid sequence is stably integrated within the genome such that the nucleic acid sequence is passed on to successive generations. The heterologous nucleic acid sequence may be integrated into the genome alone or as part of a recombinant expression cassette. "Transgenic" is used herein to include any cell, cell line, callus, tissue, plant part or plant, the genotype of which has been altered by the presence of a heterologous nucleic acid sequence, including those transgenics initially so altered as well as those created by sexual crosses or asexual propagation from the initial transgenic. The term "transgenic" as used herein does not encompass the alteration of the genome (chromosomal or extra-chromosomal) by conventional plant breeding methods or by naturally occurring events such as random cross-fertilization, non-recombinant viral infection, non-recombinant bacterial transformation, non-recombinant transposition or spontaneous mutation.

The terms "event," "transgenic event," or "transgenic plant event" refers to a transgenic plant produced by transformation and regeneration of a single plant cell comprising heterologous DNA, such as an expression cassette that includes a gene of interest. The term "event" also refers to progeny produced by the event.

One skilled in the art will recognize that the transgenic genotype of the invention can be introgressed by breeding into other plant lines comprising different transgenic or non-transgenic genotypes. For example, a corn inbred comprising the transgenic genotype of the invention, for example PAT variant 3 (SEQ ID NO: 11) can be crossed with a corn inbred comprising the transgenic genotype of the lepidopteran resistant MIR162 event (U.S. Pat. No. 8,232,456), thus producing corn seed that comprises both the transgenic genotype of the invention and the MIR162 transgenic genotype. It will be further recognized that other combinations can be made with the transgenic genotype of the invention and thus this example should not be viewed as limiting.

The transgenic genotype of the invention can be introgressed from the initially transformed plant, such as a corn plant, into an inbred or hybrid using art recognized breeding techniques. The goal of plant breeding is to combine in a single variety or hybrid various desirable traits. For field crops, these traits may include resistance to insects and diseases, tolerance to herbicides, tolerance to heat and drought, reducing the time to crop maturity, greater yield, and better agronomic quality. With mechanical harvesting of many crops, uniformity of plant characteristics such as germination and stand establishment, growth rate, maturity, and plant and ear height, is important.

Heterologous gene expression is used in many biotechnological applications, including transgenic plants, protein production, and metabolic engineering. One pitfall of expressing a non-native gene in a host organism is low levels of expression due at least in part to codon usage. As more and more genomes have been sequenced from a variety of organisms, it is obvious that synonymous codons are not used in equal frequencies. These codon preferences, also referred to as codon usage bias, significantly influence the expression of a heterologous gene. A highly expressed transgene whose mRNA sequence has not been optimized to the codon usage biases of its host organism, such that it frequently uses codons that are less abundant or rare in the host organism, can suffer from slow translation, including pausing or stalling of the translational machinery which can result in disassociation from the mRNA, depletion of ribosomes, depletion of pools of charged tRNA pools which can result in amino acid starvation of the host, and ultimately reduced levels of heterologous protein production. Alternatively, the use of preferred codons can increase the expression of a transgene by more than 1,000-fold (Gustafsson et al., 2004, Trends Biotechnol 22: 346-353).

Codon optimization is not simply changing all codons to a particular codon that a host is known to prefer. If all codons of a transgene are changed to a single preferred codon, high expression of the transgene in the host may still negatively affect the equilibrium of the tRNA pools maintained in the host, again leading to inefficient and possible cessation of translation of the transgene. Codon optimization of a transgene requires not only knowledge of preferred codons of a given host, but also knowledge of the relative abundances of each codon and therefore each charged tRNA pool. This method of adjusting codons to match host tRNA abundances, called codon optimization, has traditionally been used for expression of a heterologous gene. However, new strategies for optimization of heterologous expression consider global nucleotide content, local mRNA folding, codon pair bias, codon ramp, and codon correlations. Overall, it is known in the art that a desired heterologous sequence which sufficiently addresses aspects of codon bias, mRNA folding, mRNA stability, translation initiation, and translation elongation to maximize protein synthesis is difficult to predict ((Plotkin and Kudla, 2011, Nat. Rev Genet. 12(1): 32-42) and can only truly be shown empirically.

In the field of bioinformatics and computational biology, many statistical methods have been proposed to analyze codon usage bias (Hershberg and Petrov 2008). Methods such as the 'frequency of optimal codons' (Fop) (Ikemura 1981), the Relative Codon Adaptation (RCA) and the 'Codon Adaptation Index' (CAI) (Sharp and Li 1987) are used to predict gene expression levels, while methods such as the 'effective number of codons' (Nc) and Shannon entropy from information theory are used to measure codon usage evenness (Novoa and Ribas de Pouplana 2012). Multivariate statistical methods, such as correspondence analysis and principal component analysis, are widely used to analyze variations in codon usage among genes. There are many computer programs to implement the statistical analyses enumerated above, including CodonW, GCUA, and INCA. Additionally, several software packages are available online for this purpose (for example, erilllab.umbc.edu/research/software/201-2/; pbil.univ-lyon1.fr/datasets/charif04/; mcinerneylab.com/software/gcua/#; thermofisher.com/us/en/home/life-science/cloning/vector-nti-software/vector-nti-advance-software.html).

A skilled person would recognize that during the insertion of a nucleic acid molecule, such as any one of SEQ ID NO: 1-20, into a cell, the 5' and/or 3' ends of the inserted molecule may be deleted or rearranged. Such deletions or rearrangements may not affect the function of the inserted molecule, and these relatively small changes result in an inserted molecule that may be considered to be essentially the same as the starting molecule. A skilled person would also recognize that the nucleic acid molecule, such as one comprising any one of SEQ ID NO: 1-20, may undergo full or partial rearrangement or duplication during the insertion event, such that the inserted molecule is a full or partial rearrangement or duplication of the starting nucleic acid molecule. A skilled person would recognize that this inserted molecule may still have the same characteristics and/or traits as the starting molecule, such that the transformed cell or resulting transformed plant may still be desirable.

A skilled person would recognize that a transgene for commercial use, such as a nucleic acid molecule that comprises any one of SEQ ID NO: 1-20, may need relatively minor modifications to the nucleic acid sequence to comply with governmental regulatory standards. Such modifications would not affect the function of the molecule. A skilled person would recognize that the modified nucleic acid molecule would be essentially the same as the starting molecule.

Therefore, the invention encompasses a nucleic acid molecule substantially identical to any one of SEQ ID NO: 1-20, wherein certain nucleotides of any one of SEQ ID NO: 1-20 are deleted, substituted or rearranged, resulting in a mutated nucleic acid molecule and wherein the functionality of the mutated nucleic acid molecule is the same as the starting molecule. The present invention also provides for a nucleic acid molecule, a chimeric nucleic acid molecule, and/or a recombinant nucleic acid construct or vector which comprise, consist, or essentially consist of a nucleic acid sequence that is at least 90% identical, at least 95% identical, at least 97% identical, at least 98% identical, at least 99% identical, or 100% identical to any one of SEQ ID NO: 1-20. The present invention also provides an isolated nucleic acid molecule that is at least 90% identical, at least 95% identical, at least 97% identical, at least 98% identical, at least 99% identical, or 100% identical to any one of SEQ ID NO: 1-20. The present invention also provides an isolated nucleic acid molecule that is at least 90% identical, at least 92% identical, at least 94% identical, at least 95% identical, at least 97% identical, at least 98% identical, at least 99% identical, or 100% identical to SEQ ID NO: 1, SEQ ID NO: 6, SEQ ID NO: 11, and/or SEQ ID NO: 16. The present invention also provides for a nucleic acid molecule, a chimeric nucleic acid molecule, and/or a recombinant nucleic acid construct or vector which comprise, consist, or consist essentially of any one of SEQ ID NO: 1-20.

In one embodiment, this chimeric nucleic acid molecule of the invention may comprise additional expression cassettes, transcriptional or translational regulatory elements, or prokaryotic origins of replication. In another embodiment, the chimeric nucleic acid molecule may be a recombinant nucleic acid construct, such as a binary vector or a vector suitable for expression in prokaryotes. The recombinant nucleic acid construct may be suitable for transient or stable expression in plants. In another embodiment, the invention encompasses any one of SEQ ID NO: 1-20 or a nucleic acid molecule that is substantially identical any one of SEQ ID NO: 1-20 as either an isolated nucleic acid molecule or as part of a larger nucleic acid molecule.

The present invention also provides for use of a nucleic acid molecule of the invention as described herein, wherein expression of said nucleic acid molecule in a cell confers herbicide tolerance to glutamine synthetase (GS) inhibitor herbicides. GS inhibitor herbicides include phosphinothricin (PPT), glufosinate, bialaphos, Basta, glufosinate ammonium-GLA, or a compound with a phosphinothricin moiety.

Commercial GS inhibitor herbicides include Interline™, Herbiace®, Liberty®, Ignite®, Rely®, Finale®, and Basta®.

The present invention also provides for a transgenic host cell comprising a nucleic acid molecule of the invention as described herein. The transgenic host cell described above may be a bacterial cell or a plant cell. The transgenic bacterial cell may be an *Escherichia coli, Bacillus thuringiensis, Bacillus subtilis, Bacillus megaterium; Bacillus cereus, Agrobacterium* ssp. or a *Pseudomonas* ssp. cell. The transgenic plant cell may be found within a transgenic plant, plant part, plant tissue, or plant cell culture. The transgenic plant may be a monocotyledonous or dicotyledonous plant. The transgenic plant may be selected from the group comprising maize, sorghum, wheat, sunflower, tomato, crucifers, oat, turf grass, pasture grass, flax, peppers, potato, cotton, rice, soybean, sugarcane, sugar beet, tobacco, barley, and oilseed rape.

The present invention also provides for a progeny of any generation of a transgenic plant, wherein said transgenic plant comprises a nucleic acid molecule of the invention as described herein. The present invention also provides for a transgenic seed, a cutting from a transgenic plant for the purposes of propagation, and for a transgenic propagule from said transgenic plant.

The present invention also provides for an improved method of plant transformation, comprising the steps of: providing a nucleic acid molecule of the invention as described herein; (b) introducing into a plant, tissue culture, or a plant cell the nucleic acid molecule of step (a) to produce a transformed plant, transformed tissue culture, or a transformed cell having herbicide tolerance; (c) selecting for transformants using a concentration of herbicide that permits cells that express a nucleic acid molecule of step (a) to grow, while killing or inhibiting the growth of cells that do not comprise a nucleic acid molecule of the invention. This improved method with a nucleic acid molecule of the invention results in a greater transformation frequency compared to a similar method not using a nucleic acid molecule of the invention. The herbicide comprises a GS inhibitor, such as phosphinothricin or glufosinate. Examples of appropriate amounts of GS inhibitor herbicide for selecting a transformed cell having herbicide tolerance range from 1 to 80 mg/L ammonium glufosinate. A preferred range is 1 to 60 mg/L ammonium glufosinate. This improved method provides at least 5% higher, 10% higher, 15% higher, 20% higher, 25% higher, 30% higher, 40% higher, 50% higher, 60% higher, 70% higher, 80% higher, 90% higher, 100% higher, 110% higher, 120% higher, 130% higher, 140% higher, 150% higher, 160% higher, 170% higher, 180% higher, 190% higher, 200% higher, 300% higher, 400% higher, 500% higher, 600% higher, 700% higher, 800% higher, 900% higher, or at least 1000% higher transformation frequency compared to a method that uses a nucleic acid molecule and/or PAT gene variant, for example cPAT-09, which is not a nucleic acid molecule of the invention.

The present invention also provides for an improved method of producing an herbicide tolerant plant, comprising the steps of (a) providing a nucleic acid molecule of the invention as described herein; (b) introducing into a plant, tissue culture, or a plant cell the nucleic acid molecule of step (a) to produce a transformed plant, transformed tissue culture, or a transformed cell having herbicide tolerance; (c) selecting for the transformed plant, transformed tissue culture, or a transformed cell having herbicide tolerance using an appropriate amount of a GS inhibitor herbicide; and (d) growing said transformed plant or regenerating a transformed plant from the transformed tissue culture or transformed plant cell, so a herbicide tolerant plant is produced. This improved method with a nucleic acid molecule of the invention results in a greater transformation frequency compared to a similar method not using a nucleic acid molecule of the invention. This improved method provides at least 5% higher, 10% higher, 15% higher, 20% higher, 25% higher, 30% higher, 40% higher, 50% higher, 60% higher, 70% higher, 80% higher, 90% higher, 100% higher, 110% higher, 120% higher, 130% higher, 140% higher, 150% higher, 160% higher, 170% higher, 180% higher, 190% higher, 200% higher, 300% higher, 400% higher, 500% higher, 600% higher, 700% higher, 800% higher, 900% higher, or at least 1000% higher transformation frequency compared to a method that uses a nucleic acid molecule and/or PAT gene variant, for example cPAT-09, which is not a nucleic acid molecule of the invention. Examples of appropriate amounts of GS inhibitor herbicide for selecting a transformed cell having herbicide tolerance range from 1 to 80 mg/L ammonium glufosinate. A preferred range is 1 to 60 mg/L ammonium glufosinate. In a preferred embodiment, the transgenic plant expresses a PAT gene in an amount that allows for control weeds.

The present invention also provides for a transgenic herbicide tolerant plant cell produced by the methods of the invention, and further embodiments include a transgenic herbicide tolerant plant comprising a plant cell produced by the methods of the invention. The transgenic herbicide tolerant plant cell is tolerant to herbicides comprising a GS inhibitor as its active ingredient, including phosphinothricin or a compound with a phosphinothricin moiety. The present invention also provides for a method of producing transgenic seed from the transgenic plant described above, where the plant is cultured or grown under appropriate conditions to produce progeny seed which is transgenic.

The present invention also provides an improved process for producing a transgenic plant that is tolerant to the herbicidal activity of a glutamine synthetase inhibitor, including phosphinothricin or a compound with a phosphinothricin moiety, which comprises the steps of: (a) producing a transgenic plant cell comprising a nucleic acid molecule of the invention; and (b) regenerating a transgenic plant from said cell, wherein more transgenic plant cells are recovered compared to a method that does not use a nucleic acid molecule of the invention, for example cPAT-09 or another PAT variant.

The present invention also provides for a process for protecting a group of cultivated transgenic herbicide tolerant plants in a field by destroying weeds wherein said plants comprise a nucleic acid molecule of the invention, and wherein said weeds are destroyed by application of an herbicide comprising a glutamine synthetase inhibitor as an active ingredient. The application may be, for example, at least 595 g/acre of ammonium glufosinate, at least 1190 g/acre, at least 1,785 g/acre, at least 2380 g/acre, at least 2,975 g/acre, at least 3,570 g/acre, at least 4,165 g/acre, or at least 4,760 g/acre of ammonium glufosinate.

The present invention also provides for a method of producing progeny of any generation of an herbicide tolerant fertile transgenic plant, comprising the steps of: (a) obtaining a herbicide tolerant fertile transgenic plant comprising a nucleic acid molecule of the invention as described herein; (b) collecting transgenic seed from said transgenic plant; (c) planting the collected transgenic seed; and (d) growing the progeny transgenic plants from said seed, wherein said progeny has enhanced herbicide tolerance relative to a non-transformed plant.

The present invention also provides for a method for producing a plant with herbicide tolerance, comprising the steps of sexually crossing a first parent plant with a second parent plant, wherein said first or second parent plant is a transgenic plant comprising a nucleic acid molecule of the invention as described herein. A first generation progeny plant that is a transgenic plant comprising a nucleic acid molecule of the invention as described herein is produced and is also an embodiment of the invention. The present invention also provides for a method for producing a plant with herbicide tolerance, comprising the steps of: (a) sexually crossing a first parent plant with a second parent plant, wherein said first or second parent plant is a transgenic plant comprising a nucleic acid molecule of the invention as described herein; (b) selecting a first generation progeny plant with herbicide tolerance; (c) selfing the first generation progeny plant, thereby producing a plurality of second generation progeny plants; and (d) selecting from the second generation progeny plants a plant with herbicide tolerance, wherein the second generation progeny plants comprise a nucleic acid molecule of the invention as described herein. These second generation progeny are also embodiments of the invention.

The present invention also provides for a method of selecting or distinguishing an individual plant or a group of crop plants comprising a nucleic acid molecule of the invention from a population of plants of the same species not containing the nucleic acid molecule, said method comprising applying a composition comprising a GS inhibitor as an active ingredient to the population of plants.

The present invention also provides a method of detecting a nucleic acid molecule of the invention in a sample comprising nucleic acids, said method comprising the steps of: (a) obtaining a sample comprising nucleic acids; (b) contacting the sample with a probe comprising the nucleic acid sequence of, for example, any one of SEQ ID NO: 22-32 or complements thereof, that hybridized under high stringency conditions to a nucleic acid molecule of the invention and does not hybridize under high stringency conditions with DNA of a control corn plant; (c) subjecting the sample and the probe to high stringency hybridization conditions; and (d) detecting hybridization of the probe to the DNA.

The present invention also provides a method of detecting the presence of a nucleic acid molecule of the invention in a sample comprising nucleic acids, the method comprising: (a) obtaining a sample comprising nucleic acids; (b) combining the sample with a pair of polynucleotide primers, for example SEQ ID NO: 24 and 25, SEQ ID NO: 27 and 28, or SEQ ID NO: 30 and 31, or complements thereof, which will amplify a product from a template which contains a nucleic acid molecule of the invention and will not amplify a product when the template does not contain a nucleic acid molecule of the invention; (c) performing a nucleic acid amplification reaction which results in an amplicon; and (d) detecting the amplicon.

The present invention also provides a method of detecting the presence of a nucleic acid molecule of the invention in a sample comprising nucleic acids, the method comprising: (a) obtaining a sample comprising nucleic acids; (b) combining the sample with a pair of polynucleotide primers, for example SEQ ID NO: 24 and 25, SEQ ID NO: 27 and 28, or SEQ ID NO: 30 and 31, or complements thereof, which will amplify a product from a template which contains a nucleic acid molecule of the invention and will not amplify a product when the template does not contain a nucleic acid molecule of the invention, and also combining the sample with a polynucleotide probe comprising, for example, a nucleotide sequence of SEQ ID NO: 26, SEQ ID NO: 29, SEQ ID NO: 32, or a complement thereof, which will detect the amplicon; (c) performing a nucleic acid amplification reaction which results in an amplicon which can be detected by the probe; and (d) detecting the probe.

EXAMPLES

The invention will be further described by reference to the following detailed examples. These examples are provided for purposes of illustration only, and are not intended to be limiting unless otherwise specified. Standard recombinant DNA and molecular cloning techniques used here are well known in the art and are described by Ausubel (ed.), Current Protocols in Molecular Biology, John Wiley and Sons, Inc. (1994); J. Sambrook, et al., Molecular Cloning: A Laboratory Manual, 3d Ed., Cold Spring Harbor, N.Y.: Cold Spring Harbor Laboratory Press (2001); and by T. J. Silhavy, M. L. Berman, and L. W. Enquist, Experiments with Gene Fusions, Cold Spring Harbor Laboratory, Cold Spring Harbor, N.Y. (1984).

Example 1: PAT Codon Optimization

The PAT codon optimized nucleic acid sequences were produced using the codon usage tool available from the Vector NTI Advance® software. Using standard algorithms and available ESTs for various monocotyledonous crops, codon optimized sequences were derived from the native nucleic acid sequence of PAT from *S. viridochromogenes*. Variant 1 (SEQ ID NO: 6) was produced by codon optimization to a wild relative of domesticated *Zea mays*, namely *Zea mays* ssp. *mexicana*. Variant 2 (SEQ ID NO: 1) was produced by codon optimization to barley (*Hordeum vulgare*). Variant 3 (SEQ ID NO: 11) was produced by a novel method of codon optimization to *Sorghum bicolor* and also to *Oryza sativa*. Variant 4 (SEQ ID NO: 16) was produced by codon optimization to *Sorghum bicolor*. A control PAT DNA sequence, referred to as cPAT-09 (SEQ ID NO: 21), was produced by codon optimization to a dicotyledonous plant species, *Arabidopsis thaliana*. Percent similarity of these sequences to each other and to the native PAT nucleic acid sequence is shown in Table 1.

TABLE 1

Percent similarity between codon optimized PAT nucleic acid sequences

|  | cPAT 09 | Variant 1 | Native PAT (*S. viridochromogenes*) | Variant 2 | Variant 3 | Variant 4 |
| --- | --- | --- | --- | --- | --- | --- |
| cPAT 09 | 100 | 73 | 71 | 73 | 76 | 78 |
| Variant 1 |  | 100 | 85 | 81 | 84 | 87 |
| Native PAT (*S. viridochromogenes*) |  |  | 100 | 88 | 86 | 84 |

TABLE 1-continued

Percent similarity between codon optimized PAT nucleic acid sequences

| | cPAT 09 | Variant 1 | Native PAT (S. viridochromogenes) | Variant 2 | Variant 3 | Variant 4 |
|---|---|---|---|---|---|---|
| Variant 2 | | | 100 | | 94 | 91 |
| Variant 3 | | | | | 100 | 95 |
| Variant 4 | | | | | | 100 |

Example 2: PAT Variants Expression Cassettes

Each variant was introduced into four different expression cassettes, which were introduced into binary vectors (Table 2). All expression cassettes for the variants contain the prZmUbi158 maize promoter to drive expression and are terminated by the tZmUbi158 terminator (U.S. Pat. No. 9,187,756, herein incorporated by reference). The expression cassette design types a, b, c, and d used the four PAT coding sequence variants. The expression cassette design types a-d may have additional features such as transcriptional enhancers eFMV and e35S, and a 25 nucleotides (25nt) region at the junction between the prZmUbi158 intron and the PAT coding sequence. This 25 nt region may have a role in transgene expression (for example, see Sivamani et al., 2009, Plant Science 177: 549-556, herein incorporated by reference). eFMV is a modified figwort mosaic virus enhancer (Maiti et al. 1997, Transgenic Res 6: 143-156). e35S is a cauliflower mosaic virus 35S enhancer region which can activate heterologous core promoters (Ow et al. 1987, PNAS 84: 4870-4874). The control construct 18857 contains an expression cassette comprising the 35s promoter (Odell et al. 1985, Nature 313: 810-812) driving expression of the A. thaliana optimized PAT gene (cPAT-09) operably linked to a NOS terminator (Bevan et al. 1983, Nucleic Acids Res 11: 369-385). 18857, similar to design type "b", lacks enhancers and also lacks the 25 nt region. The other control construct, 20189, is similar to design type "c" and contains the eFMV and e35S enhancers and the 25 nt region. PAT variant types may be referred to as a combination of the PAT variant sequence and the cassette design type. For example, PAT variant 3b has the PAT variant 3 in expression cassette design type b (SEQ ID NO: 13).

TABLE 2

Construct details

| Binary vector ID | PAT expression cassette | SEQ ID NO. | PAT Variant | Cassette Design type | Features |
|---|---|---|---|---|---|
| 23152 | prUbi158/cPAT/tZmUbi158 | 2 | Variant 2 | a | Without enhancers; with 25nt |
| 23153 | prZmUbi158/cPAT/tZmUbi158 | 3 | | b | Without enhancers; without 25 nt |
| 23173 | eFMV/e35S/ prZmUbi158/cPAT/tZmUbi158 | 4 | | c | With enhancers; with 25 nt |
| 23213 | eFMV/ e35S/ prZmUbi158/cPAT/tZmUbi158 | 5 | | d | With enhancers; without 25 nt |
| 23150 | prZmUbi158/cPAT/tZMUbi158 | 7 | Variant 1 | a | Without enhancers; with 25 nt |
| 23151 | prZmUbi158/cPAT/tZmUbi158 | 8 | | b | Without enhancers; without 25 nt |
| 23166 | eFMV/e35S/ prZmUbi158/cPAT/tZmUbi158 | 9 | | c | With enhancers; with 25 nt |
| 23184 | eFMV/e35S/ prZmUbi158/cPAT/tZmUbi158 | 10 | | d | With enhancers; without 25 nt |
| 23185 | prZmUbi158/cPAT/tZmUbi158 | 12 | Variant 3 | a | Without enhancers; with 25 nt |
| 23154 | prZmUbi158/cPAT/tZmUbi158 | 13 | | b | Without enhancers; without 25 nt |
| 23174 | eFMV/e35S/ prZmUbi158/cPAT/tZmUbi158 | 14 | | c | With enhancers; with 25 nt |
| 23200 | eFMV/e35S/ prZmUbi158/cPAT/tZmUbi158 | 15 | | d | With enhancers; without 25 nt |
| 23148 | prZmUbi158/cPAT/tZmUbi158 | 17 | Variant 4 | a | Without enhancers; with 25 nt |
| 23149 | prZmUbi158/cPAT/tZmUbi158 | 18 | | b | Without enhancers; without 25 nt |
| 23164 | eFMV/e35S/ prZmUbi158/cPAT/tZmUbi158 | 19 | | c | With enhancers; with 25 nt |
| 23165 | eFMV/e35S/ prZmUbi158/cPAT/tZmUbi158 | 20 | | d | With enhancers; without 25 nt |
| 18857 | pr35S/cPAT/tNOS | 22 | Control | C1 | 35s promoter and NOS terminator (control 1) |
| 20189 | eFMV/e35S/ prZmUbi158/cPAT/tZmUbi158 | 23 | Control | C2 | With enhancers; with 25 nt (control 2) |

Example 3: Transient Assays to Characterize PAT Variant Expression Levels

Transient assays were performed with all binary vector constructs listed in Table 2 with appropriate controls. Maize plants 8-10 days after germination were used for transient assays using *Agrobacterium* strains each comprising a vector from Table 2. The tops of the plants were cut from the second fully opened leaf and the remaining leaves were also cut to expose the stem of the plant. The stem was then mechanically bruised. One 1 mL of Agrobacteria suspension was applied. Two plants were infiltrated for each test construct. The infiltrated plants were placed in a tray and maintained in a growth chamber around 25° C. with a photoperiod of 16 h light and 8 h dark for 4 days. After 4 days, 4 samples from the newly grown leaf tissue from each plant were collected, total protein was extracted, and PAT protein levels were determined using an ELISA kit from EnviroLogix (catalog number AP014 NWv10; www.envirologix.com). The ELISA results of transient assay are presented in Table 3. PAT protein values are an average of 8 leaf samples collected from two maize plants that were infiltrated with the Agrobacteria containing the respective binary vector, with standard deviation shown. The values are expressed as nanogram PAT enzyme per milligram total soluble protein (TSP). All PAT variants in all expression cassettes expressed at levels higher than that of the control constructs.

TABLE 3

Protein levels of PAT variants in transient assays

| Vector ID | PAT variant | Cassette design type | PAT protein (ng/mg TSP) |
|---|---|---|---|
| 23152 | Variant 2 | a | 1053.7 ± 627.2 |
| 23153 | | b | 897.4 ± 383.6 |
| 23173* | | c | 657.3 ± 577.3 |
| 23213* | | d | 1351.5 ± 869.2 |
| 23150 | Variant 1 | a | 224.9 ± 158.2 |
| 23151 | | b | 489.7 ± 346.9 |
| 23166 | | c | 651.8 ± 261.5 |
| 23184 | | d | 1563.4 ± 855.1 |
| 23185 | Variant 3 | a | 576.8 ± 318.8 |
| 23154** | | b | 1153.5 ± 691.6 |
| 23174 | | c | 491.7 ± 546.1 |
| 23200 | | d | 1542.9 ± 944.6 |
| 23148 | Variant 4 | a | 332.9 ± 200.5 |
| 23149* | | b | 139.4 ± 113.6 |
| 23164 | | c | 147.3 ± 36.4 |
| 23165 | | d | 398.0 ± 139.1 |
| 18857 | Control | Control 1 | 18.8 ± 25.2 |
| 20189 | | Control 2 | 93.8 ± 27.7 |

Example 4: PAT Variants in Transgenic Plants

Each of the binary vectors of Table 2 was used to create maize transgenic events. Events were produced by *Agrobacterium*-mediated transformation of a proprietary maize line Immature embryos were transformed essentially as described in Negrotto et al. (2000, Plant Cell Reports 19: 798-803, herein incorporated by reference). Using this method, genetic elements within the left and right border regions of the binary vector comprising the PAT expression cassette were efficiently transferred and integrated into the genome of the plant cell, while genetic elements outside these border regions were not transferred.

The PAT gene was used as a selectable marker during the transformation process otherwise performed essentially as Negrotto et al. 2000, with bialaphos/ammonium glufosinate concentration ranging from 1-7.5 (Bialaphos) or 10-40 (ammonium glufosinate) mg/L in the selection media. The embryos producing embryogenic calli were transferred to a series of cell culture selection media containing bialaphos/ammonium glufosinate as selection agent and cultured for 10-11 weeks in total. The selection media also contained 200 mg/ml timentin and/or 10 ml/l PPM (Plant Preservative Mix) to ensure that all Agrobacteria was cleared from the transformed tissue. Regenerated plants were transferred to the greenhouse for further propagation.

Example 5: PAT Variant Transformation Frequencies

Percentage of transformation frequency (TF) was calculated, and the data are presented in Table 3. Transformation frequency is calculated as the percentage of transgenic events recovered for a given construct over the number of immature embryos used for the transformation. Standard deviation is shown for each construct. Interestingly, for PAT variants 3 and 4, the cassette designs that lacked the enhancers (3a, 3b, 4a and 4b) showed higher TF than the cassettes that were built with the enhancers (3c, 3d, 4c and 4d). Surprisingly, the cassette types with enhancers for all variants yielded sick looking plants. The constructs 23152 (type 2a), 23173 (type 2c), 23213 (type 2d), 23154 (type 3b) and 23149 (type 4b) yielded statistically significant higher TF compared with that of others and controls in multiple experiments in a consistent manner (Table 4). Although the transformation frequency of 23173 (type 2c) and 23213 (type 2d) were high, the transgenic events showed severe abnormal looking plants most likely due to the over expression of the PAT gene and the overexpression of a reporter CFP gene, due to the presence of enhancers. The transgenic events from 23154 (type 3b) and 23149 (type 4b) were normal looking. Statistical analysis was performed on the TF results. In a two tailed student's t test, TF was significantly higher when using vector 23152, 23173, 23213, and 23149 when compared to controls, with a p value of ≤0.05. Unexpectedly, TF was even more significant higher for one construct, 23154, (type 3b), with a p value of ≤0.01 when compared to controls in a student's t test. Overall, these results show that the best variant and best cassette design type for maximal transformation frequency is not obvious and cannot be predicted.

TABLE 4

Transformation frequency in transgenic plants

| Vector ID | PAT variant | Cassette design type | # of expts | # of explants | # of transgenic events obtained | # of single copy events | Transformation frequency % (TF) |
|---|---|---|---|---|---|---|---|
| 23152* | Variant 2 | a | 4 | 892 | 60 | 18 | 6.7 ± 1.5 |
| 23153 | | b | 5 | 1000 | 42 | 11 | 4.2 ± 0.7 |

TABLE 4-continued

Transformation frequency in transgenic plants

| Vector ID | PAT variant | Cassette design type | # of expts | # of explants | # of transgenic events obtained | # of single copy events | Transformation frequency % (TF) |
|---|---|---|---|---|---|---|---|
| 23173* | | c | 2 | 302 | 20 | 7 | 6.6 ± 1.1 |
| 23213* | | d | 2 | 360 | 25 | 15 | 6.9 ± 0.9 |
| 23150 | Variant 1 | a | 3 | 589 | 21 | 5 | 3.6 ± 1.4 |
| 23151 | | b | 7 | 1380 | 75 | 7 | 5.4 ± 1.3 |
| 23166 | | c | 2 | 370 | 10 | 2 | 2.7 ± 0.2 |
| 23184 | | d | 2 | 360 | 14 | 1 | 3.9 ± 0.1 |
| 23185 | Variant 3 | a | 4 | 1030 | 45 | 4 | 4.4 ± 0.6 |
| 23154** | | b | 4 | 900 | 71 | 13 | 7.9 ± 0.9 |
| 23174 | | c | 2 | 300 | 10 | 8 | 3.3 ± 0.9 |
| 23200 | | d | 2 | 620 | 23 | 8 | 3.7 ± 2.2 |
| 23148 | Variant 4 | a | 2 | 496 | 24 | 5 | 4.8 ± 1.5 |
| 23149* | | b | 3 | 595 | 40 | 5 | 6.7 ± 2.0 |
| 23164 | | c | 2 | 395 | 12 | 4 | 3.0 ± 1.1 |
| 23165 | | d | 2 | 386 | 10 | 2 | 2.6 ± 0.5 |
| 18857 | Control | Control 1 | 10 | 2210 | 82 | 4 | 3.7 ± 0.6 |
| 20189 | | Control 2 | 13 | 3800 | 172 | 9 | 4.5 ± 0.4 |

Asterisks indicate significant differences in transformation frequency in a two tailed student's t test;
for *, $p \leq 0.05$;
for **, $p \leq 0.01$.

Example 6: PAT Variant Protein Levels in Transgenic Plants

Leaf extracts from T0 transgenic plants, which were the initially transformed plants, were prepared and were quantitatively analyzed for PAT by ELISA (Tijssen 1985) using a kit from EnviroLogix (catalog number AP014 NWv10; www.envirologix.com). Results for ELISAs are an average from the total numbers of plants sampled and shown as nanogram PAT enzyme per milligram total solution protein (TSP). Standard deviation is shown for each construct. Interestingly, the PAT protein expression in leaves of transgenic T0 plants transformed with the new codon optimized constructs, with or without enhancers, was several fold higher (ranging up to 89 fold) than the controls which comprised cPAT-09, which is also plant optimized. The cassette design types c and d (Table 2) with the transcriptional enhancers showed higher expression of the PAT gene over the types a and b (Table 2) that lacked the enhancers. Interestingly, the 23154 construct, which comprised PAT variant type 3b, is not among the highest of PAT protein levels in its leaves compared to other constructs which had lower TF. This indicates that a PAT variant and expression cassette design type which acts as an improved selectable marker for improved transformation frequency cannot be predicted based high levels of PAT protein.

TABLE 5

Expression of PAT in transgenic events

| Vector ID | PAT variant | Cassette design type | # of plants sampled for ELISA | PAT protein (ng/mg TSP) |
|---|---|---|---|---|
| 23152* | Variant 2 | a | 18 | 2051.5 ± 456.5 |
| 23153 | | b | 11 | 2014.5 ± 596.6 |
| 23173* | | c | 7 | 2816.9 ± 637.6 |
| 23213* | | d | 15 | 4804.8 ± 778.8 |
| 23150 | Variant 1 | a | 5 | 899.9 ± 200.5 |
| 23151 | | b | 7 | 747.8 ± 125.8 |
| 23166 | | c | 2 | 1513.6 ± 87.1 |
| 23184 | | d | 1 | 2642.4 ± 411.8 |
| 23185 | Variant 3 | a | 4 | 469.4 ± 47.1 |
| 23154** | | b | 13 | 474.0 ± 43.4 |
| 23174 | | c | 8 | 925.0 ± 158.3 |
| 23200 | | d | 8 | 733.7 ± 84.4 |
| 23148 | Variant 4 | a | 13 | 297.1 ± 46.1 |
| 23149* | | b | 5 | 1014.7 ± 84.1 |
| 23164 | | c | 8 | 859.4 ± 6.7 |
| 23165 | | d | 5 | 263.3 ± 45.7 |
| 18857 | Control | Control 1 | 41 | 53.8 ± 13.0 |
| 20189 | | Control 2 | 63 | 109.3 ± 19.5 |

Example 7: PAT Variant Transgene Copy Number

For transgene copy number determination, the TAQMAN™ assay was performed with total DNA extracted from leaf pieces from each putative T0 transgenic event as described by Ingham et al. (2001). DNA from the putative transgenic events was isolated using standard procedures and analyzed using TAQMAN™ qPCR to determine copy number of the introduced gene. TAQMAN™ assays were performed following standard methodology using Jump-Start™ Taq ReadyMix™ (Sigma-Aldrich) and the ABI PRISM® 7900HT sequence detection system. Primers and probes for the introduced variants are shown in Table 6. These primers and probes could also be used to identify the presence of a PAT variant in a DNA sample using TAQMAN™. In all the blocks, DNA from a one copy PMI transgene maize event as determined by Southern blot was used as control. Events were considered low-copy if they had a raw TAQMAN™ copy number value of 0.3 to 1.3. Events with a raw TAQMAN™ number above 1.3 were considered medium to high copy number and are believed to contain more than one copy of the introduced gene. The transgenic events identified as low copy were used for further analysis.

TABLE 6

TaqMan primers and probes

| SEQ ID NO: | Description | Sequence |
|---|---|---|
| 24 | variant 1 Fwd primer | GCGACATCGTGAACCACTACAT |
| 25 | variant 1 Rev primer | GCTCGAGGTCGTCGATCCA |
| 26 | variant 1 probe | CCACCGTGAACTTCCGCACCG |
| 27 | variant 2 Fwd primer | GCGTCAGGCTGCACGAA |
| 28 | variant 2 Rev primer | CGAAGTCCCTCTGCCAGAAG |
| 29 | variant 2 probe | CTACAAGCACGGCGGCTGGCAC |
| 30 | variant 3 & 4 Fwd primer | CGAGGCCCTCGGCTACA |
| 31 | variant 3 & 4 Rev primer | CGAAGTCCCTCTGCCAGAAG |
| 32 | variant 3 & 4 probe | CTACAAGCACGGCGGCTGGCAC |
| 33 | cPAT-09 Fwd primer | TGAGGGTGTTGTGGCTGGTA |
| 34 | cPAT-09 Rev primer | TGTCCAATCGTAAGCGTTCCT |
| 35 | cPAT-09 probe | CTTCCAGGGCCCAGCGTAAGCA |

Example 8: Herbicide Spray Results with T0 Transgenic Events

Backbone free low copy events comprising each of the variant types were selected and maintained in GH and sprayed with 4× levels of the herbicide Liberty™ containing the active ingredient ammonium glufosinate, a glutamate synthetase (GS) inhibitor. All the sprayed T0 events raised from the 16 different codon optimized PAT vectors showed herbicide resistance as good as the controls. No visible leaf damage was found in any of the T0 transgenic events. This indicates that PAT variant type 3b, in addition to surprisingly providing improved transformation frequency when acting as the selectable marker, can act at a commercial level as an herbicide tolerance trait. These sprayed T0 events were transferred to bigger pots and seeds were collected from all the events.

Example 9: Herbicide Tolerance in T1 PAT Variant 3b Transgenic Plants

A sum of 40 T1 seeds from 4 T0 events from the construct 23154 (PAT variant type 3b), which gave consistent higher TF and significantly higher PAT expression over controls in repeated experiments, were germinated. The germinating seedlings were tested for the presence of PAT gene by TaqMan® PCR analysis, as described in Example 7, and for protein expression of the PAT gene, as described in Example 6. Similarly, 25 T1 seeds from two T0 transgenic events each of control constructs 18857 and 20189 were germinated and assayed for the presence of PAT gene by TaqMan® PCR. The plants that were negative for the presence of PAT gene were discarded and the positive plants were randomly separated into two sets for spray tests at 4× (2,380 g/acre active ingredient of ammonium glufosinate (Liberty 280SL™ with 4 g/200 ml ammonium sulphate as carrier) and 8× (4,760 g/acre active ingredient of ammonium glufosinate (Liberty 280SL™) levels at the V3/V4 stage with appropriate controls (18857 and 20189). For each rate of spray, 5 non transgenic maize were maintained as control with and without the ammonium glufosinate spray. This strategy is shown in Table 7.

TABLE 7

Herbicide tolerance in T1 generation of PAT variant 3b transgenic plants

| Vector ID | T0 parent ID | # of plants sprayed at 4X | # of plants sprayed at 8X | Total plants sprayed |
|---|---|---|---|---|
| 23154 | 19A006A | 15 | 16 | 107 |
|  | 19A011A | 15 | 10 |  |
|  | 19A034A | 11 | 12 |  |
|  | 19A036A | 12 | 16 |  |
| 18857 | 15A010A | 3 | 23 | 45 |
|  | 28A006A | 19 | 0 |  |
| 20189 | 23A014A | 19 | 4 | 39 |
|  | 29A003A | 0 | 16 |  |

One week after the spray, the leaves were scored for leaf damage/necrosis. All the 107 T1 events of 23154 (both heterozygous and homozygous) showed resistance to ammonium glufosinate herbicide spray as good as the controls at 4× and 8× levels. No damage was observed to the plants even with the 8× spray in transgenic events from 23154 or the controls. This indicates that PAT variant 3b maintains full efficacy as a trait in multiple generations, in addition to acting as an improved selectable marker for transformation.

Example 10: Ammonium Glufosinate Concentrations for Selection of PAT Variant 3b A kill curve was conducted to determine the most effective concentration of ammonium glufosinate that could be used with the PAT variant type 3b. The expression cassette of PAT variant type 3b (SEQ ID NO: 13) was introduced into a binary vector, now referred to as 23419. Binary vector 18857 (described in Table 2), which expresses cPAT-09, was used as a control. An effective concentration of ammonium glufosinate is high enough to minimize or eliminate false positives, or "escapes", which do not have the PAT gene but survive selection, but low enough to not kill transgenic plants which do comprise the PAT gene. For vector 23419, 75-86 immature embryos were transformed using Agrobacteria similar to the method described in Example 4. Selection was performed using 10-80 mg/L of ammonium glufosinate (Ignite®). Following selection, plantlets were regenerated and then transferred to rooting media. The survival percentage (%) is shown as the number of plants that rooted over the number of immature embryos initially transformed. Results are shown in Table 8.

TABLE 8

Ammonium glufosinate concentration for PAT variant 3b transformation

| Ammonium glufosinate (mg/L) | % Survival, PAT variant 3b | % Survival, cPAT-09 |
|---|---|---|
| 10 | 7.1 | 1.3 |
| 20 | 11.6 | 1.3 |
| 40 | 5.8 | 0 |
| 80 | 0 | 0 |

10 mg/L to 40 mg/L of ammonium glufosinate all had survivor transgenic plant candidates for the binary vector comprising PAT variant type 3b. Survival percentage from transformation using cPAT-09 (binary vector 18857) was much lower, and did not survive selection at 40 mg/L ammonium glufosinate. A second experiment was performed using 40 mg/L ammonium glufosinate, or using the GS inhibitor bialaphos at 5 mg/L. For this experiment, following transformation the immature embryos were selected, plants were regenerated and rooted, and transgenic plants were identified so that transformation frequency could be calculated. Results are shown in Table 9.

TABLE 9

Improved transformation frequency of PAT variant 3b

| Treatment | PAT variant | Valid Explants | Total # Events | Transformation frequency % (TF) |
|---|---|---|---|---|
| 5 mg/L Bialaphos | 3b | 400 | 13 | 3.25 |
|  | cPAT-09 | 825 | 7 | 0.875 |
| 40 mg/L ammonium glufosinate | 3b | 400 | 16 | 4 |
|  | cPAT-09 | 825 | 5 | 0.625 |

Transformation using PAT variant type 3b is clearly shown to result in a higher transformation frequency compared to cPAT-09 using either 40 mg/L ammonium glufosinate or using 5 mg/L bialaphos.

Example 11: PAT Variant 3b Transgenic Plant Herbicide Tolerance in the Field

Field efficacy for the PAT variant type 3b (SEQ ID NO: 13) is tested. SEQ ID NO: 13 is introduced into maize plants as described in Example 4. Herbicide tolerant corn plants comprising SEQ ID NO: 13 are tested in a hybrid cross grown at a field location. For example, efficacy trials consist of one-row plots, with three replications per treatment. The treatment may consist of an application of 2× or 4× the maximum labeled rate applied at the V4 developmental stage of the corn plant. Phytotoxicity may be assessed at 7 days and 14 days after treatment (7 DAT and 14 DAT). Factors of phytotoxicity that are taken into account when rating phytotoxicity include leaf discoloration (for example yellowing of leaf tips or margin), leaf damage (for example burning of leaf tips or margin), and plant growth stunting (for example inadequate elongation between internodes). Phytotoxicity may be quantified as the percentage of plants showing phytotoxicity at 7 or 14 days after V4 application.

What is claimed:

1. An isolated nucleic acid molecule comprising a nucleic acid sequence at least 95% identical to any one of SEQ ID NO: 11, SEQ ID NO: 12, SEQ ID NO: 13, SEQ ID NO: 14, and SEQ ID NO: 15 wherein said sequence encodes a phosphinothricin acetyltransferase (PAT) enzyme.

2. A vector or construct comprising the nucleic acid molecule of claim 1.

3. A transgenic host cell that contains the nucleic acid molecule of claim 1.

4. The cell of claim 3, which is a bacterial cell.

5. The cell of claim 3, which is a plant cell.

6. A plant or plant part comprising the plant cell of claim 5.

7. The plant of claim 6, wherein said plant is a monocotyledonous plant.

8. The plant of claim 7, wherein said plant is millet, switchgrass, maize, sorghum, wheat, oat, turf grass, pasture grass, rice, sugarcane, or barley.

9. The plant of claim 6, wherein said plant further comprises a nucleic acid molecule comprising a nucleotide sequence which encodes for at least one additional desired trait selected from the group consisting of insect resistance, abiotic stress tolerance, increased yield, improved oil profile, improved fiber quality, delayed ripening, male sterility, herbicide resistance, bacterial disease resistance, fungal disease resistance, viral disease resistance, nematode resistance, modified fatty acid metabolism, modified carbohydrate metabolism, production of a commercially valuable enzyme or metabolite, improved nutritional value, improved performance in an industrial process and altered reproductive capability.

10. A progeny of any generation of the plant of claim 6 that comprises the isolated nucleic acid molecule encoding a PAT enzyme.

11. A propagule of any generation of the plant of claim 6 that comprises the isolated nucleic acid molecule encoding a PAT enzyme.

12. An improved method of plant transformation, comprising the steps of:
   a. providing the nucleic acid molecule of claim 1;
   b. introducing into a plant, tissue culture, or a plant cell the nucleic acid molecule of step (a) to obtain a transformed plant, transformed tissue culture, or a transformed cell expressing PAT from the nucleic acid molecule of step (a); and
   c. selecting for transformants using a concentration of herbicide that permits cells that express PAT from the nucleic acid molecule of step (a) to grow, while killing or inhibiting the growth of cells that do not comprise said PAT gene, wherein said herbicide comprises phosphinothricin or glufosinate,
wherein more transformants are recovered compared to a method that does not use the nucleic acid molecule.

13. A transgenic herbicide tolerant plant cell produced by the method of claim 12.

14. A transgenic herbicide tolerant plant produced from the plant cell of claim 13.

15. An improved method of selecting for a transgenic plant cell, wherein said method comprises providing the nucleic acid molecule of claim 1 to a plurality of plant cells, and growing said plurality of cells in a concentration of a herbicide that permits cells comprise the PAT enzyme to grow while killing or inhibiting the growth of cells that do not comprise said enzyme, wherein said herbicide comprises phosphinothricin or glufosinate, and wherein more transgenic plant cells are recovered compared to a method that does not use the nucleic acid.

16. An improved process for producing a transgenic plant that is tolerant to the herbicidal activity of a glutamine synthetase inhibitor, including phosphinothricin or a compound with a phosphinothricin moiety, which comprises the steps of:
   a. producing a transgenic plant cell comprising the nucleic acid molecule of claim 1; and
   b. regenerating a transgenic plant from said cell,
wherein more transgenic plant cells comprising a PAT gene are recovered compared to a method that does not use the nucleic acid molecule.

17. A process for protecting a group of cultivated transgenic herbicide tolerant plants in a field by destroying weeds, comprising the steps of cultivating transgenic plants comprising the nucleic acid molecule of claim 1, and destroying said weeds by application of a herbicide comprising a glutamine synthetase inhibitor as an active ingredient.

* * * * *